United States Patent
Niu et al.

(10) Patent No.: US 12,202,812 B2
(45) Date of Patent: Jan. 21, 2025

(54) GLYCOSYL DONOR, PREPARATION METHOD THEREFOR, AND USE THEREOF

(71) Applicant: SICHUAN UNIVERSITY, Sichuan (CN)

(72) Inventors: Dawen Niu, Sichuan (CN); Xia Zhang, Sichuan (CN); Liqiang Wan, Sichuan (CN); Chen Zhang, Sichuan (CN); Demeng Xie, Sichuan (CN)

(73) Assignee: SICHUAN UNIVERSITY, Sichuan (CN)

( * ) Notice: Subject to any disclaimer, the term of this patent is extended or adjusted under 35 U.S.C. 154(b) by 233 days.

(21) Appl. No.: 17/428,562

(22) PCT Filed: Jul. 21, 2020

(86) PCT No.: PCT/CN2020/103340
§ 371 (c)(1),
(2) Date: Aug. 4, 2021

(87) PCT Pub. No.: WO2021/013155
PCT Pub. Date: Jan. 28, 2021

(65) Prior Publication Data
US 2022/0127239 A1    Apr. 28, 2022

(30) Foreign Application Priority Data

Jul. 23, 2019 (CN) .......................... 201910668449.8

(51) Int. Cl.
| | | |
|---|---|---|
| *C07D 309/08* | (2006.01) | |
| *C07D 307/18* | (2006.01) | |
| *C07D 307/20* | (2006.01) | |
| *C07D 309/10* | (2006.01) | |
| *C07D 405/12* | (2006.01) | |
| *C07D 405/14* | (2006.01) | |
| *C07D 407/12* | (2006.01) | |
| *C07D 493/06* | (2006.01) | |
| *C07D 493/10* | (2006.01) | |
| *C07H 1/00* | (2006.01) | |
| *C07H 15/14* | (2006.01) | |
| *C07H 15/203* | (2006.01) | |
| *C07H 15/26* | (2006.01) | |
| *C07H 17/02* | (2006.01) | |
| *C07H 17/04* | (2006.01) | |

(52) U.S. Cl.
CPC ......... *C07D 309/08* (2013.01); *C07D 307/18* (2013.01); *C07D 405/12* (2013.01); *C07D 405/14* (2013.01); *C07D 407/12* (2013.01); *C07D 493/06* (2013.01); *C07D 493/10* (2013.01); *C07B 2200/07* (2013.01)

(58) Field of Classification Search
CPC ............... C07D 309/08; C07D 309/10; C07D 307/18; C07D 307/20; C07D 405/12; C07D 405/14; C07D 407/12; C07D 493/06; C07D 493/10; Y02P 20/55; C07B 2200/07; C07H 17/02; C07H 17/04; C07H 1/00; C07H 13/04; C07H 15/14; C07H 15/203; C07H 15/26
See application file for complete search history.

(56) References Cited

FOREIGN PATENT DOCUMENTS

| CN | 105593163 A | 5/2016 |
|---|---|---|
| EP | 0290203 A1 | 11/1988 |

OTHER PUBLICATIONS

Ferrier et al., registry database compound, 1978.*
Ferrier. Robert Jet al. "Observations on the Possible Application of Glycosyl Disulfides. Sulfenic Esters. and Sulfones in the Synthesis of Glycosides" Carbohydrate Research, vol. 58,, No. 2, 1977-12-31, Issn: 1873-426X, p. 399 lines 9-11.
Konradsson, Peter et al. "Iodonium Promoted Reactions of Disarmed Thioglycosides" Tetrahedron Letters, vol. 31., No. 30, Mar. 9, 2001, ISSN: 0040-4039, p. 4314, table 1.
Sakata. Masakatsu et al. "Thiosugars. VI. Reaction Products of Potassium Alkyl- and Benzylxanthates with Acetylated Glucosyl Halides" Chemical & Pharmaceutical Bulletin, vol. 12, No. 6, Dec. 31, 1964, ISSN: 0009-2363, pp. 652-656, p. 655 line 12.
Lockhoff, Oswald. "An Access to Glycoconjugate Libraries through Multicomponent Reactions" Angewandte Chemie International Edition, vol. 37., No. 24, Jan. 18, 1999, ISSN: 1433-7851, p. 3437, Scheme 3.
Krumb, Matthias et al. "Visible Light Enables Aerobic Iodine Catalyzed Glycosylation" European Journal of Organic Chemistry, vol. 2019, No. 28, Feb. 22, 2019, ISSN: 1099-0690, p. 4519, Scheme 2.
Adak, Laksmikanta et al. "Synthesis of Aryl C-Glycosides via Iron-Catalyzed Cross Coupling of Halosugars: Stereoselective Anomeric Arylation of Glycosyl Radicals" Journal of the American Chemical Society, vol. 139, No. 31., Aug. 1, 2017, ISSN: 0002-7863, p. 10693-10701, p. 10696, table 5.

* cited by examiner

*Primary Examiner* — Sun Jae Yoo
(74) *Attorney, Agent, or Firm* — NKL Law; Allen Xue

(57) ABSTRACT

A glycosyl donor represented by formula (I) is used for preparing an S-glycoside compound represented by formula (III), an O-glycoside compound represented by formula (V), and a C-glycoside compound represented by formula (V). The glycosyl donor is a raw material in the preparation of O-glycoside, S-glycoside, and C-glycoside compounds by means of a free radical reaction, most of which have a special α configuration.

6 Claims, No Drawings

GLYCOSYL DONOR, PREPARATION METHOD THEREFOR, AND USE THEREOF

TECHNICAL FIELD

The present invention relates to the technical fields of synthetic chemistry and medicinal chemistry, and in particular to a new glycosyl donor, as well as the preparative method and the use thereof.

BACKGROUND ART

Carbohydrates are an important part of living organisms (including animals, plants, and microorganisms). Polysaccharides, oligosaccharides and their complexes with proteins, esters, etc. involve cells, especially all the time and space processes of multicellular life. They are used as information molecules to participate in various recognition processes of cells such as transmitting biological information, participate in the body's immune regulation, and is closely related to various functions including cell differentiation, fertilization, embryonic development, blood system, infection, aging, and so on. In recent years, due to the remarkable physiological activity of carbohydrate compounds, extensive research interest of more and more chemists have been attracted. Glycosides are the important form for sugar to exist in nature, which is widely present in organisms, has special biological activities, and is responsible for important physiological functions. Glycosides are a very important class of compounds formed by the condensation of the hemiacetal hydroxyl groups in sugars and ligands by losing a molecule of water or other small molecule of compounds, in which the sugar moiety is called glycosyl and the non-sugar moiety is called aglycon. Glycoside compounds can be divided into O-glycoside compounds, N-glycoside compounds, S-glycoside compounds and C-glycoside compounds according to the type of the atom linking the aglycon and the carbon atom of sugar ring in the molecular structure of a glycoside compound. Most of them exhibit good biological functions, such as inhibitory activity of glycosidase, as well as antibacterial, antiviral and antitumor activities, etc.

Currently, there are many methods for constructing glycoside compounds, but the conditions of these methods are not mild enough, and the compatibility of functional groups is poor. At the same time, most of the existing methods are difficult to prepare glycoside compounds in a configuration with high stereoselectivity.

Therefore, the study on glycosyl donors with novel structures that can be prepared by simple methods has great application value for the further preparation of various glycoside compounds (such as O-glycoside compounds, N-glycoside compounds, S-glycoside compounds, and C-glycoside compounds).

CONTENT OF THE INVENTION

In order to solve the above-mentioned problems, the present invention provides an allylsulfone-type of glycosyl donor with a novel structure, that is used as a starting material to prepare S-glycoside compounds, O-glycoside compounds, and C-glycoside compounds.

The present invention provides a glycosyl donor, or a salt thereof, or a stereoisomer thereof, or an optical isomer thereof, and the glycosyl donor has a structure of formula I:

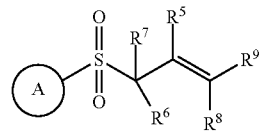

Formula I

Wherein, ring A is selected from

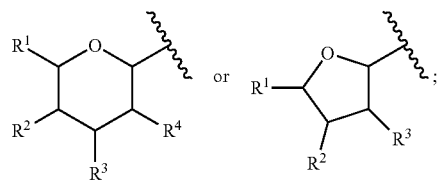

each of $R^1$, $R^2$, $R^3$, and $R^4$ is independently selected from the group consisting of H, $C_{1-6}$ alkyl, aryl or heteroaryl substituted $C_{1-12}$ alkyl, $C_{1-12}$ alkoxyl, $C_{2-8}$ alkynyl, $C_{2-8}$ alkenyl, aryl, heteroaryl, cycloalkyl, $M_1OH$, $M_1NH_2$, $M_1NHAc$, $M_1OAc$, $M_1OBz$, $M_1OBn$, $M_1N_3$, $M_1OTMS$, $M_1OTBS$,

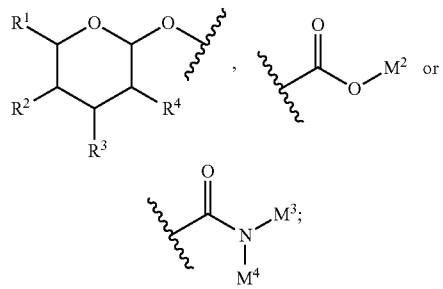

or any two of $R^1$, $R^2$, $R^3$, and $R^4$ are linked to form a ring, $M_1$ is selected from 0-3 methylene; $M^2$, $M^3$, $M^4$ are selected from the group consisting of H, $C_{1-6}$ alkyl, aryl or heteroaryl substituted $C_{1-12}$ alkyl, $C_{2-8}$ alkynyl, $C_{2-8}$ alkenyl, aryl, heteroaryl; or $M^3$ and $M^4$ are linked to form a ring;

$R^5$ is selected from the group consisting of $C_{1-10}$ alkyl, saturated cycloalkyl, saturated heterocyclyl, H, aryl, heteroaryl, $C_{1-10}$ alkoxyl, halogen, cyano, carboxyl, ester group;

Each of $R^6$, $R^7$, $R^8$, and $R^9$ is independently selected from the group consisting of H, halogen, $C_{1-6}$ alkyl, $C_{1-6}$ alkoxyl, $M_1OH$, $C_{2-8}$ alkynyl, $C_{2-8}$ alkenyl, saturated cycloalkyl, saturated heterocyclyl, H, aryl, heteroaryl, cyano, ester group; $M_1$ is selected from 0-3 methylene.

Further, the glycosyl donor has a structure of formula II-1 or II-2:

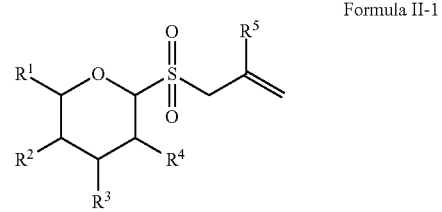

Formula II-1

-continued

Formula II-2

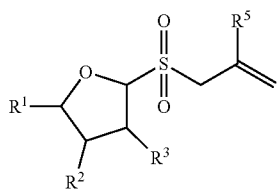

Wherein, each of $R^1$, $R^2$, $R^3$, and $R^4$ is selected from the group consisting of H, $C_{1-6}$ alkyl, $C_{1-6}$ alkoxyl, $C_{2-6}$ alkynyl, $C_{2-6}$ alkenyl, aryl, heteroaryl, cycloalkyl, $M_1OH$, $M_1NH_2$, $M_1NHAc$, $M_1OAc$, $M_1OBz$, $M_1OBn$, $M_1N_3$, $M_1OTMS$, $M_1OTBS$,

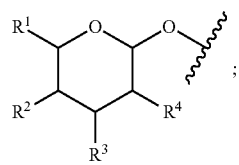

or any two of $R^1$, $R^2$, $R^3$, $R^4$ are linked to form a substituted or unsubstituted ring, and each of the substituents in the ring is independently selected from one or more of H, D, $C_{1-8}$ alkyl, $C_{1-8}$ alkoxyl, $C_{2-8}$ alkynyl, $C_{2-8}$ alkenyl, aryl, heteroaryl, halogen, cyano, carboxy or ester group;

$M_1$ is selected from 0-3 methylene;

$R^5$ is selected from the group consisting of $C_{1-8}$ alkyl, saturated cycloalkyl, saturated heterocyclyl, H, aryl, heteroaryl, $C_{1-8}$ alkoxyl, halogen, cyano, carboxyl, ester group;

Preferably, each of said $R^1$, $R^2$, $R^3$, $R^4$ is independently selected from the group consisting of H, $C_{1-6}$ alkyl, $C_{1-6}$ alkoxyl, $C_{2-3}$ alkynyl, $C_{2-3}$ alkenyl, aryl, heteroaryl, cycloalkyl, $M_1OH$, $M_1NHAc$, $M_1OAc$, $M_1OBz$,

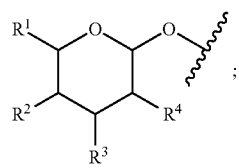

or any two of $R^1$, $R^2$, $R^3$, $R^4$ are linked to form a ring, and each of the substituents in the ring is independently selected from one or more of H, D, $C_{1-4}$ alkyl, $C_{1-4}$ alkoxyl, $C_{2-3}$ alkynyl, $C_{2-3}$ alkenyl, phenyl, heteroaryl, halogen, cyano, carboxy or ester group; $M_1$ is selected from 0-1 methylene;

$R^5$ is selected from H, phenyl, $C_{1-8}$ alkyl.

Further, the structure of said glycosyl donor is selected from:

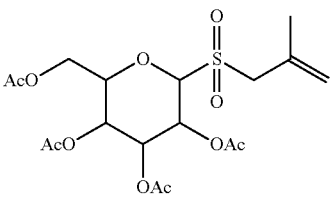

-continued

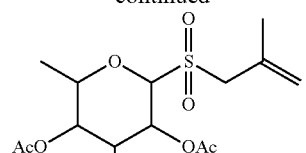

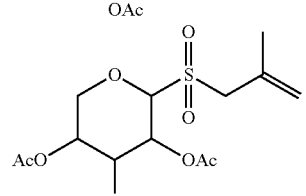

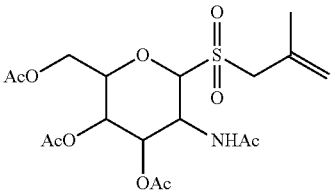

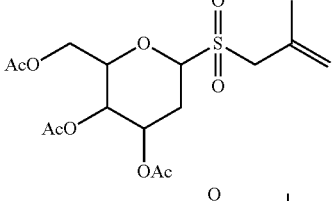

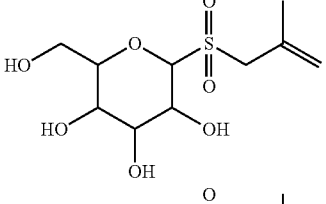

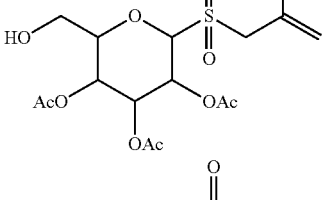

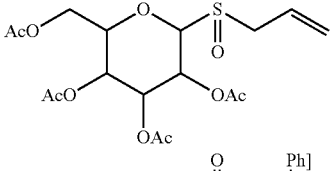

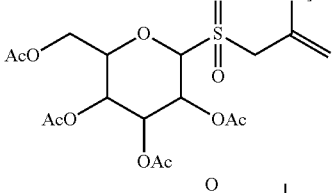

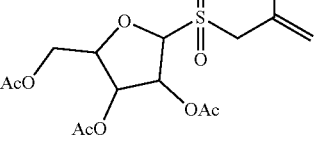

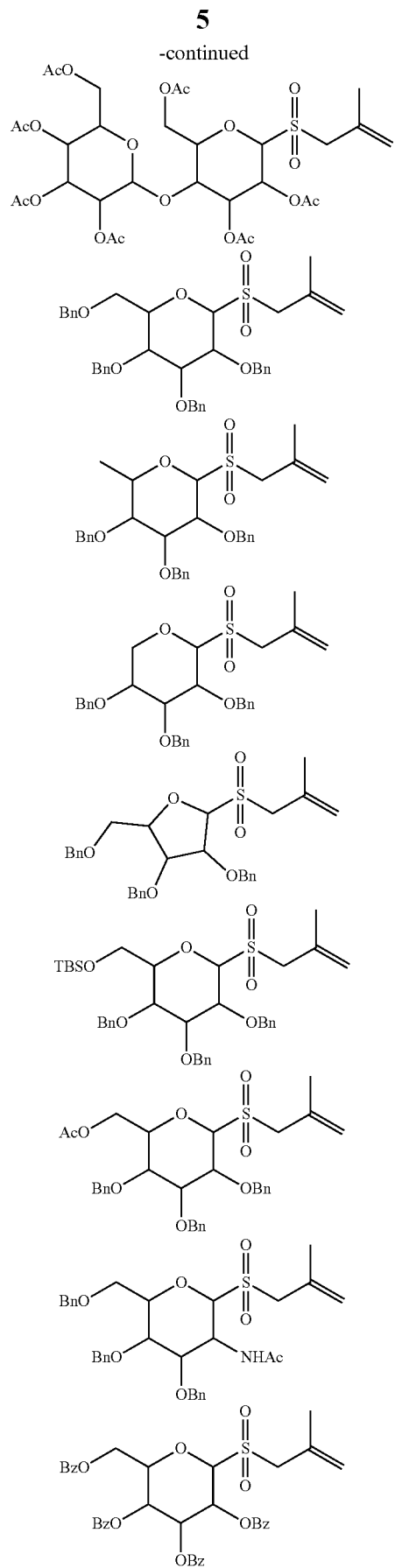
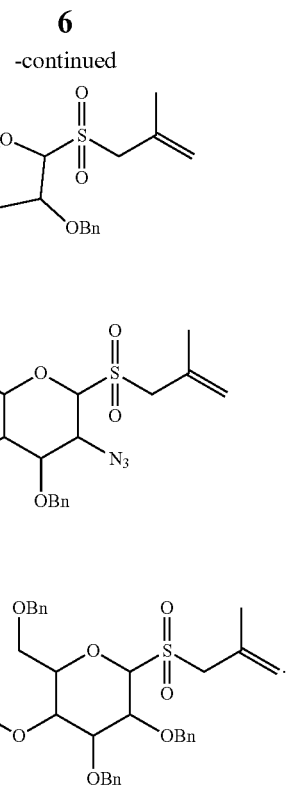
Further, the structure of said glycosyl donor is selected from:

3-5 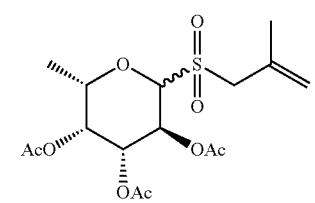
3-6 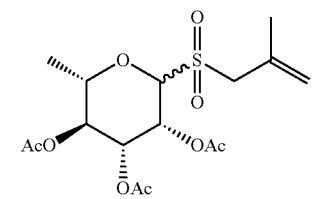
3-7 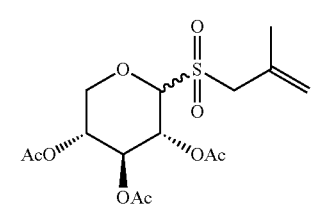
3-8 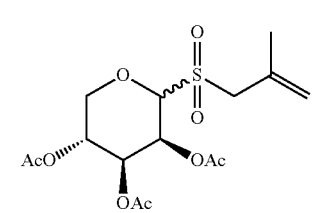
3-9 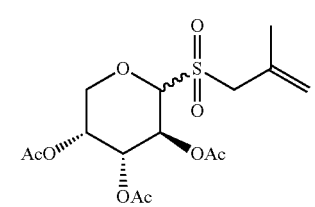
3-10 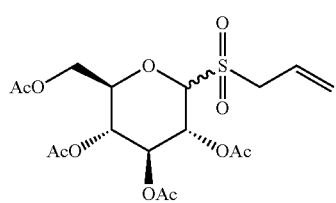
3-11 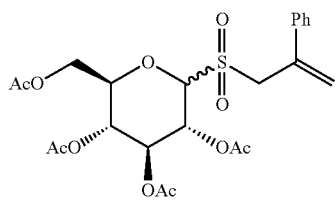
3-12 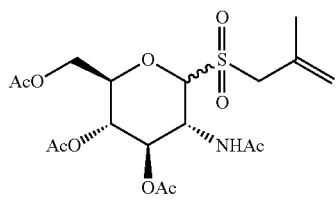
3-13 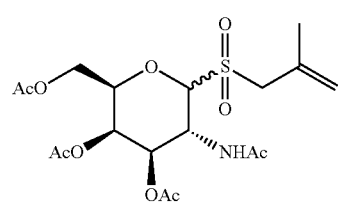
3-14 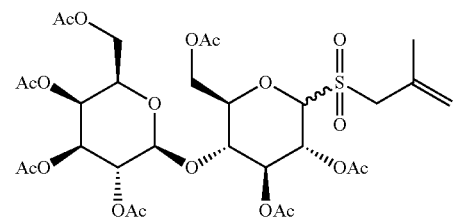
3-15 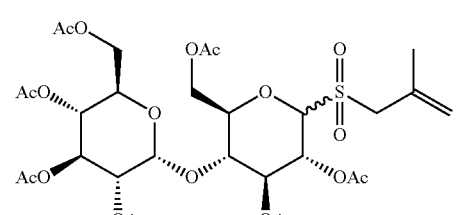
3-16 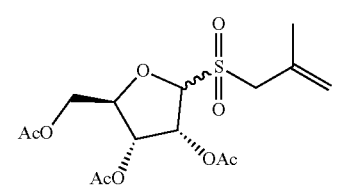
3-17 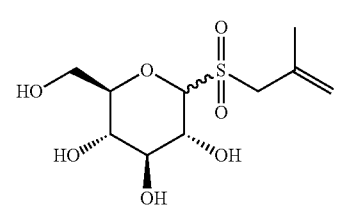
3-18 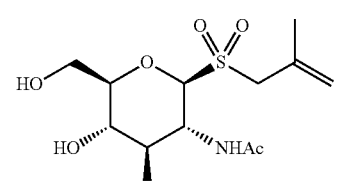
3-19 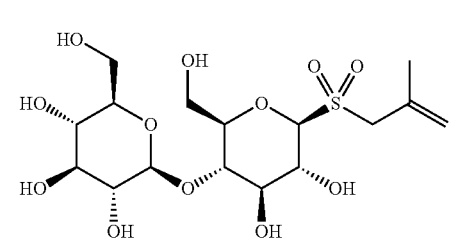

-continued 3-20

3-21

3-22

3-23

3-24

3-25

3-26

3-27

-continued 3-28

3-29

3-30

3-31

3-32

3-33

3-34

3-35

-continued

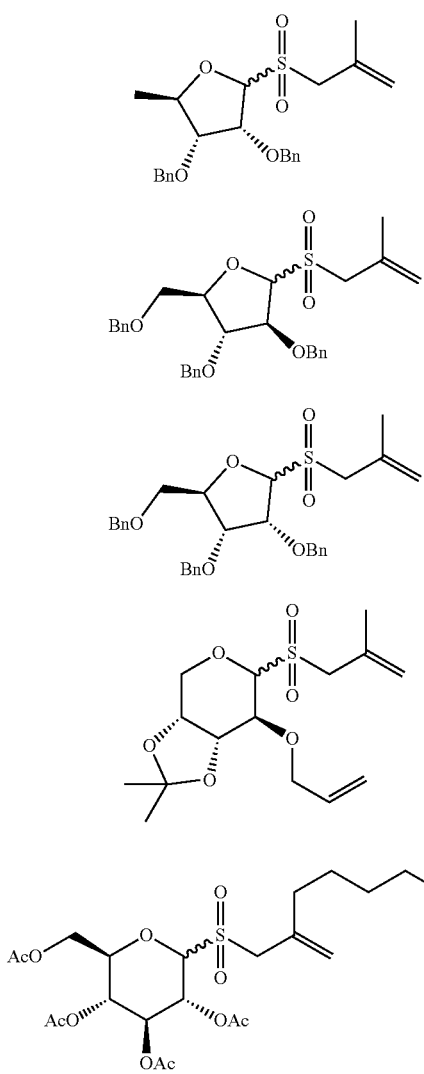

3-36

3-37

3-38

3-39

3-40

Wherein,

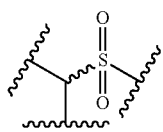 [SMILES: *C(*)S(*)(=O)=O]

represents

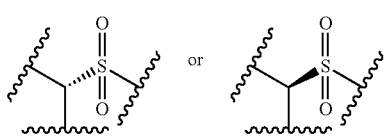

or a mixture of the two in any ratio.

The present invention further provides a S-glycoside compound, or a salt thereof, or a stereoisomer thereof, or an optical isomer thereof, and the S-glycoside compound has a structure of formula III:

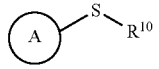

Formula III

Wherein, $R^{10}$ is selected from

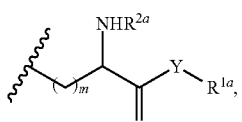

substituted or unsubstituted aryl, substituted or unsubstituted heteroaryl, substituted or unsubstituted alkyl,

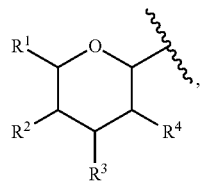

the group obtained by removing a hydrogen from the peptide chain; said substituent is selected from halogen, haloalkyl; m denotes an integer of 1-5;

Y is selected from none, NH or O; each of $R^{1a}$ and $R^{2a}$ is independently selected from the group consisting of H, Boc, Bz, $C_{1-6}$ alkyl, $C_{1-6}$ alkoxyl, aryl, heteroaryl, the group obtained by removing a hydrogen from the peptide chain,

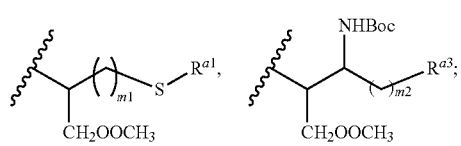

wherein each of $m_1$ and $m_2$ is independently selected from an integer of 0-5; $R^{a1}$ is selected from substituted or unsubstituted $C_{1-6}$ alkyl; said substituent is selected from halogen and hydroxyl; $R^{a3}$ is selected from substituted or unsubstituted $C_{1-6}$ alkyl, aryl, heteroaryl; said substituent is selected from halogen and hydroxyl;

Ring A is selected from

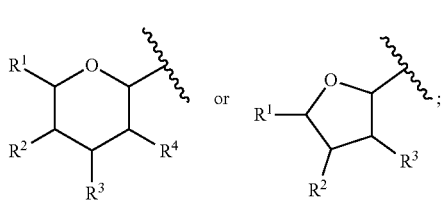

$R^1$, $R^2$, $R^3$, and $R^4$ are as described above.

Further, said S-glycoside compound has the structures of formulae III-1, III-2, III-3 or III-4:

Formula III-1
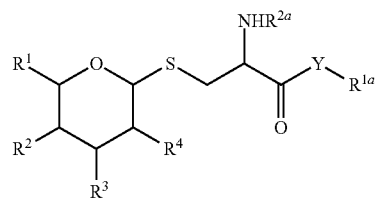

Formula III-2
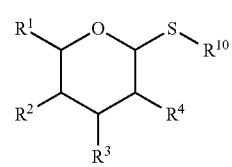

Formula III-3
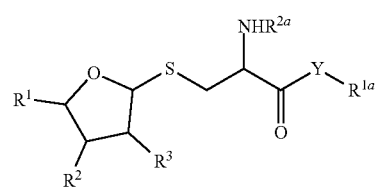

Formula III-4
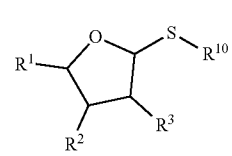

In Formula III-1 and Formula III-3: When Y is selected from O, $R^{1a}$ is selected from methyl, $R^{2a}$ is selected from Bz, H,

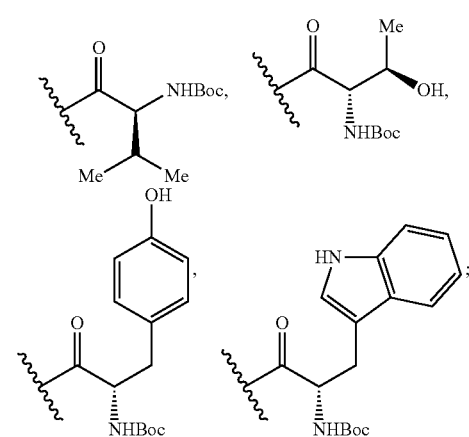

when Y is selected from NH, $R^{1a}$ is selected from

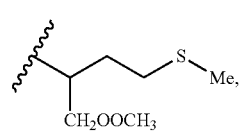

$R^{2a}$ is selected from Boc;
when Y is selected from none, $R^{1a}$ is selected from methoxyl, $R^{2a}$ is selected from Bz;
In Formula III-2 and Formula III-4: $R^{10}$ is selected from substituted or unsubstituted benzene ring, substituted or unsubstituted aza-aromatic ring, methyl,

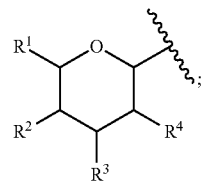

said substituent is selected from halogen, haloalkyl;
In Formulae III-1, III-2, III-3, and III-4: $R_1$, $R_2$, $R_3$, and $R_4$ are as described above.
Further, the structure of said S-glycoside compound is selected from:

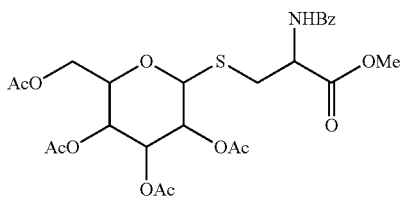

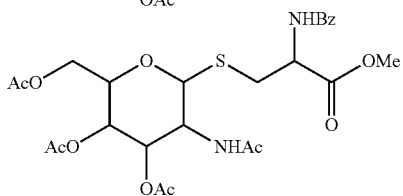

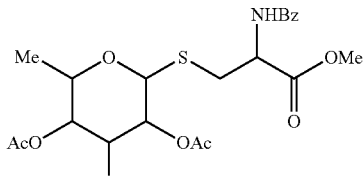

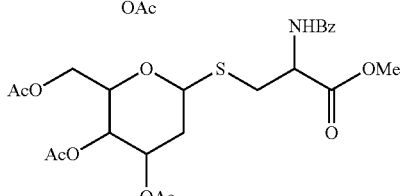

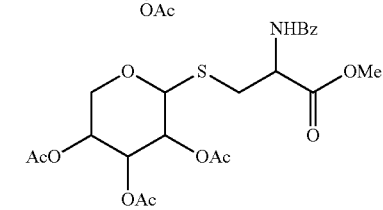

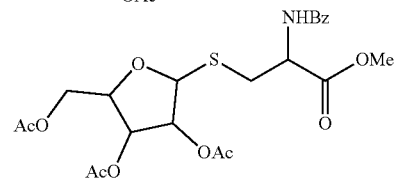

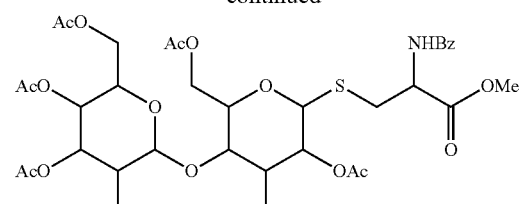
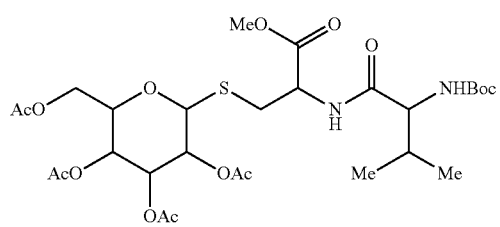
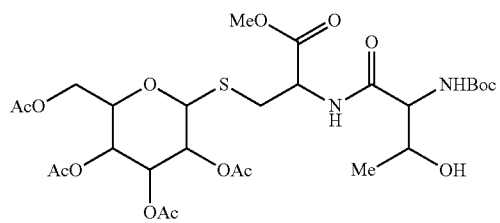
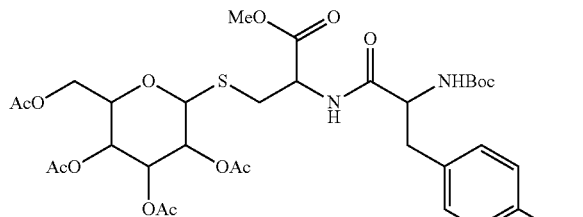
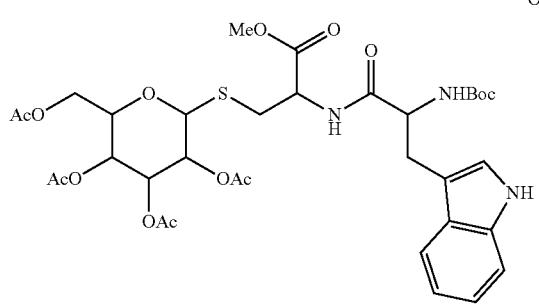
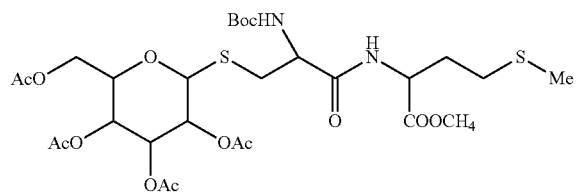
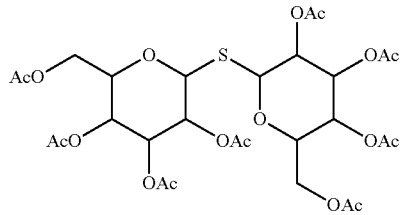
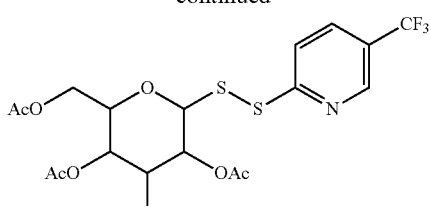
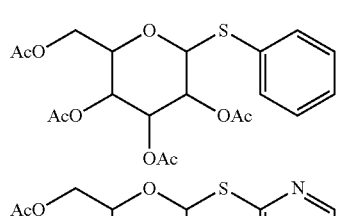
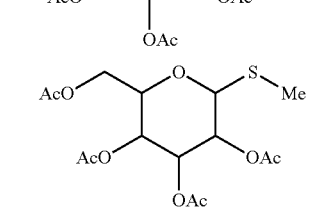
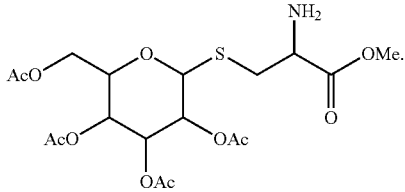
Further, the structure of said S-glycoside compound is selected from:
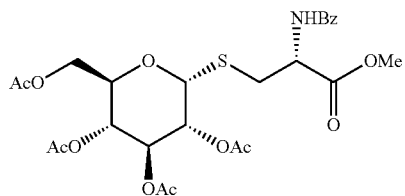
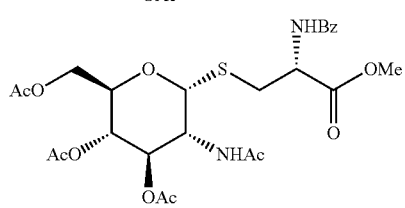
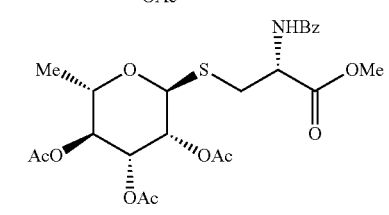

17
-continued
18
-continued
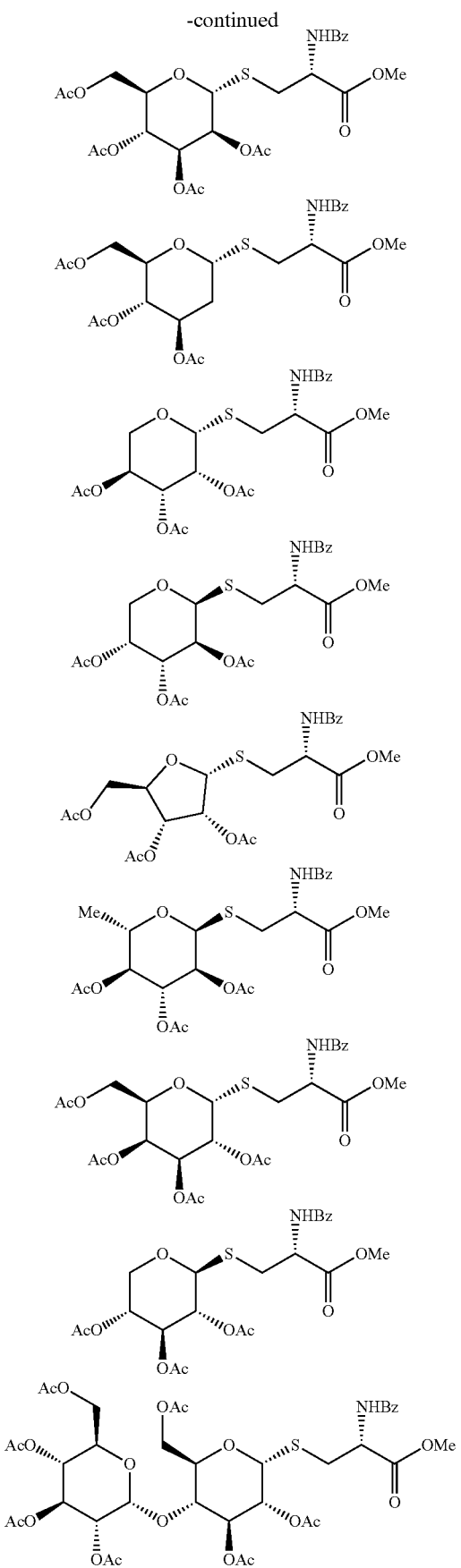
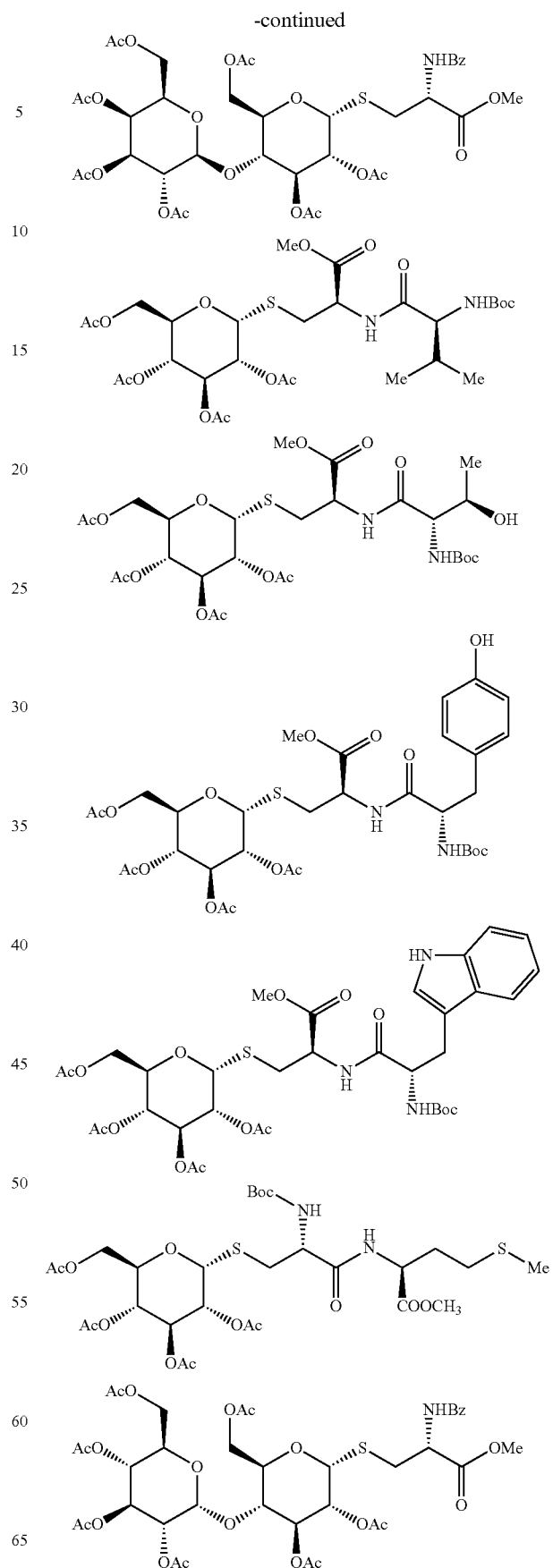

-continued

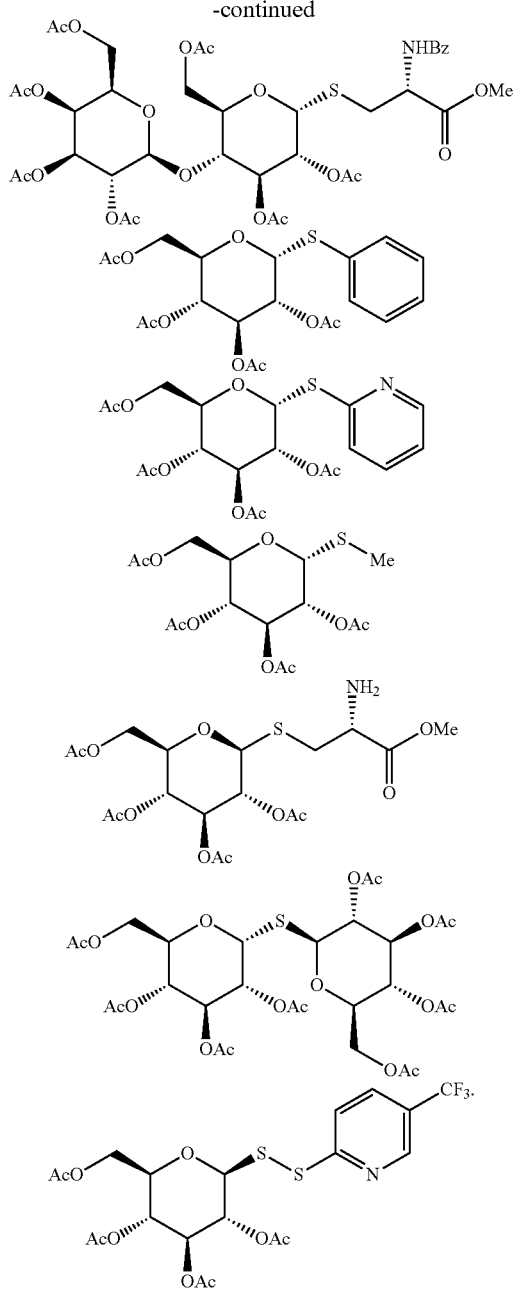

The present invention further provides a O-glycoside compound, or a salt thereof, or a stereoisomer thereof, or an optical isomer thereof, and the O-glycoside compound has a structure of formula IV:

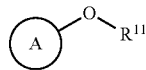

Formula IV

Wherein, $R^{11}$ is selected from $L_0R^{12}$ or $COL_0R^2$; $L_0$ is selected from 0-3 alkylene, $R^{12}$ is selected from substituted or unsubstituted $C_{1-6}$ alkyl, substituted or unsubstituted ring; said substituent is one or more, and each of said substituents is independently selected from CN, $C_{1-6}$ alkoxyl, $C_{1-6}$ alkoxyl, $L_1$(COOEt)NHBz, OH, $NH_2$, NHAc, OAc, OBz, OBn; $L_1$ is selected from 0-3 alkylene; ring A is selected from

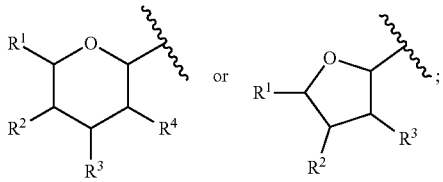

$R^1$, $R^2$, $R^3$, and $R^4$ are as described above.

Further, the O-glycoside compound has a structure of formulae IV-1, IV-2, IV-3, IV-4, IV-5, and IV-6:

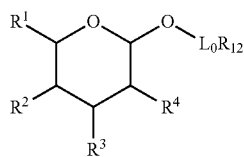

Formulas IV-1

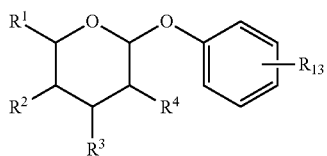

Formulas IV-2

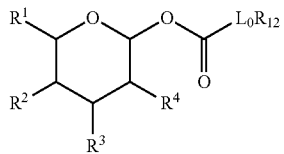

Formulas IV-3

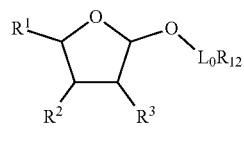

Formulas IV-4

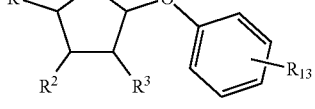

Formulas IV-5

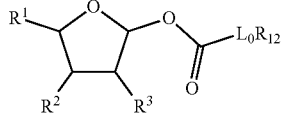

Formulas IV-6

Wherein, $R_1$, $R_2$, $R_3$, and $R_4$ are as described above; $L_0$ is selected from 0-2 alkylene; $R^{12}$ is selected from substituted or unsubstituted $C_{1-3}$ alkyl, substituted or unsubstituted saturated monocyclic carbocyclic ring, saturated monocyclic heterocyclic ring, bridged ring, spiro ring, fused ring; for said substituents, each of $R_{13}$ is independently selected from CN, $C_{1-3}$ alkoxyl, $C_{1-3}$ alkoxyl, $L_1$(COOEt)NHBz, OH, $NH_2$, NHAc, OAc, OBz, OBn; $L_1$ is selected from 0-1 alkylene.

Further, the structure of said O-glycoside compound is selected from:
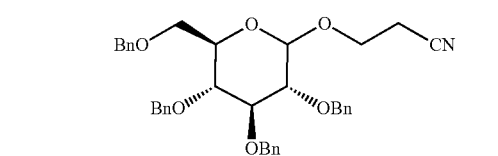
O-1
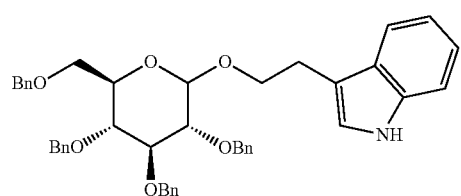
O-2
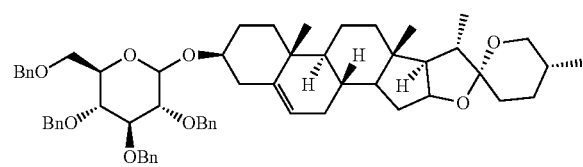
O-3
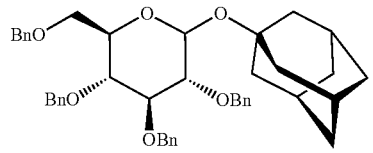
O-4
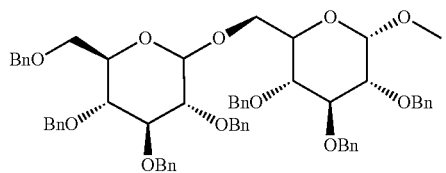
O-5
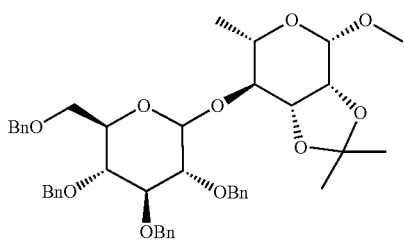
O-6
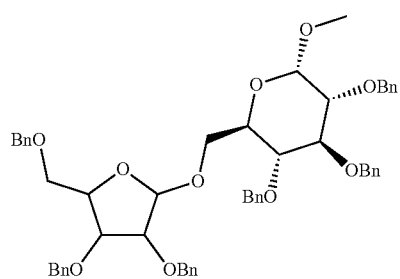
O-7
-continued
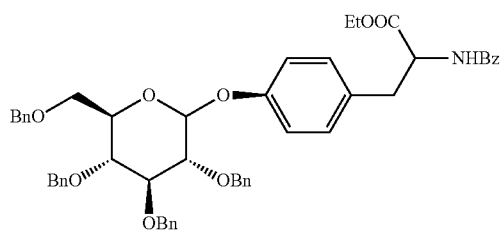
O-8
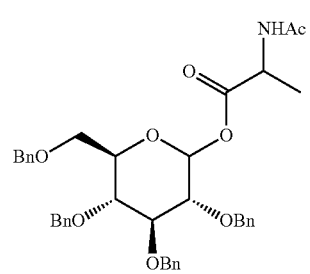
O-9
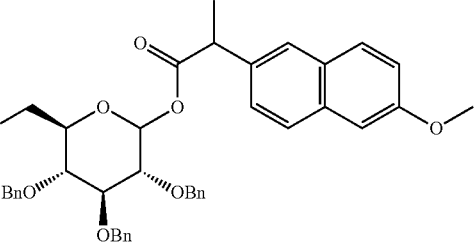
O-10
The present invention further provides a C-glycoside compound, or a salt thereof, or a stereoisomer thereof, or an optical isomer thereof, and said C-glycoside compound has a structure of formula V:
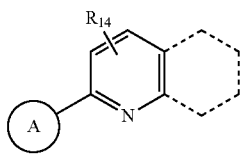
Formula V
Wherein, ring A is selected from
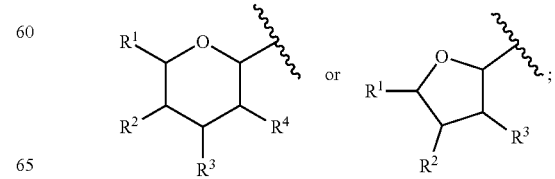

$R^1$, $R^2$, $R^3$, and $R^4$ are as described above;

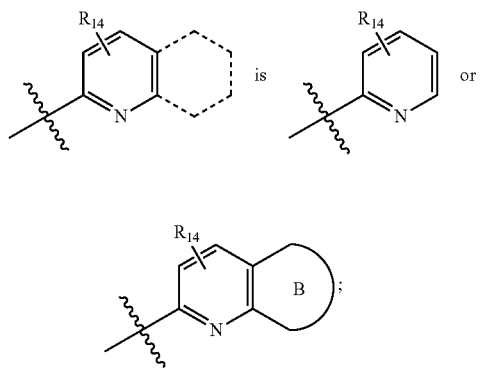

ring B is saturated or unsaturated ring, and preferably is benzene ring;

$R_{14}$ is selected from H, CN, halogenated or unhalogenated $C_{1-3}$ alkyl, halogenated or unhalogenated $C_{1-3}$ alkoxyl, $COOR_{15}$; $R_{15}$ is selected from $C_{1-3}$ alkyl.

Further, said C-glycoside compound has a structure of formulae V-1, V-2, V-3, and V-4:

Formulas V-1

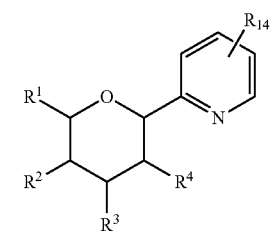

Formulas V-2

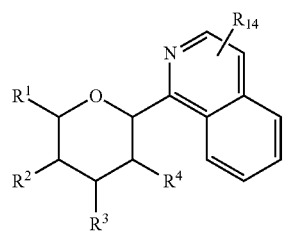

Formulas V-3

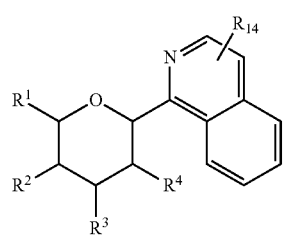

Formulas V-4

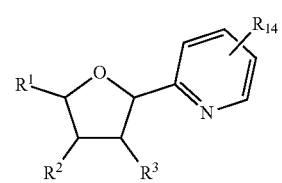

Wherein, $R_1$, $R_2$, $R_3$, $R_4$, and $R_{14}$ are as described above.

Further, the structure of said C-glycoside compound is selected from:

C-1

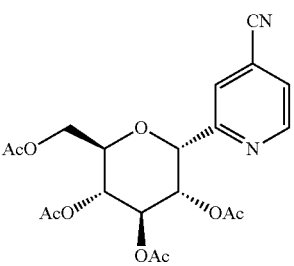

C-2

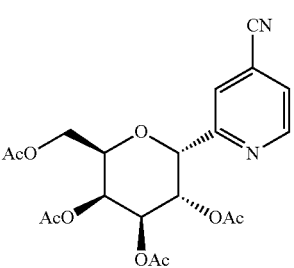

C-3

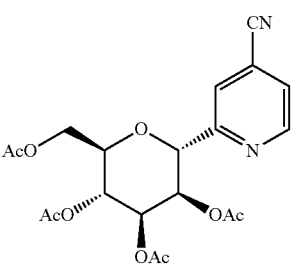

C-4

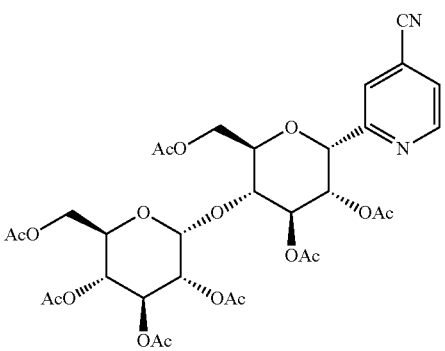

C-5

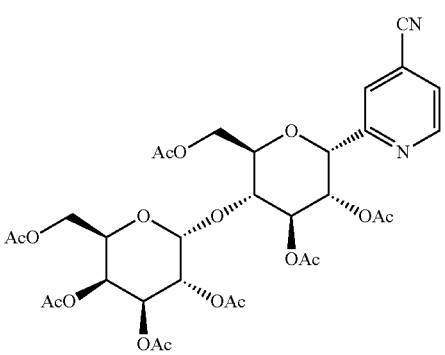

-continued

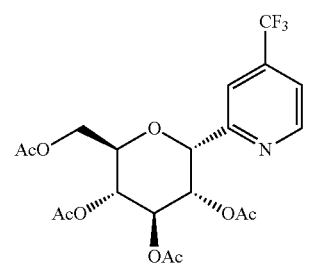
C-6

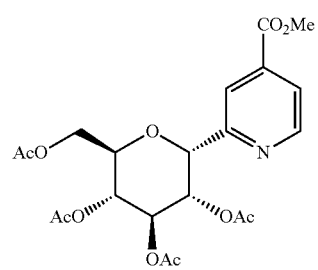
C-7

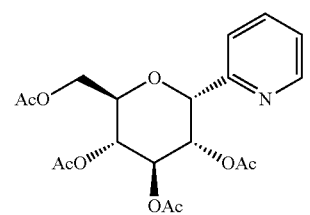
C-8

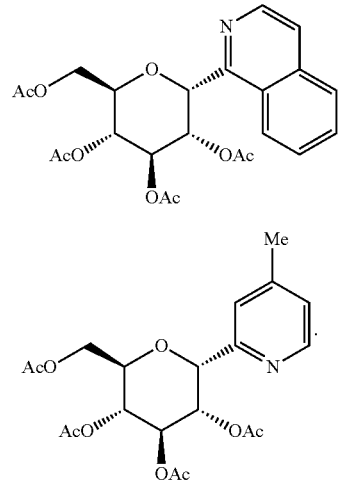
C-9

C-10

(3) Compound Y4 reacts with mCPBA to obtain glycosyl donor;

Wherein, the structure of starting material Y1 is

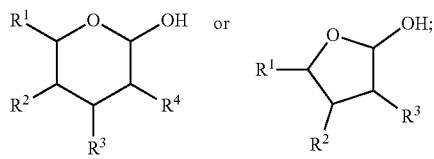

the structure of compound Y2 is

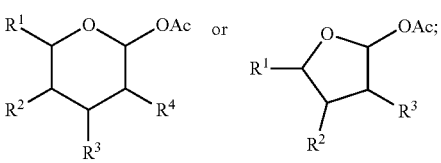

the structure of compound Y3 is

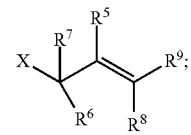

the structure of compound Y4 is

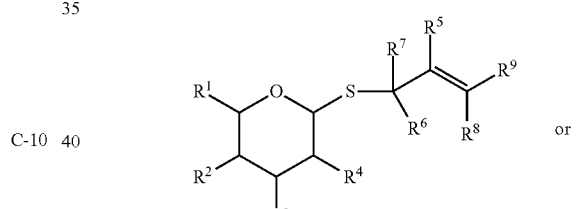

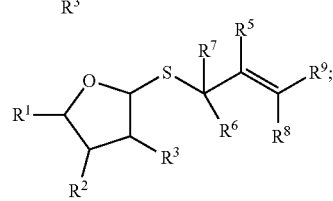

X is selected from halogen, and preferably is bromine;

$R^1$, $R^2$, $R^3$, $R^4$, $R^5$, $R^6$, $R^7$, $R^8$, and $R^9$ are as described above.

Further, in step (1), the molar ratio of the acetic anhydride to the hydroxyl group in the starting material Y1 is (0.8-1.5):1; the reaction is carried out under the action of triethylamine and DMAP; the reaction temperature is room temperature; the reaction solvent is dichloromethane;

In step (2), the molar ratio of compound Y2, thiourea, and compound Y3 is 1:(1.5-4.5):(1.2-2); the reaction temperature before adding compound Y3 is heating reflux, and the reaction time is (2-6) hours; the reaction before adding Y3 is carried out under the action of boron trifluoride diethyl etherate; the reaction temperature after adding Y3 is heating reflux, and the reaction time The present invention further provides the use of the glycosyl donor mentioned above in the preparation of S-glycoside compound, O-glycoside compound, and C-glycoside compound; preferably, said S-glycoside compound is as described above, and/or said O-glycoside compound is as described above, and/or said C-glycoside compound is as described above.

The present invention further provides a method for preparation of the glycosyl donor mentioned above, and the method comprises the following steps:

(1) The starting material Y1 is reacted with acetic anhydride, to obtain compound Y2;

(2) Compound Y2 is first reacted with thiourea, and then compound Y3 is added for further reaction, to obtain compound Y4;

is (4-8) hours; the reaction after adding Y3 is carried out under the action of triethyl amine; the reaction solvent is acetonitrile;

In step (3), the molar ratio of compound Y4 to mCPBA is 1:(1.5-4.5); the reaction time is 1-3 hours; the reaction solvent is dichloromethane;

Preferably,

In step (1), the molar ratio of the acetic anhydride to the hydroxyl group in the starting material Y1 is 1.2:1;

In step (2), the molar ratio of compound Y2, thiourea, and compound Y3 is 1:3:1.5; the reaction time before adding compound Y3 is 4 h; the reaction time after adding Y3 is 6 h;

In step (3), the molar ratio of compound Y4 to mCPBA is 1:2.5; the reaction temperature is room temperature, and the reaction time is 2 h.

The present invention further provides a method for preparing the S-glycosyl compound mentioned above, and the method includes:

The glycosyl donor mentioned above reacts with a glycosyl acceptor, to obtain S-glycosyl compound;

Wherein, the structure of said glycosyl acceptor is

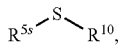

$R^{5s}$ is selected from

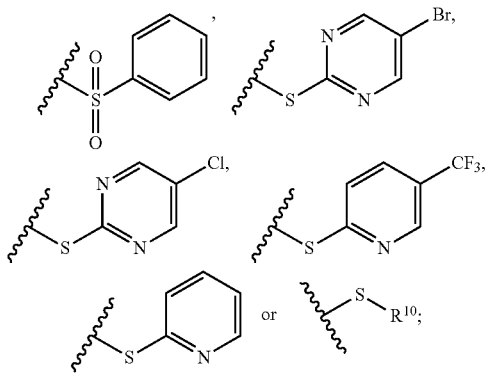

$R^{10}$ is as described above.

Further, said $R^{5s}$ is selected from

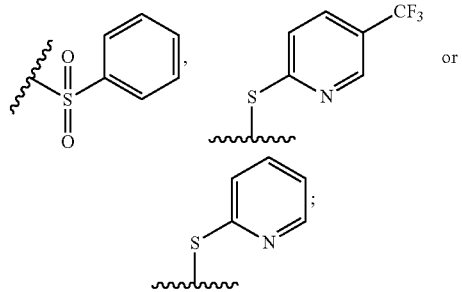

$R^{10}$ is as described above.

The molar ratio of the glycosyl donor to the glycosyl acceptor is 1:(1.1-2.5), and preferably is 1:(1.2-2);

The reaction is carried out under the irradiation of a blue LED in a nitrogen atmosphere;

The temperature of the reaction is 20-45° C., preferably from room temperature to 45° C.; the reaction time is 1.5-5 h, preferably 2-4 h;

The reaction is carried out under the action of a photosensitizer, which is selected from

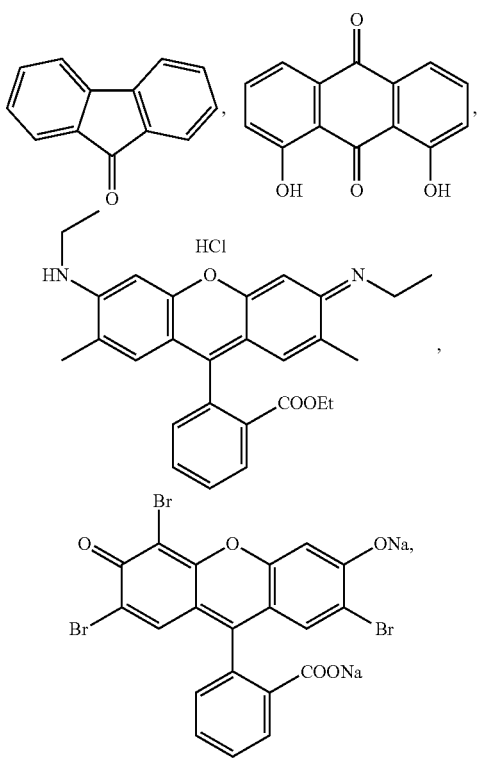

Ir[dF(CF$_3$)(ppy)$_2$](dtbbpy)PF$_6$, and preferably is

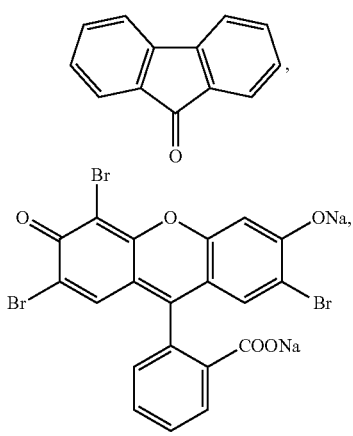

Ir[dF(CF$_3$)(ppy)$_2$](dtbbpy)PF$_6$, and more preferably is Ir[dF(CF$_3$)(ppy)$_2$](dtbbpy)PF$_6$;

The reaction solvent is selected from water or the mixed solution of water with one or more of 1,2-DCE, DMSO, EtOAc, glyme, 1,4-dioxane, THF, MeOH, DMF, MeCN in any ratio.

The present invention further provides a method for preparing the O-glycosyl compound mentioned above, and the method includes:

The glycosyl donor mentioned above reacts with a glycosyl acceptor, to obtain O-glycosyl compound; wherein, the structure of said glycosyl acceptor is HO—R$^{11}$, and R$^{11}$ is as described above;

Preferably, the molar ratio of the glycosyl donor to the glycosyl acceptor is (1.2-2.0):1.0, and preferably is 1.5:1.0; and/or, the reaction is performed in the presence of perfluorobutyl iodide, diammonium hydrogen phosphate, and triphenylphosphine oxide, and the molar ratio of the glycosyl acceptor to perfluorobutyl iodide, diammonium hydrogen phosphate, triphenylphosphine oxide is 1.0:(3-7):(3-7):(0.1-0.5), and preferably is 1.0:5.0:5.0:0.3; and/or the reaction solvent is an organic solvent, and preferably is methyl t-butyl ether; and/or, the reaction is carried out under the irradiation of a blue LED in a nitrogen atmosphere; and/or, the reaction temperature is 20-45° C., and preferably is room temperature; the reaction time is 12-36 h, and preferably is 24 h.

The present invention further provides a method for preparing the C-glycosyl compound mentioned above, and the method includes:

The glycosyl donor mentioned above reacts with a glycosyl acceptor, to obtain C-glycosyl compound;

Wherein, the structure of said glycosyl acceptor is

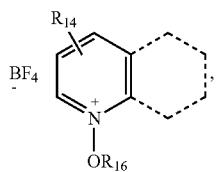

R$_{16}$ is selected from C$_{1-3}$ alkyl, and preferably is methyl;

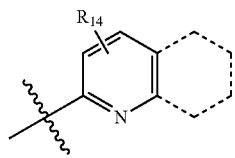

is

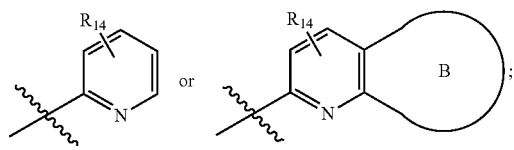

ring B is saturated or unsaturated ring, and preferably is benzene ring; R$_{14}$ is selected from H, CN, halogenated or unhalogenated C$_{1-3}$ alkyl, halogenated or unhalogenated C$_{1-3}$ alkoxyl, COOR$_{15}$; R$_{15}$ is selected from C$_{1-3}$ alkyl;

Preferably, the molar ratio of the glycosyl donor to the glycosyl acceptor is 1:(1.5-3.0), and preferably is 1:2.0; the reaction is performed under the action of a photosensitizer and an initiator, and said photosensitizer is preferably Eosin Y, while said initiator is preferably sodium trifluoromethylsulfinate; the molar ratio of the glycosyl donor and the photosensitizer and the initiator is 1:(0.01-0.03):(0.1-0.3), and preferably is 1:0.025: 0.2; the reaction is performed under the irradiation of a blue LED in a nitrogen atmosphere; and/or, the reaction temperature is 20-45° C., and preferably is room temperature; the reaction time is 5-12 h, and preferably is 8 h.

Glycosyl donor denotes the starting material containing glycosidic bonds or the anomeric carbon that participates in the reaction when synthesizing glycosides; while the other starting material reacting with glycosyl donor is called glycosyl acceptor.

The glycosyl donor of the present invention can be prepared by any one of routes 1-4 in the synthetic examples of the glycosyl donor, or can also be prepared by other methods.

Experiments confirm that the glycosyl donor provided by the present invention has a novel structure including a special substructure of allylsulfone, and can be prepared by a simple method. The present invention further uses the above-mentioned glycosyl donor as a starting material, and by a free radical reaction, O-glycoside, S-glycoside, and C-glycoside compounds are prepared, most of which have a special α configuration. The preparative method is simple, the reaction conditions are mild, and the reaction has a high yield, that all indicate promising application prospects.

For the definition of term used in the present invention: unless otherwise specified, the initial definition provided for the group or the term herein is applicable to those in the whole specification; for terms not specifically defined herein, according to the disclosure content and the context, the term should have the meaning commonly given by those skilled in the field.

The minimum and maximum values of carbon atom content in the hydrocarbon group are indicated by a prefix, for example, the prefix C$_{a-b}$ alkyl indicates any alkyl group having "a"-"b" carbon atoms. For example, C$_{1-8}$ alkyl means a straight or branched alkyl containing 1-8 carbon atoms. Similarly, C$_{1-8}$ alkoxy means a straight or branched alkoxy containing 1-8 carbon atoms.

In the present invention, Ac represents an acetyl group, and the structure is

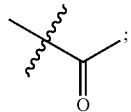 [SMILES: *C(C)=O]

Ph represents phenyl, and the structure is

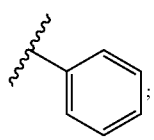 [SMILES: *c1ccccc1]

Bz represents benzoyl, and the structure is

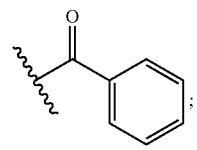 [SMILES: *C(=O)c1ccccc1]

Boc represents t-butoxycarbonyl, and the structure is

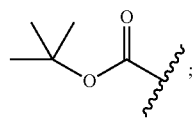 [SMILES: *C(=O)OC(C)(C)C]

Me represents methyl.

In the present invention, a peptide chain denotes a chain structure containing multiple peptide bonds formed by multiple amino acids linked to each other.

"mCPBA" is m-chloro-peroxybenzoic acid.

In the present invention, aryl means an aromatic group; Ar represents aryl. "Aryls" denote all-carbon monocyclic or fused polycyclic (i.e. ring sharing adjacent carbon atom pairs) groups with conjugated π electron system, such as phenyl and naphthyl. Said aromatic ring can be fused to other cyclic groups (including saturated and unsaturated rings), but can not contain hetero atoms such as nitrogen, oxygen, or sulfur. At the same time, the point connecting with the parent must be on the carbon in the ring having the conjugated n electron system. Aryls can be substituted or unsubstituted.

"Heteroaryls" denote the heteroaromatic group containing one or more heteroatoms, and said heteroatom includes O, S, or N. For example, furanyl, thienyl, pyridyl, pyrazolyl, pyrrolyl, N-alkylpyrrolyl, pyrimidinyl, pyrazinyl, imidazolyl, tetrazolyl, etc. The heteroaromatic ring can be fused to aryls, heterocyclic group or cycloalkyl ring, in which the ring connected with the parent structure is heteroaromatic ring. Heteroaryls can be optionally substituted or unsubstituted.

"Cycloalkyls" denote saturated or unsaturated cyclic hydrocarbon substituents; cyclic hydrocarbon can have one or more rings. "Saturated cycloalkyls" denote saturated cyclic alkyls.

"Heterocyclic group" denotes a saturated or unsaturated cyclic hydrocarbon substituent; the cyclic hydrocarbon may be monocyclic or polycyclic, and carry at least one heteroatom in the ring (including but not limited to O, S or N). "Saturated heterocyclyl" refers to a saturated heterocyclic group.

"Salts" are acid and/or basic salts formed by compounds with inorganic and/or organic acids and/or bases, also including amphoteric salts (inner salts), and quaternary ammonium salts, such as alkylammonium salts. These salts can be directly obtained in the final isolation and purification of the compound, and can also be obtained by appropriately mixing the compound with a certain amount of acid or base (e.g., equivalent). These salts may form a precipitate in the solution and be collected by filtration, or recovered after evaporation of the solvent, or prepared by freeze-drying after reacting in an aqueous medium.

The salt in the present invention may be hydrochloride, sulfate, citrate, benzenesulfonate, hydrobromide, hydrofluoride, phosphate, acetate, propionate, succinate, oxalate, malate, succinate, fumarate, maleate, tartrate or trifluoroacetate of the compound.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

The starting materials and equipment used in the specific examples of the present invention are all known products, which are obtained by purchasing commercially available products.

Synthesis of Glycosyl Donor:

The following synthetic route is used to prepare the synthetic glycosyl donor of the present invention:

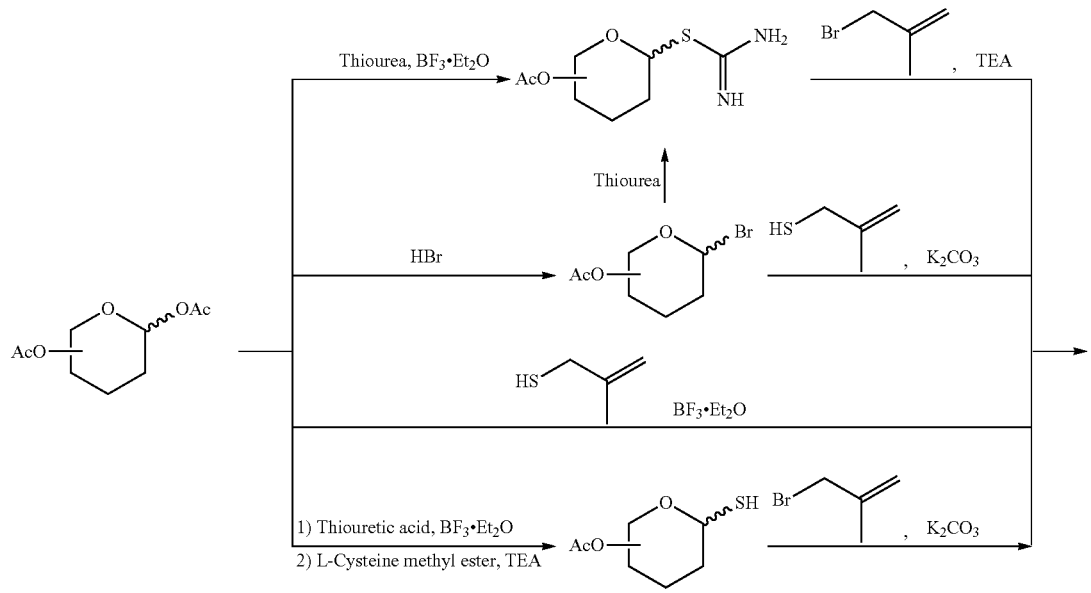

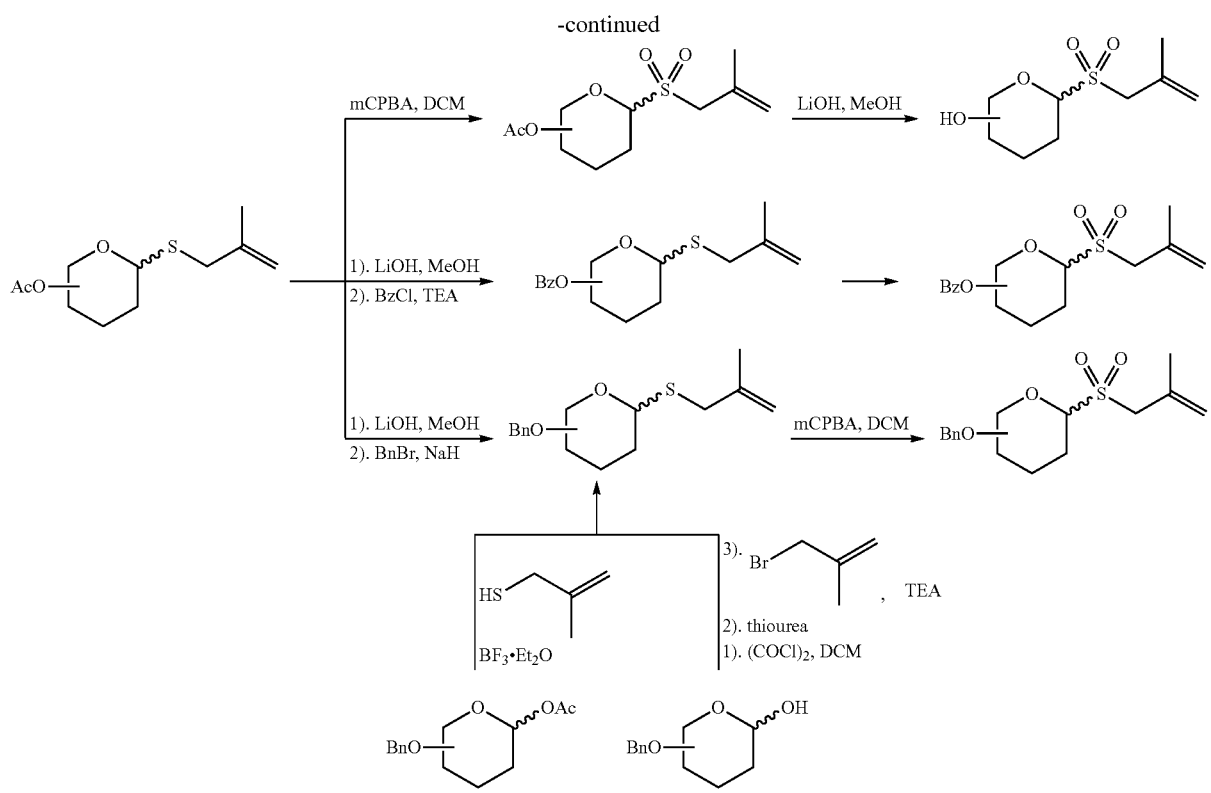
The following is a synthetic example of the allylsulfone glycosyl donor according to the present invention.
1. Synthetic Route 1
1) The Scheme of Synthetic Route
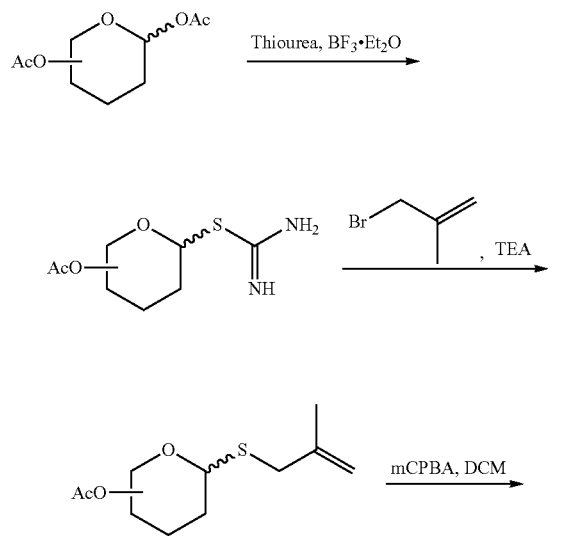
2) Details of Synthetic Procedures (Taking Compound 3-1 as an Example)
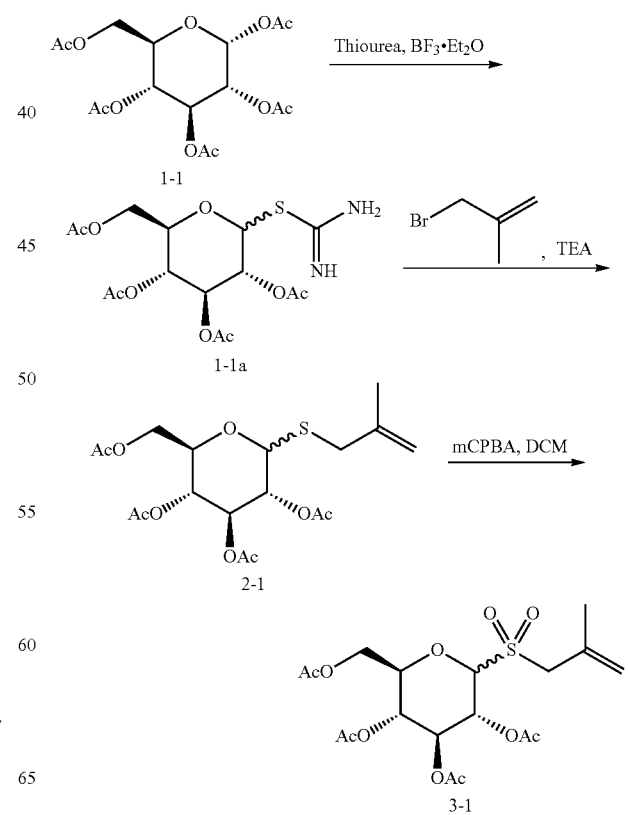

a) Peracetyl-protected substrate 1-1 (10 mmol) was dissolved in acetonitrile (40 mL) at room temperature, to which were added thiourea (1.5 equiv.) and boron trifluoride diethyl etherate (3 equiv.), and the reaction solution was refluxed for 4 h, then cooled to room temperature. 3-Bromo-2-methylpropylene (1.5 equiv.) and triethylamine (3 equiv.) were added, and the resultant solution was refluxed for 6 h, followed by cooling to room temperature. Acetonitrile was rotatory evaporated under reduced pressure, and the residue was dissolved in dichloromethane. The solution was washed with saturated brine, extracted with dichloromethane, dried over anhydrous $Na_2SO_4$, filtered, concentrated, and separated by column chromatography (silica gel, 300-400 meshes) to obtain the corresponding thioether intermediate 2-1.

b) Compound 2-1 obtained in the previous step was dissolved in dichloromethane in an ice bath, to which was slowly added m-CPBA (2.5 equiv.), and then the mixture was warmed to room temperature and reacted for 2 h. The reaction solution was filtered, and the solid was washed with dichloromethane. The filtrate was washed once with saturated $Na_2S_2O_3$ solution, and washed twice with saturated $Na_2CO_3$ solution. The resultant solution was extracted with dichloromethane, dried over anhydrous $Na_2SO_4$, filtered, concentrated, and separated by column chromatography (300-400 mesh silica gel), to obtain the corresponding product, i.e. compound 3-1, with a purity of greater than 90% and a total yield of 75%.

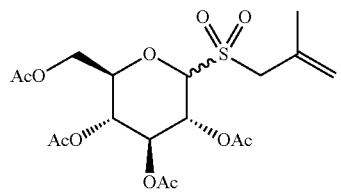

3-1

Its structure was characterized by the following:
$^1$H NMR (400 MHz, Chloroform-d) δ 5.53 (t, J=9.6 Hz, 1H), 5.31 (t, J=9.3 Hz, 1H), 5.27 (t, J=1.6 Hz, 1H), 5.20 (d, J=1.4 Hz, 1H), 5.10 (t, J=9.8 Hz, 1H), 4.58 (d, J=9.9 Hz, 1H), 4.31-4.17 (m, 2H), 3.98 (d, J=13.6 Hz, 1H), 3.80 (ddd, J=10.1, 5.1, 2.7 Hz, 1H), 3.66 (d, J=13.6 Hz, 1H), 2.09 (s, 3H), 2.05 (s, 3H), 2.04 (s, 3H), 2.03 (s, 3H), 1.98 (s, 3H).

Compounds 3-2-3-11 were synthesized by the same route as that of compound 3-1 mentioned above, and the structure and characterization data are as follows:

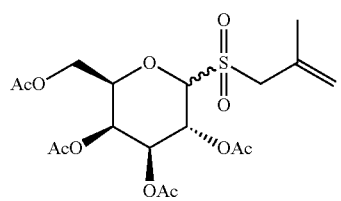

3-2

Purity >90%; total yield 62%; $^1$H NMR (400 MHz, chloroform-d) (α:β=1:6) (β-isomer) δ 5.72 (t, J=9.9 Hz, 1H), 5.47 (d, J=3.3 Hz, 1H), 5.27 (s, 1H), 5.20 (s, 1H), 5.15 (dd, J=10.1, 3.3 Hz, 1H), 4.57 (d, J=9.8 Hz, 1H), 4.19 (m, J=5.4 Hz, 2H), 4.07 (t, J=6.3 Hz, 1H), 3.99 (d, J=13.6 Hz, 1H), 3.69 (d, J=13.6 Hz, 1H), 2.19 (s, 3H), 2.06 (s, 6H), 2.00 (s, 3H), 1.98 (s, 3H).

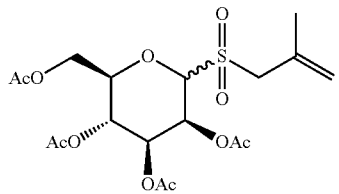

3-3

Purity >90%; total yield 62%; $^1$H NMR (400 MHz, chloroform-d) δ 5.94 (dd, J=3.8, 2.1 Hz, 1H), 5.59 (dd, J=9.2, 3.6 Hz, 1H), 5.29 (t, J=9.7 Hz, 1H), 5.27-5.24 (m, 1H), 5.21-5.18 (m, 1H), 4.99 (d, J=2.1 Hz, 1H), 4.70 (ddd, J=9.9, 5.8, 2.4 Hz, 1H), 4.27 (dd, J=12.5, 5.8 Hz, 1H), 4.17 (dd, J=12.5, 2.5 Hz, 1H), 4.00 (d, J=13.9 Hz, 1H), 3.67 (d, J=13.9 Hz, 1H), 2.17 (s, 3H), 2.11 (s, 3H), 2.07 (s, 3H), 2.01 (s, 3H), 1.98 (s, 3H).

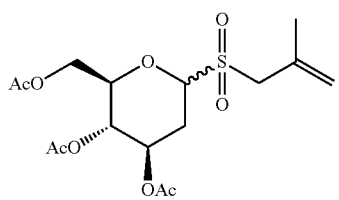

3-4

Purity >90%; total yield 51%; $^1$H NMR (400 MHz, chloroform-d) (α:β=2:1) (α-isomer) δ 5.47 (ddd, J=9.7, 7.7, 5.1 Hz, 1H), 5.25 (s, 1H), 5.18 (s, 1H), 5.05-4.94 (m, 2H), 4.68-4.58 (m, 1H), 4.27 (dd, J=12.5, 5.6 Hz, 1H), 4.15 (dd, J=12.4, 2.5 Hz, 1H), 3.98 (d, J=13.8 Hz, 1H), 3.65 (d, J=13.8 Hz, 1H), 2.82 (ddd, J=14.8, 5.2, 3.4 Hz, 1H), 2.18-2.11 (m, 1H), 2.10 (s, 3H), 2.06 (s, 3H), 2.05 (s, 3H), 1.98 (d, J=1.4 Hz, 3H).

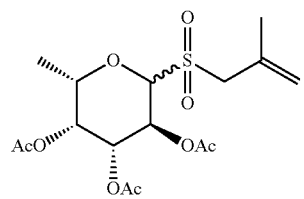

3-5

Purity >90%; total yield 35%; $^1$H NMR (400 MHz, chloroform-d) δ 5.68 (t, J=9.9 Hz, 1H), 5.31 (dd, J=3.4, 1.1 Hz, 1H), 5.27 (t, J=1.5 Hz, 1H), 5.15 (s, 1H), 5.12 (dd, J=10.0, 3.4 Hz, 1H), 4.47 (d, J=9.9 Hz, 1H), 3.96-3.93 (m, 1H), 3.92 (d, J=0.9 Hz, 1H), 3.73 (d, J=13.5 Hz, 1H), 2.20 (s, 3H), 2.06 (s, 3H), 2.00 (s, 3H), 1.98 (s, 3H), 1.28 (d, J=6.4 Hz, 3H).

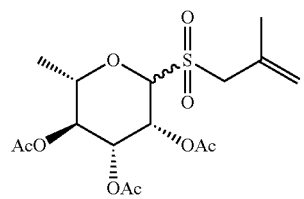

3-6

Purity >90%; total yield 58%; ¹H NMR (400 MHz, chloroform-d) δ 5.93 (dd, J=3.7, 2.0 Hz, 1H), 5.53 (dd, J=9.4, 3.7 Hz, 1H), 5.25 (p, J=1.5 Hz, 1H), 5.17 (s, 1H), 5.10 (t, J=9.5 Hz, 1H), 4.94 (d, J=2.0 Hz, 1H), 4.55 (dq, J=9.6, 6.2 Hz, 1H), 3.97 (d, J=13.9 Hz, 1H), 3.66 (d, J=13.9 Hz, 1H), 2.16 (s, 3H), 2.06 (s, 3H), 2.00 (s, 3H), 1.98 (s, 3H), 1.29 (d, J=6.2 Hz, 3H).

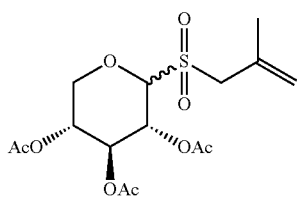
3-7

Purity >90%; total yield 63%; ¹H NMR (400 MHz, chloroform-d) δ 5.51 (t, J=9.1 Hz, 1H), 5.30 (t, J=8.9 Hz, 1H), 5.26 (t, J=1.5 Hz, 1H), 5.13 (s, 1H), 5.02 (td, J=9.0, 5.3 Hz, 1H), 4.54 (d, J=9.2 Hz, 1H), 4.39 (dd, J=11.6, 5.3 Hz, 1H), 3.91 (d, J=13.4 Hz, 1H), 3.69 (d, J=13.4 Hz, 1H), 3.47 (dd, J=11.6, 9.1 Hz, 1H), 2.10-2.00 (m, 9H), 1.97 (s, 3H).

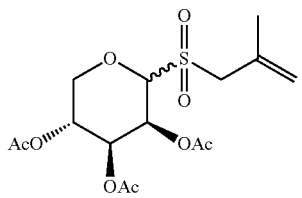
3-8

Purity >90%; total yield 56%; ¹H NMR (400 MHz, chloroform-d) δ 5.75 (dd, J=7.3, 3.4 Hz, 1H), 5.49 (dd, J=5.8, 3.5 Hz, 1H), 5.26 (p, J=1.5 Hz, 1H), 5.16 (s, 1H), 5.01 (ddd, J=5.9, 4.3, 3.0 Hz, 1H), 4.76 (d, J=7.3 Hz, 1H), 4.17 (dd, J=12.4, 4.4 Hz, 1H), 4.01 (dd, J=12.4, 3.0 Hz, 1H), 3.94 (d, J=13.6 Hz, 1H), 3.69 (d, J=13.6 Hz, 1H), 2.14 (s, 1H), 2.12 (s, 3H), 2.09 (s, 3H), 1.98 (s, 3H).

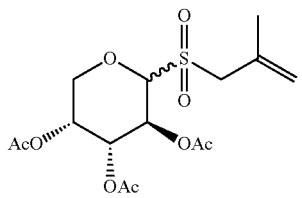
3-9

Purity >90%; total yield 33%; ¹H NMR (400 MHz, chloroform-d) δ 5.73 (t, J=9.4 Hz, 1H), 5.35 (tt, J=2.7, 1.5 Hz, 1H), 5.27 (t, J=1.5 Hz, 1H), 5.22-5.10 (m, 1H), 4.47 (d, J=9.3 Hz, 1H), 4.24 (dd, J=12.9, 2.6 Hz, 1H), 3.92 (d, J=13.4 Hz, 1H), 3.80 (dd, J=13.0, 1.5 Hz, 1H), 3.77-3.73 (d, J=13.4 Hz, 1H), 2.18 (s, 3H), 2.08 (s, 3H), 2.04 (s, 3H), 1.98 (s, 3H).

The synthetic procedures of compound 3-10 are the same as that of compound 3-1, except that 3-bromo-2-methylpropene was substituted with 3-bromopropene in the first step, with a purity of >90% and a total yield of 75%,

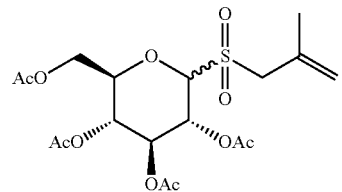
3-10

¹H NMR (400 MHz, chloroform-d) δ 5.99-5.79 (m, 1H), 5.58-5.47 (m, 3H), 5.31 (t, J=9.3 Hz, 1H), 5.10 (t, J=9.8 Hz, 1H), 4.56 (d, J=9.9 Hz, 1H), 4.34-4.16 (m, 2H), 3.98 (dd, J=13.9, 8.4 Hz, 1H), 3.83-3.73 (m, 2H), 2.10 (s, 3H), 2.05 (s, 3H), 2.05 (s, 3H), 2.03 (s, 3H).

The synthetic procedures of compound 3-11 are the same as that of compound 3-1, and only 3-bromo-2-methylpropene was substituted with 3-bromo-2-phenylpropene in the first step, with a purity of >90% and a total yield of 71%,

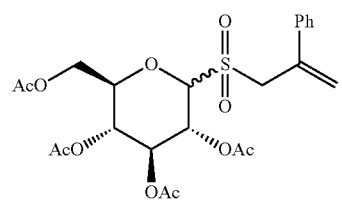
3-11

¹H NMR (400 MHz, chloroform-d) δ 7.50-7.46 (m, 2H), 7.43-7.36 (m, 3H), 5.77 (s, 1H), 5.60 (s, 1H), 5.50 (t, J=9.6 Hz, 1H), 5.16 (t, J=9.3 Hz, 1H), 5.03 (t, J=9.8 Hz, 1H), 4.51 (d, J=14.2 Hz, 1H), 4.17 (d, J=9.9 Hz, 1H), 4.10-4.03 (m, 3H), 3.29 (dt, J=10.1, 3.5 Hz, 1H), 2.10 (s, 3H), 2.02 (s, 3H), 2.01 (s, 3H), 2.00 (s, 3H).

2. Synthetic Route 2

1) Scheme of Synthetic Route

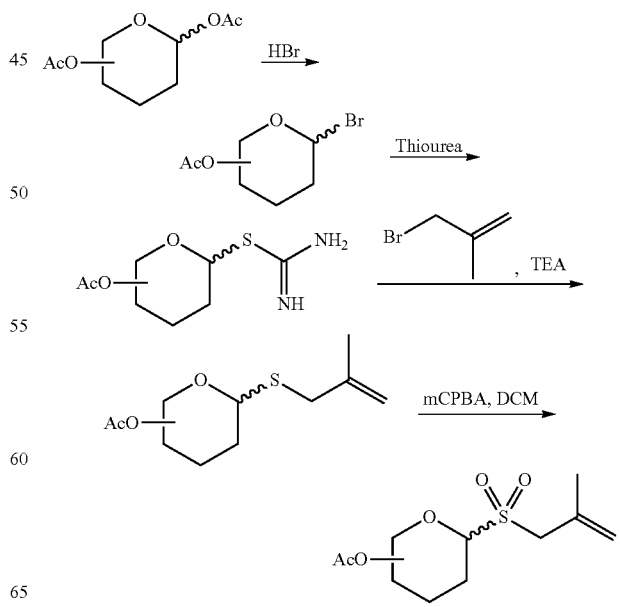

2) Details of Synthetic Procedures (Taking Compound 3-12 as an Example)

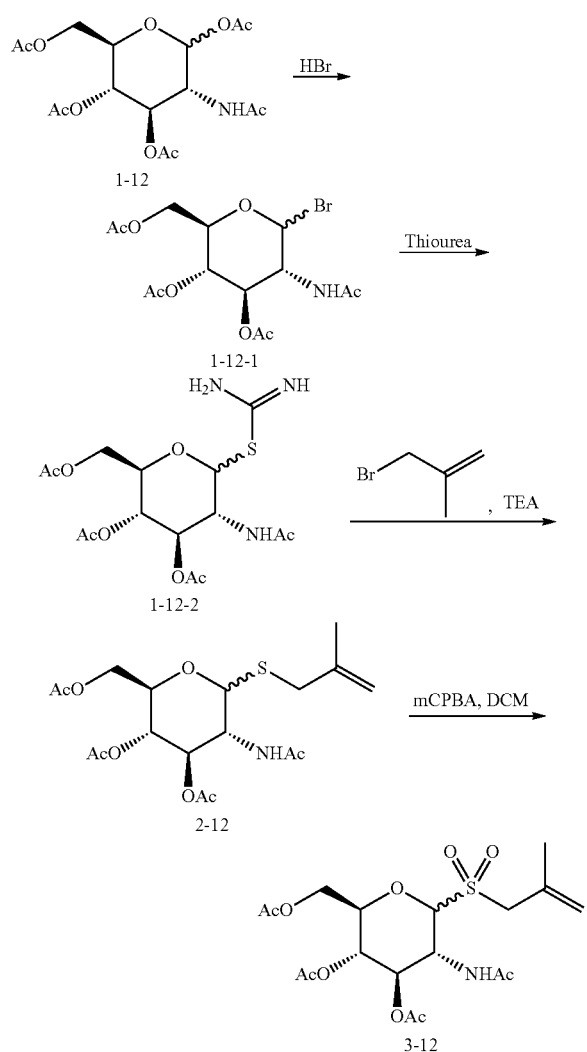

a) At 0° C., peracetyl-protected 2-aminoglucose substrate 1-12 (10 mmol) was dissolved in DCM (30 mL), to which was slowly added the solution of hydrobromic acid in acetic acid (33%, 30 mL) dropwise, and the mixture was stirred for 5 h. Once the starting materials disappeared, the reaction was quenched with ice water, and then the reaction solution was neutralized with the saturated aqueous solution of $K_2CO_3$ in an ice-water bath. The resultant solution was extracted with dichloromethane, and then successively washed with the ice-cold saturated aqueous solution of $NaHCO_3$ and ice-cold saturated brine. The organic phase was dried over anhydrous sodium sulfate, filtered, and the filtrate was rotatory evaporated, to obtain the crude product 1-12-1, that was directly used in the next step without purification;

b) The crude product 1-12-1 and thiourea (1.5 equiv.) were dissolved in acetone (20 mL) and stirred under reflux at 60° C. for 10 min. A large amount of solid was precipitated. After the reaction solution was cooled to room temperature, the solid was collected by suction filtration, which was the intermediate 1-12-2.

c) Intermediate 1-12-2 and anhydrous potassium carbonate (2.0 equiv.) were dissolved in acetone/water (2:1, 20 mL), and then 3-bromo-2-methylpropylene (1.5 equiv.) was added dropwise. The mixture was stirred overnight at room temperature, and the solvent was rotatory evaporated. The reaction solution was extracted with dichloromethane, successively washed with water and saturated brine. The organic phase was dried over anhydrous $Na_2SO_4$ and filtered. The filtrate was rotatory evaporated, and purified by column chromatography to obtain the thioether intermediate 2-12.

d) Compound 2-12 obtained in the previous step was dissolved in dichloromethane in an ice bath, to which was slowly added m-CPBA (2.5 equiv.), and the mixture was warmed to room temperature and reacted for 2 h. The reaction solution was filtered, and the solid was washed with dichloromethane. The filtrate was successively washed once with saturated $Na_2S_2O_3$ solution, and twice with saturated $Na_2CO_3$ solution. The solution was extracted with dichloromethane, dried over anhydrous sodium sulfate, filtered, concentrated, and separated by column chromatography (300-400 mesh silica gel), to obtain the corresponding product compound 3-12, with a purity of greater than 90% and a total yield of 31%.

Its characterization data were as follows:

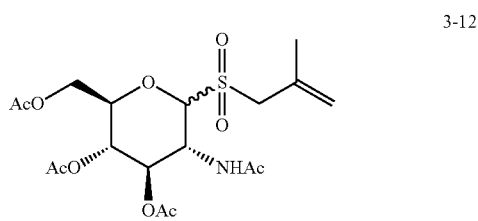 [SMILES: C=C(C)CS(=O)(=O)C1O[C@H](COC(C)=O)[C@@H](OC(C)=O)[C@H](OC(C)=O)[C@H]1NC(C)=O]

3-12

¹H NMR (400 MHz, chloroform-d) δ 6.07 (d, J=7.9 Hz, 1H), 5.72 (t, J=9.7 Hz, 1H), 5.25 (s, 1H), 5.21-5.15 (m, 2H), 5.05 (t, J=9.2 Hz, 1H), 4.25 (dd, J=12.6, 2.5 Hz, 1H), 4.20 (dd, J=12.6, 5.3 Hz, 1H), 4.10-4.03 (m, 1H), 4.00 (d, J=13.6 Hz, 1H), 3.89 (ddd, J=10.3, 5.2, 2.5 Hz, 1H), 3.69 (d, J=13.5 Hz, 1H), 2.09 (s, 3H), 2.05 (d, J=1.6 Hz, 6H), 1.96 (s, 3H), 1.94 (s, 3H).

The synthetic route of compound 3-13 were the same as that of compound 3-12, and the product 3-13 could be obtained by using peracetyl 2-aminogalactose as the starting material. The purity was greater than 90%, and the characterization data were as follows:

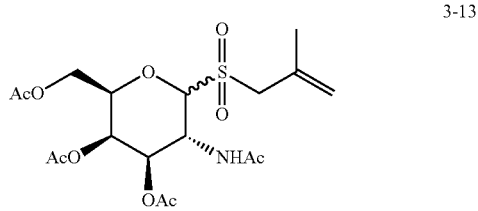 [SMILES: C=C(C)CS(=O)(=O)C1O[C@H](COC(C)=O)[C@H](OC(C)=O)[C@H](OC(C)=O)[C@H]1NC(C)=O]

3-13

¹H NMR (400 MHz, Chloroform-d) δ 6.28 (d, J=8.0 Hz, 1H), 5.72 (dd, J=10.8, 3.3 Hz, 1H), 5.46 (d, J=3.3 Hz, 1H), 5.20 (s, 1H), 5.17 (d, J=10.2 Hz, 1H), 4.25 (m, 1H), 4.22-4.11 (m, 3H), 4.02 (d, J=13.5 Hz, 1H), 3.73 (d, J=13.5 Hz, 1H), 2.18 (s, 3H), 2.05 (s, 3H), 2.01 (s, 3H), 1.96 (s, 3H), 1.94 (s, 3H).

3. Synthetic Route 3

1) Scheme of Synthetic Route

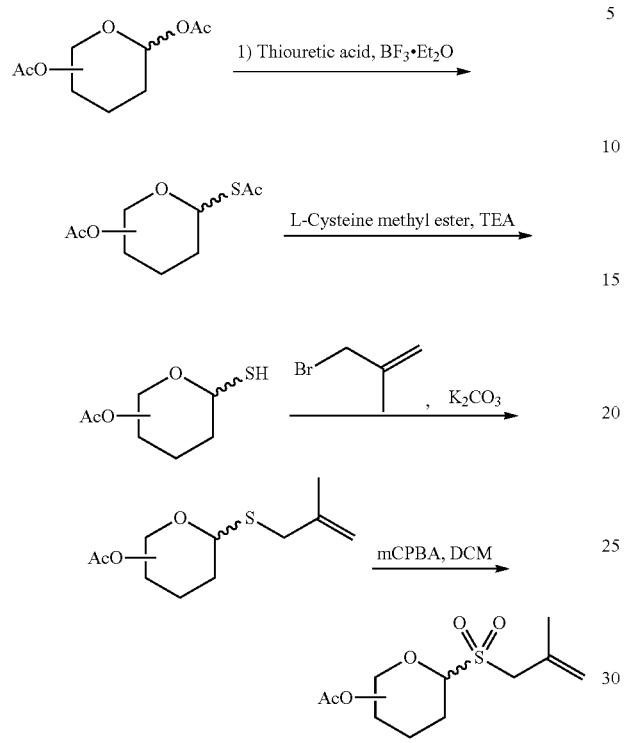

2) Details of Synthetic Procedures (Taking Compound 3-14 as an Example)

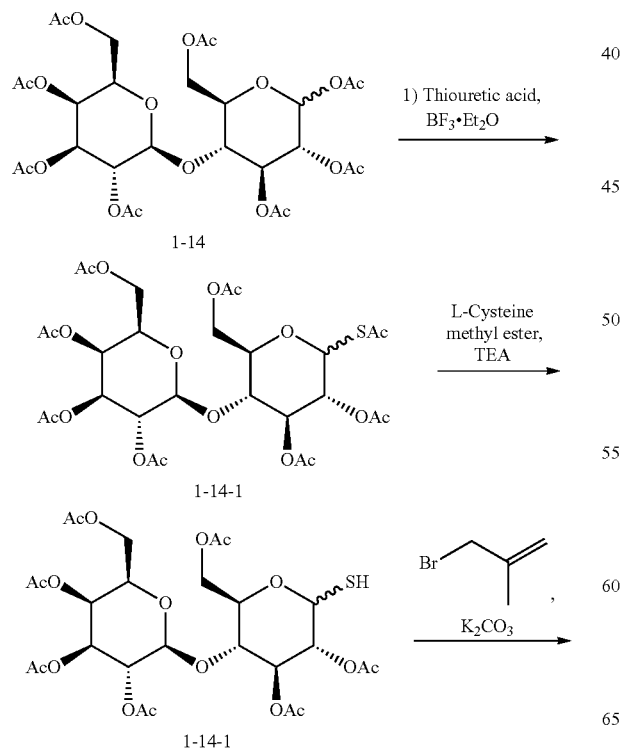

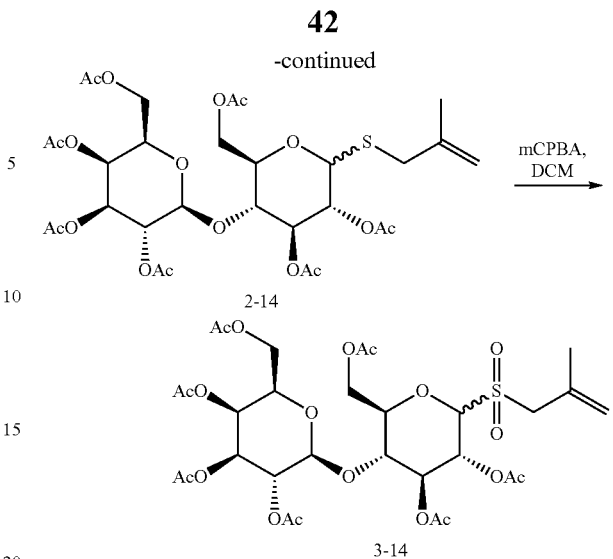

a) At 0° C., compound 1-14 (10 mmol) was dissolved in DCM (30 mL), to which were slowly added thioacetic acid (24 mmol) and boron trifluoride diethyl etherate (30 mmol), and then the mixture was warmed to room temperature and stirred overnight. Once the starting materials disappeared, the reaction was quenched with ice water. The reaction solution was extracted with dichloromethane, and then successively washed with the saturated aqueous solution of $NaHCO_3$ and saturated brine. The organic phase was dried over anhydrous sodium sulfate, and filtered. The filtrate was rotatory evaporated, to obtain the crude product 1-14-1.

b) Intermediate 1-14-1 and cysteine methyl ester hydrochloride (2.05 g, 12 mmol) were dissolved in DMF (10 mL), to which was added triethylamine (1.7 mL, 12 mmol), and the mixture was stirred at room temperature for 8 h. After the disappearance of intermediate 1-14-1 was detected by TLC, the reaction solution was extracted with ethyl acetate, and washed with half-saturated brine. The organic phase was dried with anhydrous sodium sulfate and filtered. The filtrate was rotatory evaporated, and purified by column chromatography to obtain the product Intermediate 1-14-2.

c) Product intermediate 1-14-2 and anhydrous potassium carbonate (2.5 equiv.) were dissolved in acetone/water (2:1, 20 mL), and then 3-bromo-2-methylpropylene (2.5 equiv.) was added dropwise. The mixture was stirred overnight at room temperature, and the solvent was rotatory evaporated. The reaction solution was extracted with dichloromethane, successively washed with water and saturated brine. The organic phase was dried over anhydrous $Na_2SO_4$ and filtered. The filtrate was rotatory evaporated, and purified by column chromatography to obtain the thioether intermediate 2-14.

d) Compound 3-12 obtained in the previous step was dissolved in dichloromethane in an ice bath, to which was slowly added m-CPBA (2.5 equiv.), and the mixture was warmed to room temperature and reacted for 2 h. The reaction solution was filtered, and the solid was washed with dichloromethane. The filtrate successively washed once with saturated $Na_2S_2O_3$ solution, and twice with saturated $Na_2CO_3$ solution. The solution was extracted with dichloromethane, dried over anhydrous sodium sulfate, filtered, concentrated, and separated by column chromatography (300-400 mesh silica gel), to obtain the corresponding product compound 3-14, with a purity of greater than 90% and a total yield of 48%.

Its characterization data were as follows:

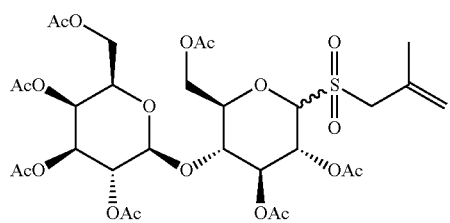

3-14

¹H NMR (400 MHz, Chloroform-d) δ 5.41 (d, J=4.1 Hz, 1H), 5.39-5.32 (m, 3H), 5.27 (t, J=1.5 Hz, 1H), 5.21 (s, 1H), 5.05 (t, J=9.9 Hz, 1H), 4.87 (dd, J=10.6, 4.0 Hz, 1H), 4.73-4.67 (m, 1H), 4.64 (dd, J=12.4, 2.6 Hz, 1H), 4.24 (ddd, J=24.7, 12.4, 4.6 Hz, 2H), 4.08 (dd, J=12.4, 2.3 Hz, 1H), 4.04-3.94 (m, 3H), 3.79 (ddd, J=9.7, 5.1, 2.5 Hz, 1H), 3.59 (d, J=13.7 Hz, 1H), 2.14 (s, 3H), 2.11 (s, 3H), 2.06-2.01 (m, 12H), 2.00 (s, 3H), 1.97 (s, 3H).

The synthetic route of compound 3-15 were the same as that of compound 3-14, and the product 3-15 could be obtained by using peracetyl maltose as the starting material. The purity was greater than 90%, and the characterization data were as follows:

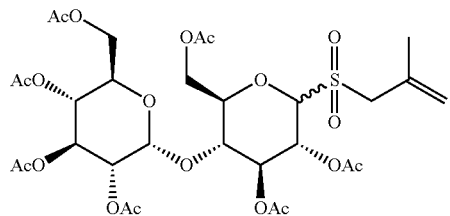

3-15

¹H NMR (400 MHz, Chloroform-d) δ 5.47 (t, J=9.4 Hz, 1H), 5.38-5.35 (m, 1H), 5.32 (d, J=9.0 Hz, 1H), 5.27-5.23 (m, 1H), 5.18 (s, 1H), 5.11 (dd, J=10.5, 7.9 Hz, 1H), 4.98 (dd, J=10.4, 3.4 Hz, 1H), 4.65-4.57 (m, 2H), 4.52 (d, J=7.8 Hz, 1H), 4.18-4.04 (m, 3H), 3.97 (d, J=13.7 Hz, 1H), 3.89 (t, J=6.7 Hz, 1H), 3.82 (t, J=9.4 Hz, 1H), 3.76-3.66 (m, 1H), 3.57 (d, J=13.7 Hz, 1H), 2.15 (s, 3H), 2.12 (s, 3H), 2.07 (s, 3H), 2.06 (s, 3H), 2.05 (s, 3H), 2.04 (s, 3H), 1.97 (s, 6H).

4. Synthetic Route 4

1) Scheme of Synthetic Route

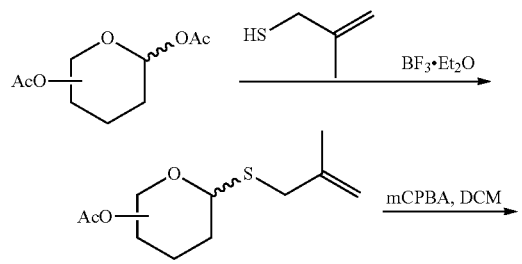

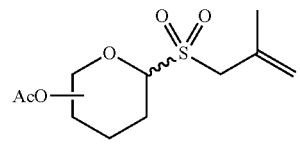

2) Details of Synthetic Procedures (Taking Compound 3-16 as an Example)

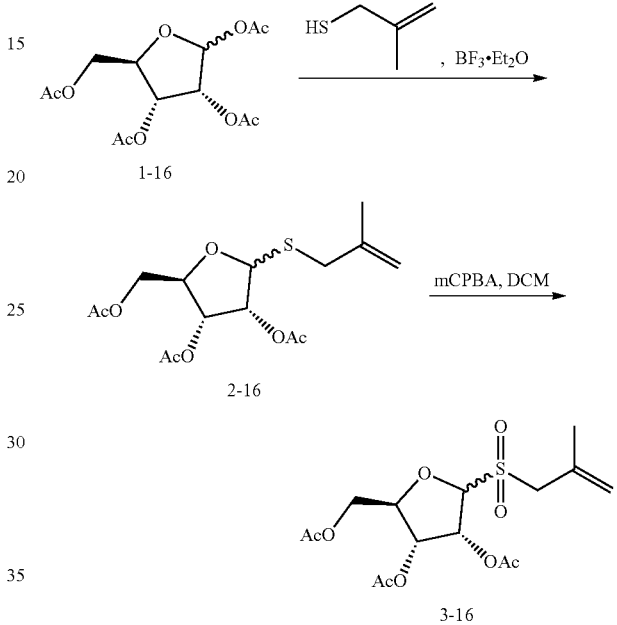

a) At 0° C., compound 1-16 (10 mmol) was dissolved in DCM (30 mL), to which were slowly added 3-mercapto-2-methylpropylene (2.5 equiv.) and boron trifluoride diethyl etherate (30 mmol), and then the mixture was stirred 8 h at 0° C. Once the starting materials disappeared, the reaction was quenched with ice water. The reaction solution was extracted with dichloromethane, and then successively washed with the saturated aqueous solution of NaHCO₃ and saturated brine. The organic phase was dried over anhydrous sodium sulfate and filtered. The filtrate was rotatory evaporated, to obtain the thioether intermediate 2-16.

b) Compound 2-16 obtained in the previous step was dissolved in dichloromethane in an ice bath, to which was slowly added m-CPBA (2.5 equiv.), and the mixture was warmed to room temperature and reacted for 2 h. The reaction solution was filtered, and the solid was washed with dichloromethane. The filtrate was successively washed once with saturated Na₂S₂O₃ solution, and twice with saturated Na₂CO₃ solution. The solution was extracted with dichloromethane, dried over anhydrous sodium sulfate, filtered, concentrated, and separated by column chromatography (300-400 mesh silica gel), to obtain the corresponding product compound 3-16, with a purity of greater than 90% and a total yield of 48%.

Its characterization data were as follows:

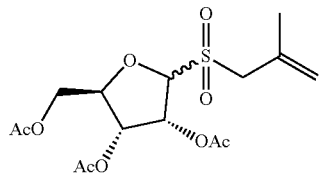

3-16

$^1$H NMR (400 MHz, chloroform-d) δ 5.95-5.85 (m, 1H), 5.68 (t, J=3.2 Hz, 1H), 5.54 (dd, J=8.2, 3.2 Hz, 1H), 5.47 (t, J=6.1 Hz, 1H), 5.30-5.21 (m, 2H), 5.21-5.08 (m, 2H), 5.04 (d, J=2.6 Hz, 1H), 4.74 (m, 2H), 4.50 (dd, J=12.3, 3.4 Hz, 1H), 4.45-4.37 (m, 1H), 4.21 (m, 2H), 3.94 (m, 2H), 3.82 (dd, J=11.2, 9.0 Hz, 1H), 3.68 (d, J=13.5 Hz, 1H), 3.60 (t, J=14.7 Hz, 1H), 2.16 (s, 3H), 2.15 (s, 3H), 2.11 (s, 6H), 2.07 (s, 3H), 2.05 (s, 3H), 1.98 (s, 3H), 1.97 (s, 3H).

Above-mentioned routes 1-4 could be used to synthesize substrates 3-1-3-16, and each example showed the effectiveness of these four synthetic routes.

Synthesis of Compounds 3-17-3-19

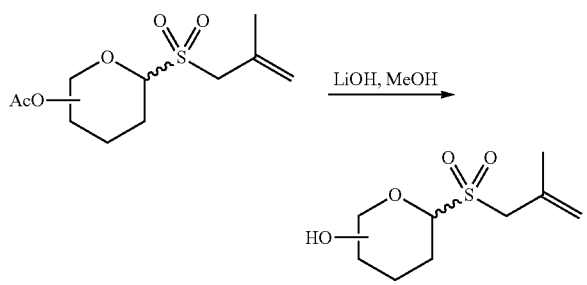

Detailed procedures were as follows:

At room temperature, the peracetyl-protected glycosyl groups synthesized by above 1-4 routes were dissolved in 10 mL methanol, and then the reaction solution was cooled to 0° C., to which was slowly added the solid of lithium hydroxide (0.5 equiv.). After addition, the temperature was still kept at 0° C., and the mixture was allowed to further react 4 h. After completion of the reaction, 2 g silica gel was directly added to the reaction solution, methanol was evaporated under reduced pressure, and the residue was purified by column chromatography, to obtain the target product. Compounds 3-17-3-19 were all prepared according to the above method, and their characterization data were as follows:

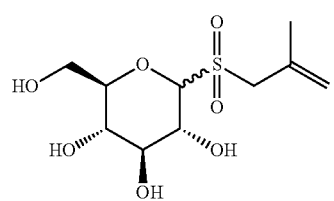

3-17

Purity >90%; $^1$H NMR (400 MHz, Methanol-d$_4$) δ 5.14 (m, 2H), 4.37 (d, J=9.6 Hz, 1H), 4.05 (d, J=13.6 Hz, 1H), 3.81 (dd, J=12.5, 2.1 Hz, 1H), 3.77-3.67 (m, 2H), 3.58 (dd, J=12.5, 6.2 Hz, 1H), 3.36 (t, J=8.9 Hz, 1H), 3.34-3.28 (m, 1H), 3.23-3.18 (t, J=9.4 Hz, 1H), 1.87 (s, 3H).

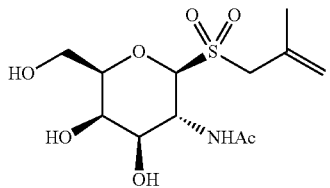

3-18

Purity >90%; $^1$H NMR (400 MHz, deuterium oxide) δ 5.28-5.24 (m, 1H), 5.13 (s, 1H), 4.67 (d, J=10.3 Hz, 1H), 4.37 (t, J=10.3 Hz, 1H), 4.11 (d, J=13.7 Hz, 1H), 3.96 (d, J=3.2 Hz, 1H), 3.91 (d, J=13.7 Hz, 1H), 3.77 (m, 3H), 3.74-3.67 (m, 1H), 1.93 (s, 3H), 1.84 (s, 3H).

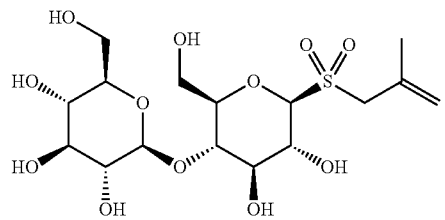

3-19

Purity >90%; $^1$H NMR (400 MHz, deuterium oxide) δ 5.27 (s, 1H), 5.14 (s, 1H), 4.45 (d, J=8.0 Hz, 1H), 4.11 (d, J=14.0 Hz, 1H), 3.98-3.75 (m, 5H), 3.66 (m, 4H), 3.45-3.20 (m, 5H), 1.86 (s, 3H).

Synthesis of Compound 3-20

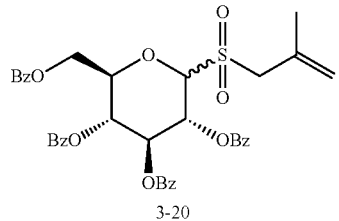

Detailed procedures were as follows:

At room temperature, compound 3-17, benzoyl chloride (6.0 equiv.), triethylamine (6.0 equiv.), and DMAP (0.2 equiv.) were stirred in 20 mL dichloromethane for 12 h at room temperature. After completion of the reaction, the reaction solution was extracted with 50 mL ice-cold dichloromethane. The organic layers were combined, and successively washed with the saturated aqueous solution of citric acid and saturated brine, then dried over anhydrous sodium sulfate, filtered, concentrated under reduced pressure, and purified by column chromatography to obtain the target product 3-20, with a purity of >90%. The characterization data are as follows:

$^1$H NMR (400 MHz, Chloroform-d) δ 8.04-7.99 (m, 1H), 7.97-7.86 (m, 3H), 7.85-7.80 (m, 1H), 7.61-7.27 (m, 10H), 6.07 (t, J=9.5 Hz, 1H), 5.99 (t, J=9.3 Hz, 1H), 5.69 (t, J=9.6 Hz, 1H), 5.25-5.11 (m, 2H), 4.93 (d, J=9.6 Hz, 1H), 4.73 (dd, J=12.5, 2.8 Hz, 1H), 4.53 (dd, J=12.5, 5.7 Hz, 1H), 4.28 (ddd, J=8.6, 5.5, 2.7 Hz, 1H), 4.05 (d, J=13.6 Hz, 1H), 3.71 (d, J=13.6 Hz, 1H), 1.94 (s, 3H).

Synthesis of Compound 3-21

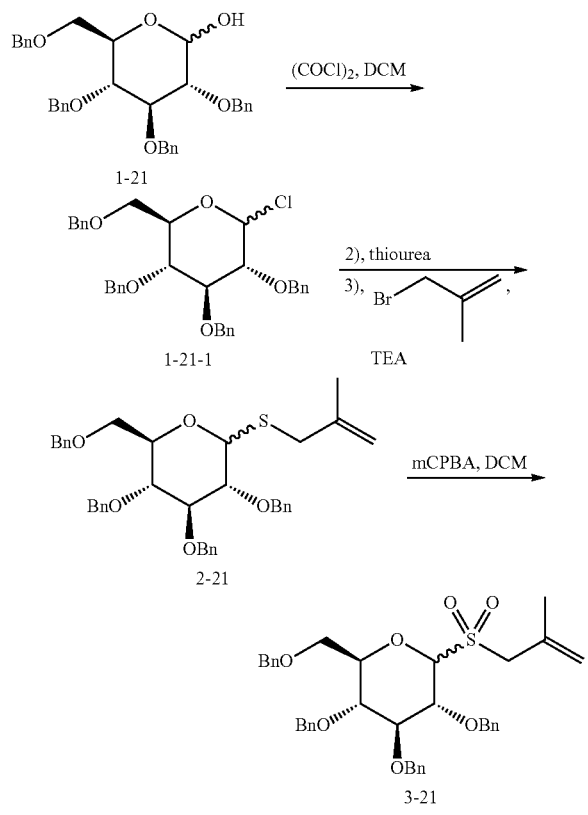

Detailed procedures were as follows:

(1) 2,3,4,6-Tetra-O-benzyl-D-glucopyranose (i.e. 1-21, 5.4 g, 10 mmol) was dissolved in 50 mL dichloromethane, and oxalyl chloride (1.7 mL, 20 mmol) was slowly drop added to the reaction solution at 0° C., then the reaction was warmed to room temperature and stirred for 18 h. Ice water was added to quench oxalyl chloride until no gas was released. The reaction solution was extracted with dichloromethane. The organic layers were combined, washed with saturated brine, dried over anhydrous sodium sulfate, and then filtered. The filtrate was rotatory evaporated, to obtain intermediate 1-21-1, that was directly used in the next step without purification.

(2) Intermediate 1-21-1 and thiourea (1.2 g, 15 mmol) were dissolved in acetonitrile (30 mL), and the reaction solution was refluxed for 2 h, cooled to room temperature, to which were then added triethylamine (15 mmol), 3-bromo-2-methylpropylene (15 mmol). After refluxing for 4 h, the reaction solution was cooled to room temperature. Acetonitrile was rotatory evaporated under reduced pressure, and to the residue were added dichloromethane and water. The resultant solution was extracted with dichloromethane, washed with saturated brine, dried over anhydrous sodium sulfate, and then filtered. The filtrate was concentrated, to obtain corresponding intermediate 2-21, that was directly used in the next step without purification.

(3) At 0° C., crude intermediate 2-21 obtained in the previous step was dissolved in dichloromethane (10 mL), to which was slowly added m-CPBA (2.5 equiv.), and the reaction was further stirred for 2 h. After intermediate 2-21 disappeared by TLC detection, the reaction solution was filtered, and the filtrate was successively washed with saturated NaHCO₃ aqueous solution and saturated brine. The organic phase was dried over anhydrous sodium sulfate and filtered. The filtrate was rotatory evaporated and purified by column chromatography, to obtain the product 3-21 (4.5 g, with a purity of >90% and a three-step total yield of 70%) (i.e. compound 3-21).

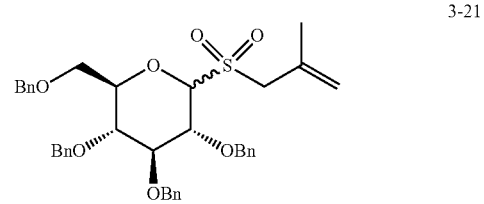 [SMILES: C=C(C)CS(=O)(=O)C1O[C@H](COCc2ccccc2)[C@@H](OCc2ccccc2)[C@H](OCc2ccccc2)[C@H]1OCc1ccccc1]

$^1$H NMR (CDCl₃, 400 MHz) δ: 7.44-7.22 (m, 18H), 7.16 (dd, J=6.1, 3.1 Hz, 2H), 5.21 (s, 0.32H), 5.16 (d, J=1.6 Hz, 1H), 5.09 (s, 0.68H), 5.04 (d, J=6.0 Hz, 0.69H), 4.99 (d, J=9.7 Hz, 0.33H), 4.94 (d, J=11.1 Hz, 0.34H), 4.90-4.66 (m, 4.6H), 4.58-4.38 (m, 4.0H), 4.15-4.06 (m, 1H), 4.04 (d, J=13.7 Hz, 0.34H), 3.94 (d, J=13.5 Hz, 0.69H), 3.80-3.74 (m, 0.35H), 3.74-3.50 (m, 4.6H), 1.96 (s, 1H), 1.94 (s, 2H).

Synthesis of Compounds 3-22-3-38

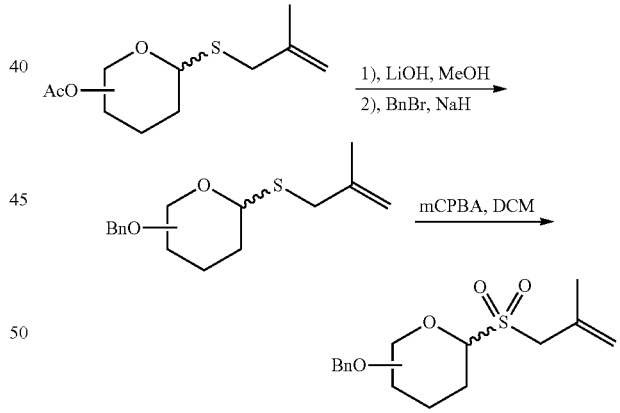

Detailed procedures were as follows:

a) At room temperature, the peracetyl-protected thioether substrates synthesized by above 1-4 routes were dissolved in 10 mL methanol, and then the reaction solution was cooled to 0° C., to which was slowly added the solid of lithium hydroxide (0.5 equiv.). After addition, the temperature was still kept at 0° C., and the mixture was allowed to react 1 h. After completion of the reaction, the reaction solution was rotatory evaporated, and the crude product was dissolved in DMF (10 mL). 60% NaH (—OH/1.5 equiv.) was slowly added in batches at 0° C., and the mixture was stirred for 30 min, to which was then added benzyl bromide (—OH/1.5 equiv.). The reaction was further stirred for 30 min, and then warmed to room temperature, followed by stirring for additional 12 h. After completion of the reaction, ice water was added, and the resultant solution was extracted with dichloromethane. The organic layers were combined, successively washed with water and saturated brine, dried with anhydrous sodium sulfate, filtered, concentrated, and purified by column chromatography, to obtain a perbenzyl-protected thioether intermediate.

b) At 0° C., the intermediate obtained in the previous step was dissolved in dichloromethane (10 mL), to which was slowly added m-CPBA (2.5 equiv.), and the reaction was further stirred for 2 h. After the starting material disappeared by TLC detection, the reaction solution was filtered, and the filtrate was successively washed with saturated NaHCO₃ aqueous solution and saturated brine. The organic phase was dried over anhydrous sodium sulfate and filtered. The filtrate was rotatory evaporated and purified by column chromatography, to obtain the products 3-22-3-38.

The characterization data were as follows.

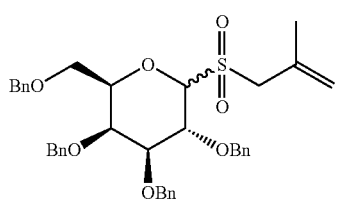
3-22

Purity >90%; ¹H NMR (400 MHz, chloroform-d) δ 7.42-7.20 (m, 20H), 5.14 (d, J=1.6 Hz, 2H), 4.96 (d, J=11.5 Hz, 2H), 4.82 (d, J=9.7 Hz, 1H), 4.74 (d, J=2.6 Hz, 2H), 4.61 (d, J=11.7 Hz, 1H), 4.48-4.38 (m, 4H), 3.97 (d, J=13.7 Hz, 1H), 3.88 (d, J=2.7 Hz, 1H), 3.68-3.56 (m, 4H), 3.49 (dd, J=7.9, 4.4 Hz, 1H), 1.95 (d, J=1.3 Hz, 3H).

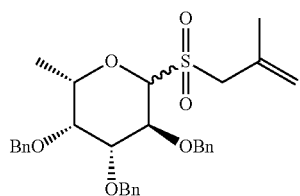
3-23

Purity >90%; ¹H NMR (400 MHz, chloroform-d) δ 7.43-7.24 (m, 15H), 5.17 (t, J=1.6 Hz, 1H), 5.08 (s, 1H), 5.01 (d, J=11.7 Hz, 1H), 4.97 (d, J=9.7 Hz, 1H), 4.83 (d, J=9.7 Hz, 1H), 4.78 (d, J=11.9 Hz, 1H), 4.74 (d, J=11.8 Hz, 1H), 4.70 (d, J=11.7 Hz, 1H), 4.49-4.38 (m, 2H), 3.96 (d, J=13.6 Hz, 1H), 3.69-3.51 (m, 4H), 1.96 (d, J=1.1 Hz, 3H), 1.24 (d, J=6.4 Hz, 3H).

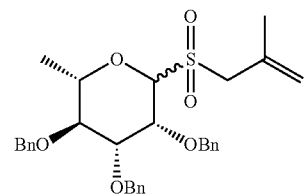
3-24

Purity >90%; ¹H NMR (400 MHz, chloroform-d) δ 7.39-7.24 (m, 15H), 5.17 (t, J=1.6 Hz, 1H), 5.11 (s, 1H), 4.92 (d, J=2.4 Hz, 1H), 4.84 (d, J=11.2 Hz, 1H), 4.69 (d, J=11.9 Hz, 1H), 4.63 (dd, J=12.2, 6.0 Hz, 3H), 4.56 (d, J=11.1 Hz, 1H), 4.44 (t, J=2.9 Hz, 1H), 4.35-4.26 (m, 1H), 4.08 (dd, J=8.4, 3.4 Hz, 1H), 3.90 (d, J=13.8 Hz, 1H), 3.60 (t, J=8.8 Hz, 1H), 3.54 (d, J=13.8 Hz, 1H), 1.92 (s, 3H), 1.31 (d, J=6.2 Hz, 3H).

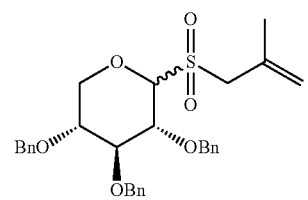
3-25

7.40-7.24 (m, 15H), 5.20 (t, J=1.6 Hz, 1H), 5.08 (s, 1H), 4.94-4.90 (m, 1H), 4.90-4.84 (m, 2H), 4.78 (d, J=9.8 Hz, 1H), 4.69 (d, J=11.7 Hz, 1H), 4.59 (d, J=11.6 Hz, 1H), 4.46 (d, J=9.2 Hz, 1H), 4.11 (dd, J=11.4, 5.0 Hz, 1H), 4.05 (t, J=8.8 Hz, 1H), 3.89 (d, J=13.6 Hz, 1H), 3.76-3.64 (m, 2H), 3.61 (d, J=13.5 Hz, 1H), 3.30 (dd, J=11.5, 9.1 Hz, 1H), 1.95 (s, 3H).

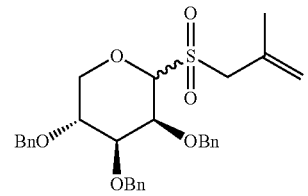
3-26

Purity >90%; ¹H NMR (400 MHz, chloroform-d) δ 7.39-7.19 (m, 15H), 5.17 (t, J=1.7 Hz, 1H), 5.09 (s, 1H), 4.85 (d, J=6.8 Hz, 1H), 4.67 (dd, J=11.7, 3.5 Hz, 2H), 4.58 (dd, J=11.7, 5.8 Hz, 2H), 4.50 (d, J=3.1 Hz, 2H), 4.35 (dd, J=6.8, 3.0 Hz, 1H), 4.02 (dd, J=11.9, 4.3 Hz, 1H), 3.93-3.83 (m, 3H), 3.67-3.63 (m, 1H), 3.61 (d, J=13.7 Hz, 1H), 1.94 (s, 3H).

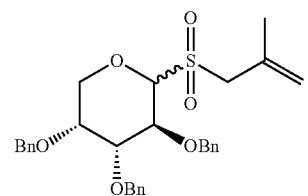
3-27

Purity >90%; ¹H NMR (400 MHz, chloroform-d) δ 7.42-7.26 (m, 15H), 5.18 (q, J=1.6 Hz, 1H), 5.08 (s, 1H), 4.90 (d, J=10.0 Hz, 1H), 4.85 (d, J=10.0 Hz, 1H), 4.75 (d, J=12.5 Hz, 1H), 4.71-4.59 (m, 3H), 4.51-4.38 (m, 2H), 4.23 (dd, J=12.4, 3.0 Hz, 1H), 3.91 (d, J=13.6 Hz, 1H), 3.76 (td, J=3.0, 1.4 Hz, 1H), 3.71-3.61 (m, 2H), 3.38 (dd, J=12.5, 1.5 Hz, 1H), 1.96 (s, 3H).

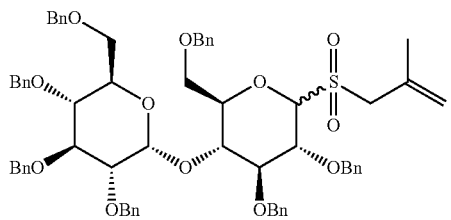

3-29

Purity >90%; ¹H NMR (400 MHz, chloroform-d) δ 7.34-7.12 (m, 35H), 5.51 (d, J=3.7 Hz, 1H), 5.17 (s, 2H), 4.95-4.72 (m, 6H), 4.64-4.34 (m, 9H), 4.16 (t, J=8.8 Hz, 1H), 4.09-3.97 (m, 2H), 3.87 (t, J=9.4 Hz, 2H), 3.80-3.68 (m, 3H), 3.68-3.52 (m, 4H), 3.48 (dt, J=10.5, 3.1 Hz, 2H), 1.96 (s, 3H).

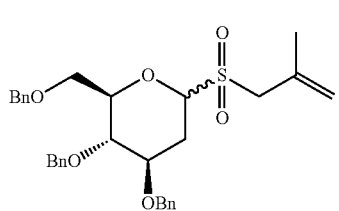

3-28

Purity >90%; ¹H NMR (400 MHz, chloroform-d) δ 7.37-7.22 (m, 15H), 5.18 (ddt, J=7.4, 5.7, 2.9 Hz, 1H), 4.90 (t, J=10.1 Hz, 1H), 4.81-4.37 (m, 7H), 4.26-4.11 (m, 1H), 3.99 (dd, J=26.0, 13.7 Hz, 1H), 3.78-3.53 (m, 4H), 3.53-3.45 (m, 1H), 1.94 (s, 3H).

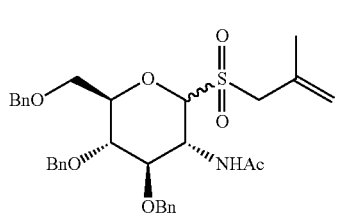

3-30

Purity >90%; ¹H NMR (400 MHz, chloroform-d) δ 7.37-7.26 (m, 13H), 7.19 (dd, J=7.3, 2.3 Hz, 2H), 5.77 (d, J=7.0 Hz, 1H), 5.22-5.10 (m, 1H), 4.85 (d, J=11.5 Hz, 1H), 4.81 (d, J=11.0 Hz, 1H), 4.68 (d, J=11.5 Hz, 1H), 4.57 (d, J=10.8 Hz, 1H), 4.55-4.46 (m, 3H), 3.97 (d, J=13.6 Hz, 1H), 3.79-3.43 (m, 7H), 1.92 (s, 3H), 1.85 (s, 3H).

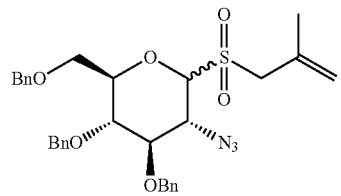

3-31

Purity >90%; ¹H NMR (400 MHz, chloroform-d) δ 7.44-7.26 (m, 13H), 7.16 (dd, J=7.3, 2.3 Hz, 2H), 5.26-5.20 (m, 1H), 5.17 (s, 1H), 4.91 (d, J=1.8 Hz, 1H), 4.81 (d, J=11.1 Hz, 1H), 4.75 (s, 2H), 4.58 (d, J=12.1 Hz, 1H), 4.51-4.45 (m, 3H), 4.42 (ddd, J=9.8, 5.1, 2.3 Hz, 1H), 4.34 (dd, J=8.7, 3.9 Hz, 1H), 3.97 (d, J=13.9 Hz, 1H), 3.85 (t, J=9.2 Hz, 1H), 3.69-3.54 (m, 3H), 1.94 (s, 3H).

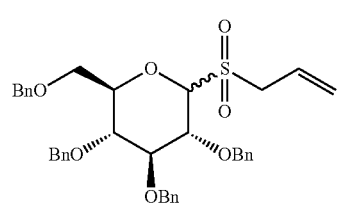

3-32

Purity >90%; ¹H NMR (400 MHz, chloroform-d) δ 7.42-7.24 (m, 48H), 7.16 (dd, J=7.0, 2.5 Hz, 6H), 5.98-5.80 (m, 3H), 5.51-5.33 (m, 6H), 5.00 (d, J=6.3 Hz, 2H), 4.96 (d, J=6.5 Hz, 1H), 4.92 (d, J=7.9 Hz, 1H), 4.87 (d, J=4.2 Hz, 2H), 4.83 (d, J=9.0 Hz, 2H), 4.78 (d, J=8.3 Hz, 3H), 4.76-4.73 (m, 2H), 4.70 (d, J=11.5 Hz, 2H), 4.55 (d, J=11.6 Hz, 3H), 4.51 (d, J=11.8 Hz, 3H), 4.48 (d, J=9.1 Hz, 2H), 4.46-4.43 (m, 2H), 4.43-4.36 (m, 3H), 4.13-4.05 (m, 3H), 3.98 (dt, J=13.9, 8.8 Hz, 3H), 3.77 (t, J=8.5 Hz, 1H), 3.74-3.48 (m, 12H).

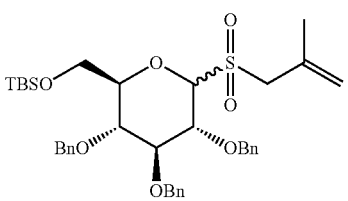

3-33

Purity >90%; ¹H NMR (400 MHz, chloroform-d) δ 7.33-7.19 (m, 15H), 5.17 (s, 1H), 5.14 (t, J=1.6 Hz, 1H), 4.94 (d, J=9.7 Hz, 1H), 4.89 (d, J=11.0 Hz, 1H), 4.82 (d, J=11.0 Hz, 1H), 4.78 (d, J=11.0 Hz, 1H), 4.71 (d, J=9.7 Hz, 1H), 4.59 (d, J=11.0 Hz, 1H), 4.45 (d, J=9.5 Hz, 1H), 4.07-3.95 (m, 2H), 3.83-3.66 (m, 3H), 3.58-3.47 (m, 2H), 3.34 (ddd, J=9.7, 5.1, 1.8 Hz, 1H), 1.93 (d, J=1.2 Hz, 3H), 0.84 (s, 9H), 0.02 (s, 3H), 0.00 (s, 3H).

3-34

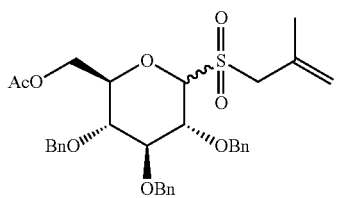

Purity >90%; ¹H NMR (400 MHz, chloroform-d) δ 7.32-7.28 (m, 13H), 7.17 (dt, J=7.2, 2.4 Hz, 2H), 5.00 (d, J=9.7 Hz, 1H), 4.97 (d, J=11.1 Hz, 1H), 4.89 (d, J=10.7 Hz, 1H), 4.85 (d, J=7.8 Hz, 1H), 4.84 (s, 1H), 4.74 (d, J=9.7 Hz, 1H), 4.59 (d, J=10.8 Hz, 1H), 4.48 (dd, J=12.1, 1.7 Hz, 1H), 4.03-3.97 (m, 1H), 3.79 (t, J=8.6 Hz, 1H), 3.70-3.63 (m, 2H), 3.60-3.51 (m, 4H), 2.04 (s, 3H), 1.98 (s, 3H).

3-35

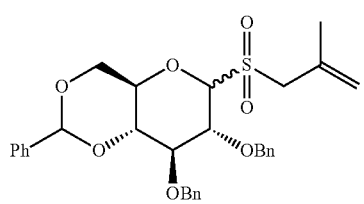

Purity >90%; ¹H NMR (400 MHz, chloroform-d) δ 7.58-7.27 (m, 15H), 5.59 (s, 1H), 5.22 (s, 1H), 5.07 (s, 1H), 5.02-4.75 (m, 4H), 4.58 (d, J=9.4 Hz, 1H), 4.37 (dd, J=10.5, 5.0 Hz, 1H), 4.16 (t, J=8.9 Hz, 1H), 3.96-3.81 (m, 3H), 3.77 (t, J=9.4 Hz, 1H), 3.66 (d, J=13.6 Hz, 1H), 3.52 (dt, J=9.8, 4.9 Hz, 1H), 1.97 (s, 3H).

3-36

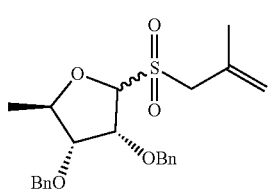

Purity >90%; ¹H NMR (400 MHz, chloroform-d) δ 7.47-7.41 (m, 2H), 7.39-7.27 (m, 8H), 5.14 (p, J=1.5 Hz, 1H), 4.99-4.90 (m, 2H), 4.84 (d, J=10.5 Hz, 1H), 4.77 (d, J=10.5 Hz, 1H), 4.64 (d, J=11.9 Hz, 1H), 4.53-4.44 (m, 2H), 4.38 (dq, J=9.0, 6.1 Hz, 1H), 3.89 (d, J=13.0 Hz, 1H), 3.71 (d, J=12.8 Hz, 1H), 3.52 (dd, J=8.9, 4.3 Hz, 1H), 1.89 (t, J=1.2 Hz, 3H), 1.32 (d, J=6.1 Hz, 3H).

3-37

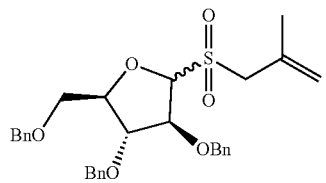

Purity >90%; ¹H NMR (400 MHz, chloroform-d) δ 7.41-7.17 (m, 15H), 5.23 (t, J=1.6 Hz, 1H), 5.18 (s, 1H), 4.96 (d, J=3.6 Hz, 1H), 4.74 (dd, J=4.8, 3.7 Hz, 1H), 4.70 (d, J=11.7 Hz, 1H), 4.59-4.43 (m, 6H), 4.22 (dd, J=8.5, 4.8 Hz, 1H), 3.96 (d, J=13.7 Hz, 1H), 3.75-3.62 (m, 2H), 3.56 (dd, J=11.5, 4.5 Hz, 1H), 1.99 (s, 3H).

3-38

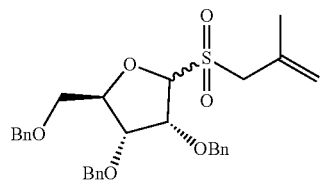

Purity >90%; ¹H NMR (400 MHz, chloroform-d) δ 7.39-7.24 (m, 15H), 5.20 (t, J=1.6 Hz, 1H), 5.15 (s, 1H), 5.02 (d, J=1.5 Hz, 1H), 4.68 (d, J=11.8 Hz, 1H), 4.61-4.42 (m, 6H), 4.39 (d, J=11.6 Hz, 1H), 4.02 (dd, J=8.2, 5.2 Hz, 1H), 3.87 (d, J=13.8 Hz, 1H), 3.69 (dd, J=11.0, 3.1 Hz, 1H), 3.61 (dd, J=11.0, 6.5 Hz, 1H), 3.52 (d, J=13.7 Hz, 1H), 1.94 (s, 3H).

The synthesis of compounds 3-39-3-40 was performed by the same route as that of compound 3-1 above, and their structures and characterization data were as follows:

3-39

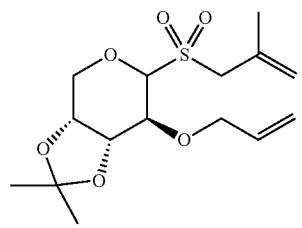

Purity >90%; ¹H NMR (400 MHz, chloroform-d) δ 5.96 (ddt, J=16.6, 10.0, 5.9 Hz, 1H), 5.32 (dd, J=17.2, 1.7 Hz, 1H), 5.24-5.18 (m, 2H), 5.13 (s, 1H), 4.44 (d, J=7.9 Hz, 1H), 4.37-4.22 (m, 4H), 4.17 (dd, J=12.6, 4.3 Hz, 1H), 4.11 (dd, J=8.0, 6.1 Hz, 1H), 3.95 (d, J=13.6 Hz, 1H), 3.89 (dd, J=12.5, 4.0 Hz, 1H), 3.67 (d, J=13.6 Hz, 1H), 1.98 (d, J=1.4 Hz, 3H), 1.54 (s, 3H), 1.37 (s, 3H).

3-40

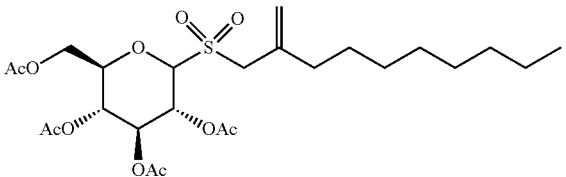

(2R,3R,4S,5R)-2-(acetoxymethyl)-6-((2-methylene-decyl)sulfonyl)tetrahydro-2H-pyran-3,4,5-triyl triacetate Purity >90%; ¹H NMR (400 MHz, chloroform-d) δ 5.53 (t, J=9.6 Hz, 1H), 5.31 (t, J=9.4 Hz, 1H), 5.28-5.19 (m, 2H), 5.10 (t, J=9.8 Hz, 1H), 4.57 (d, J=10.0 Hz, 1H), 4.25 (dd, J=5.4, 3.8 Hz, 2H), 3.95 (d, J=13.6 Hz, 1H), 3.80 (dq, J=7.4, 2.5 Hz, 1H), 3.68 (d, J=13.6 Hz, 1H), 2.26 (t, J=7.7 Hz, 2H), 2.19-1.95 (m, 12H), 1.46 (dt, J=14.7, 7.2 Hz, 2H), 1.38-1.15 (m, 10H), 0.88 (t, J=6.6 Hz, 3H). ¹³C NMR (101 MHz, chloroform-d) δ 170.37, 170.09, 169.20, 169.13, 136.99, 119.74, 85.59, 73.16, 67.54, 66.11, 61.64, 55.84, 35.73, 31.85, 29.41, 29.23, 29.09, 27.33, 22.65, 20.68, 20.60, 20.54, 20.52, 14.10.

Synthesis of S-Glycosyl Compound:

Then, the allylsulfone glycosyl donor prepared above was used as raw material to react with the glycosyl acceptor, to synthesize S-glycosyl compound of the present invention. For example, using the above compound 3-1 as a raw material, the synthetic route was as follows:

Route 1: Under nitrogen atmosphere, compound 3-1 (1.0 equiv), glycosyl acceptor a (1.2 equiv), and photosensitizer Ir[dF(CF$_3$)(ppy)$_2$](dtbbpy)PF$_6$ (0.01 equiv) were added to the flask for catalytic reaction, to which was added acetonitrile (making the concentration of compound 3-1 be 0.1 mol/L), and the reaction was stirred at room temperature for 4 h under the irradiation of Blue LED, to obtain the S-glycosyl compound S-a.

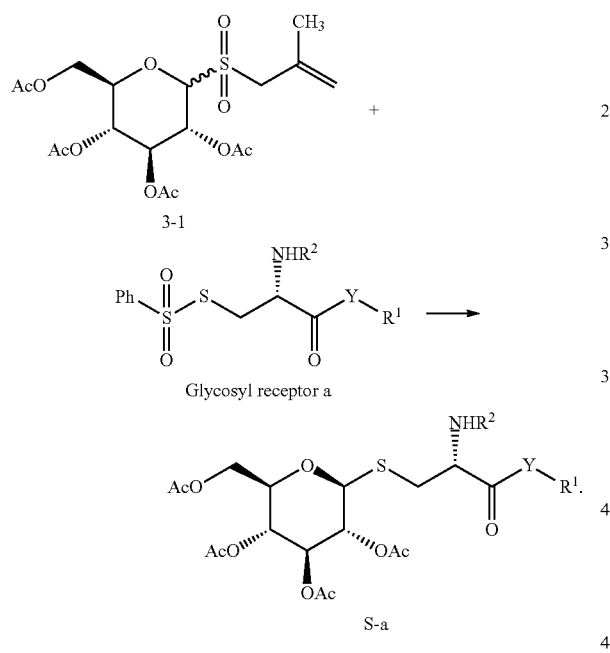

Wherein, Y is selected from NH or O; R$^1$ is selected from methyl,

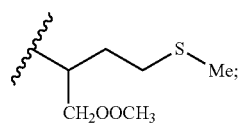

R$^2$ is selected from Bz, H,

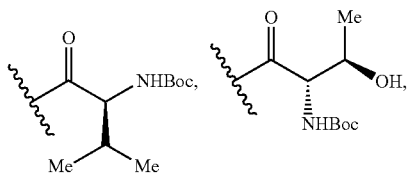

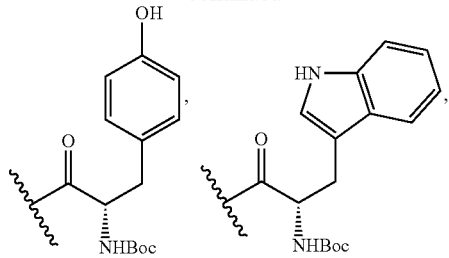

and Boc.

Route 2: Under nitrogen atmosphere, compound 3-1 (1.0 equiv), disulfide compound b (2.0 equiv), and photosensitizer Ir[dF(CF$_3$)(ppy)$_2$](dtbbpy)PF$_6$ (0.01 equiv) were added to the flask for catalytic reaction, to which was added acetonitrile (making the concentration of compound 3-1 be 0.1 mol/L), and the reaction was stirred at 45° C. for 2 h under the irradiation of Blue LED, to obtain the S-glycosyl compound S-b.

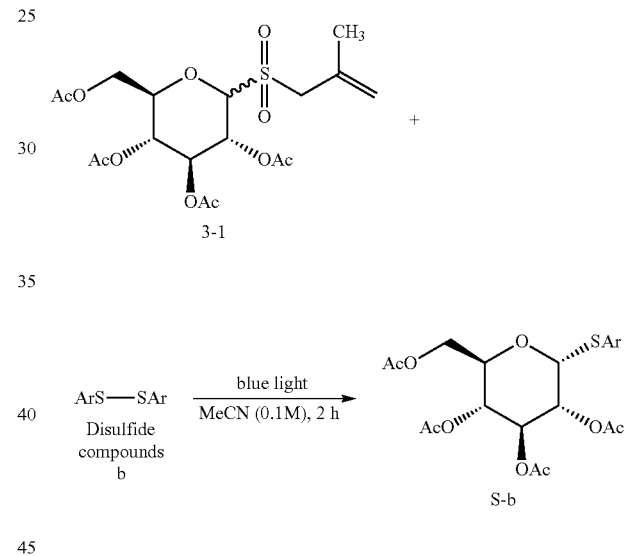

Wherein, Ar represents aryl.

Route 3: Under nitrogen atmosphere, compound 3-1 (1.0 equiv.), disulfide compound c (2.0 equiv.), and photosensitizer Ir[dF(CF$_3$)(ppy)$_2$](dtbbpy)PF$_6$ (0.01 equiv.) were added to the flask for catalytic reaction, to which was added acetonitrile (0.1 mol/L), and the reaction was stirred at room temperature for 2 h under the irradiation of Blue LED, to obtain the S-glycosyl compound S-c.

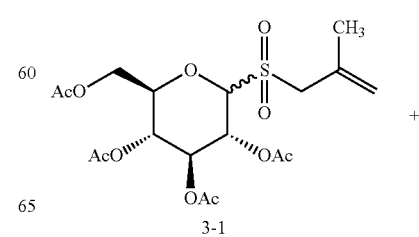

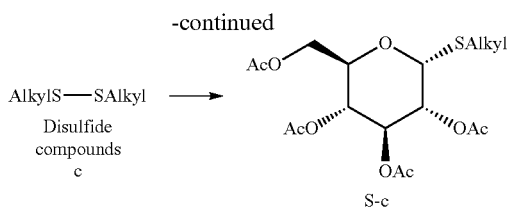

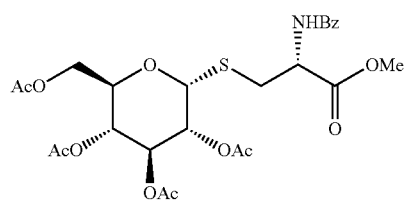

Wherein, Alkyl represents alkyl.

Route 4: Under nitrogen atmosphere, compound 3-x (1.0 equiv), glycosyl disulfide receptor d (1.2 equiv), and photosensitizer Ir[dF(CF$_3$)(ppy)$_2$](dtbbpy)PF$_6$ (0.01 equiv) were added to the flask for catalytic reaction, to which was added acetonitrile (making the concentration of compound 3-1 to be 0.1 mol/L), and the reaction was stirred at room temperature for 4 h under the irradiation of Blue LED, to obtain the S-glycosyl compound S-d.

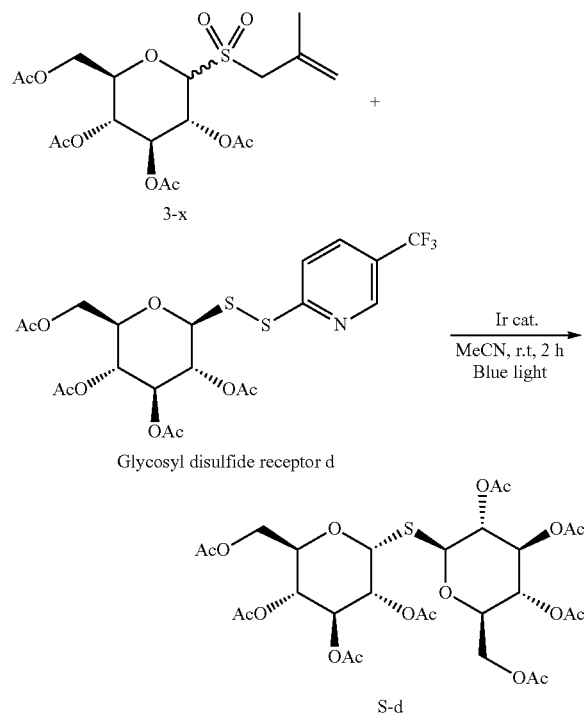

The above synthetic route of the present invention was not limited to using compound 3-1 as a raw material. Using the same method, replacing the raw material compound 3-1 with any allylsulfone glycosyl donor prepared above in the present invention could obtain the corresponding S-glycosyl compounds.

The following are synthetic examples of specific S-glycosyl compounds according to the present invention.

Example 17 Synthesis of S-Glycoside Compound S-1-S-17 and S-22 According to the Present Invention Using the same method as that of route 1 above, S-glycosyl compounds S-1-S-17 and S-22 according to the present invention were prepared. The structure and characterization are as follows:

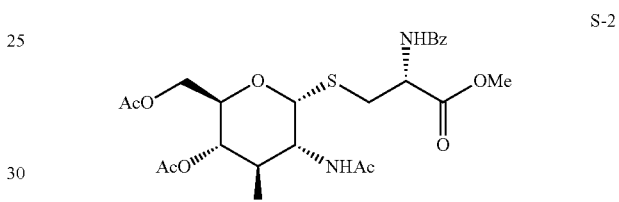

Methyl N-benzoyl-S-(2,3,4,6-tetraacetoxy-1-α-D-glucosyl)-L-cysteine (with a purity of >90%, yield=92%)

$^1$H NMR (400 MHz, chloroform-d) δ 7.83 (m, 2H), 7.58-7.49 (m, 1H), 7.43 (m, 3H), 5.64 (d, J=5.8 Hz, 1H), 5.32-5.20 (m, 2H), 5.07-4.94 (m, 2H), 4.37 (ddd, J=10.3, 5.0, 2.2 Hz, 1H), 4.25 (dd, J=12.6, 5.0 Hz, 1H), 4.16 (dd, J=10.6, 2.2 Hz, 1H), 3.80 (s, 2H), 3.35 (dd, J=14.6 Hz, J=3.5 Hz, 1H), 3.13 (dd, J=14.6, 3.5 Hz, 1H), 2.07 (s, 3H), 2.02 (s, 3H), 2.02 (s, 3H), 1.99 (s, 3H).

Methyl N-benzoyl-S-(2,3,4,6-tetraacetoxy-2-deoxyamino-α-D-glucosyl)-L-cysteine (with a purity of >90%, Yield=70%)

$^1$H NMR (400 MHz, chloroform-d) δ 7.89-7.84 (m, 2H), 7.57-7.50 (m, 2H), 7.43 (m, 2H), 5.80 (d, J=8.8 Hz, 1H), 5.41 (d, J=5.3 Hz, 1H), 5.35-5.29 (m, 1H), 5.14-5.07 (t, J=9.6 Hz, 1H), 4.98 (dd, J=11.3, 9.3 Hz, 1H), 4.54 (ddd, J=11.3, 8.8, 5.3 Hz, 1H), 4.32 (dt, J=10.1, 3.6 Hz, 1H), 4.20 (d, J=3.7 Hz, 2H), 3.80 (s, 3H), 3.41 (dd, J=14.7, 4.7 Hz, 1H), 3.17 (dd, J=14.6, 3.3 Hz, 1H), 2.04 (s, 3H), 2.03 (s, 3H), 1.97 (s, 3H), 1.96 (s, 3H).

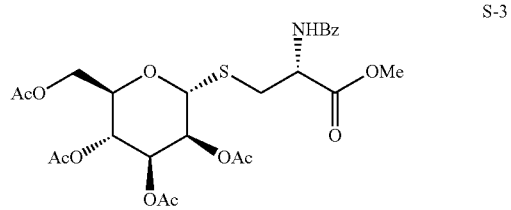

Methyl N-benzoyl-S-(2,3,4,6-tetraacetoxy-1-α-D-mannosyl)-L-cysteine (with a purity of >90%, Yield=88%)

$^1$H NMR (400 MHz, chloroform-d) δ 7.90-7.85 (m, 2H), 7.57-7.50 (m, 1H), 7.43 (m, 2H), 5.38 (dd, J=3.3, 1.7 Hz, 1H), 5.32-5.24 (m, 3H), 5.18 (dd, J=10.0, 3.3 Hz, 1H), 4.33 (d, J=4.4 Hz, 1H), 4.26-4.15 (m, 2H), 3.80 (s, 3H), 3.38 (dd, J=14.5, 4.9 Hz, 1H), 3.22 (dd, J=14.5, 3.6 Hz, 1H), 2.14 (s, 3H), 2.05 (s, 3H), 1.99 (s, 3H), 1.95 (s, 3H).

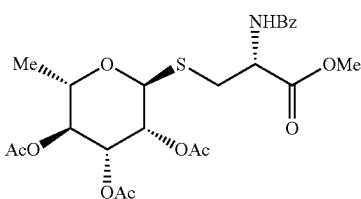

S-4

Methyl N-benzoyl-S-(2,3,4-triacetoxy-1-α-D-rhamnosyl)-L-cysteine (with a purity of >90%, Yield=87%)

$^1$H NMR (400 MHz, chloroform-d) δ 7.90-7.86 (m, 2H), 7.57-7.50 (m, 1H), 7.43 (m, 2H), 5.34 (dd, J=3.4, 1.6 Hz, 1H), 5.22 (d, J=1.6 Hz, 1H), 5.18 (dd, J=10.0, 3.4 Hz, 1H), 5.11-5.04 (m, 2H), 4.21-4.07 (m, 1H), 3.35 (dd, J=13.9, 5.0 Hz, 1H), 3.16 (dd, J=13.9, 4.9 Hz, 1H), 2.09 (s, 3H), 2.05 (s, 3H), 1.97 (s, 3H), 1.23 (d, J=6.2 Hz, 3H).

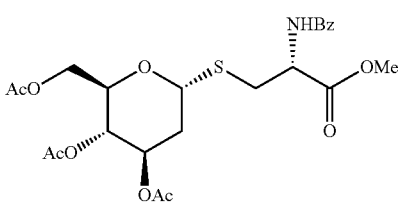

S-5

Methyl N-benzoyl-S-(3,4,6-triacetoxy-2-deoxy-α-D-glucosyl)-L-cysteine (with a purity of >90%, Yield=72%)

$^1$H NMR (400 MHz, chloroform-d) δ 7.90-7.86 (m, 2H), 7.57-7.50 (m, 1H), 7.43 (m, 2H), 5.43-5.39 (m, d, J=5.1 Hz, 1H), 5.29-5.23 (m, 1H), 5.21-5.13 (m, 1H), 4.96 (t, J=9.6 Hz, 1H), 4.33 (ddd, J=9.8, 5.3, 2.0 Hz, 1H), 4.27 (dd, J=12.3, 5.3 Hz, 1H), 4.13 (dd, J=12.3, 2.0 Hz, 1H), 3.79 (s, 3H), 3.35 (dd, J=14.6, 5.0 Hz, 1H), 3.16 (dd, J=14.6, 3.6 Hz, 1H), 2.35 (ddd, J=13.4, 5.2, 1.4 Hz, 1H), 2.25-2.14 (m, 1H), 2.04 (s, 3H), 2.00 (s, 3H), 1.97 (s, 3H).

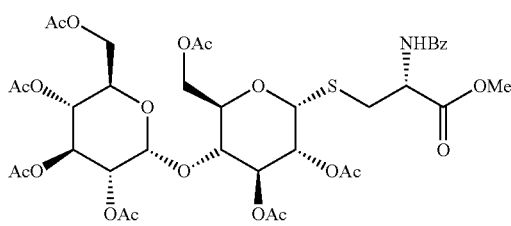

S-6

Methyl N-benzoyl-S-(2',3',6',2,3,4,6-heptaacetoxy-α-D-maltosyl)-L-cysteine (with a purity of >90%, Yield=75%)

$^1$H NMR (400 MHz, chloroform-d) δ 7.90-7.86 (m, 2H), 7.57-7.50 (m, 1H), 7.43 (m, 2H), 5.50 (d, J 5.7 Hz, JH), 5.42-5.32 (m, 2H), 5.30-5.21 (m, 2H), 5.12-5.04 (t, J=9.8 Hz, 1H), 4.91 (m, 2H), 4.51 (d, J=2.3 Hz, 1H), 4.31 (ddd, J=9.8, 5.2, 2.2 Hz, 1H), 4.24 (dd, J=12.4, 3.8 Hz, 1H), 4.15 (dd, J=12.3, 5.3 Hz, 1H), 4.07 (dd, J=12.5, 2.4 Hz, 1H), 4.03-3.97 (m, 1H), 3.87 (dd, J=9.8, 7.9 Hz, 1H), 3.83 (s, 3H), 3.34 (dd, J=14.6, 4.7 Hz, 1H), 3.16 (dd, J=14.6, 3.6 Hz, 1H), 2.10 (s, 3H), 2.06 (s, 3H), 2.05 (s, 2H), 2.04 (s, 3H), 2.03 (s, 3H), 2.01 (s, 2H), 2.00 (s, 3H).

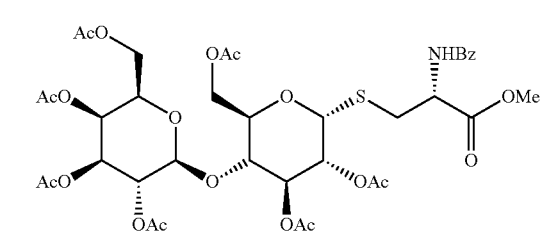

S-7

Methyl N-benzoyl-S-(2',3',6',2,3,4,6-heptaacetoxy-α-D Lactosyl)-L-cysteine (with a purity of >90%, Yield=80%)

$^1$H NMR (400 MHz, chloroform-d) δ 7.90-7.86 (m, 2H), 7.57-7.51 (m, 1H), 7.42 (m, 2H), 5.56 (d, J=5.7 Hz, 1H), 5.35 (d, J=3.4 Hz, 1H), 5.27 (t, J=9.5 Hz, 1H), 5.22 (m, 1H), 5.10 (dd, J=10.4, 7.9 Hz, 1H), 4.99-4.93 (m, 2H), 4.54-4.47 (m, 2H), 4.27 (ddd, J=10.1, 5.4, 1.9 Hz, 1H), 4.18-4.05 (m, 3H), 3.89 (t, J=6.9 Hz, 1H), 3.78 (s, 3H), 3.75-3.70 (t, J=9.4 Hz, 1H), 3.30 (dd, J=14.5, 5.0 Hz, 1H), 3.11 (dd, J=14.5, 3.6 Hz, 1H), 2.14 (s, 3H), 2.06 (s, 3H), 2.05 (s, 6H), 2.04 (s, 3H), 2.01 (s, 3H), 1.96 (s, 3H).

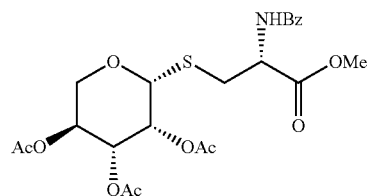

S-8

Methyl N-benzoyl-S-(2,3,4-triacetoxy-α-L-lyxosyl)-L-cysteine (with a purity of >90%, Yield=63%)

$^1$H NMR (400 MHz, Chloroform-d) δ 7.90-7.86 (m, 2H), 7.57-7.51 (m, 1H), 7.42 (m, 2H), 5.29 (dd, J=4.5, 3.3 Hz, 1H), 5.22 (dd, J=8.1, 3.3 Hz, 1H), 5.15 (dt, J=8.3, 4.3 Hz, 1H), 5.13-5.06 (m, 1H), 5.05-5.02 (m, 1H), 3.86 (d, J=2.3 Hz, 1H), 3.80 (s, 3H), 3.79 (d, J=2.8 Hz, 1H), 3.41 (dd, J=14.5, 4.7 Hz, 1H), 3.15 (dd, J=14.5, 3.9 Hz, 1H), 2.09 (s, 3H), 2.07 (s, 3H), 2.04 (s, 3H).

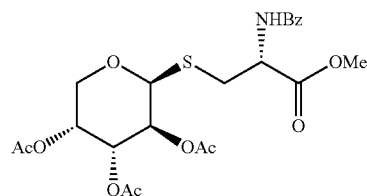

S-9

Methyl N-benzoyl-S-(2,3,4-triacetoxy-α-D-arabinosyl)-L-cysteine (with a purity of >90%, Yield=76%)

$^1$H NMR (400 MHz, chloroform-d) δ 7.90-7.86 (m, 2H), 7.57-7.51 (m, 1H), 7.42 (m, 2H), 5.72 (d, J=5.3 Hz, 1H), 5.30-5.27 (m, 1H), 5.23 (dd, J=10.1, 5.1 Hz, 1H), 5.17-5.13 (m, 1H), 5.08-5.03 (m, 1H), 4.21-4.15 (dd, J=13.2, 1.5 Hz, 1H), 3.80 (s, 3H), 3.35 (dd, J=14.1, 4.6 Hz, 1H), 3.05 (dd, J=14.1, 5.3 Hz, 1H), 2.11 (s, 3H), 2.05 (s, 2H), 2.00 (s, 3H).

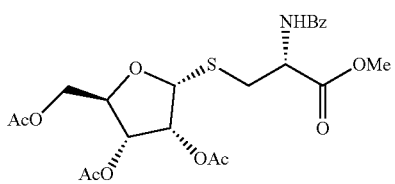

S-10

Methyl N-benzoyl-S-(2,3,5-triacetoxy-α-D-ribosyl)-L-cysteine (with a purity of >90%, Yield=78%)

¹H NMR (400 MHz, chloroform-d) δ 7.90-7.86 (m, 2H), 7.57-7.51 (m, 1H), 7.42 (m, 2H), 5.48 (t, J=3.2 Hz, 1H), 4.92 (d, J=7.7 Hz, 1H), 5.02 (m, 3H), 3.97 (dd, J=11.6, 4.4 Hz, 1H), 3.80 (s, 3H), 3.71 (dd, J=11.6, 8.3 Hz, 1H), 3.34 (dd, J=14.3, 4.7 Hz, 1H), 3.20 (dd, J=14.3, 5.3 Hz, 1H), 2.05 (s, 3H), 2.04 (s, 3H), 2.03 (s, 3H).

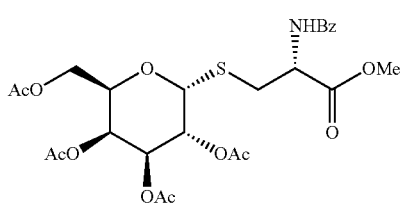

S-11

Methyl N-benzoyl-S-(2,3,4,6-tetraacetoxy-α-D-galactosyl)-L-cysteine (with a purity of >90%, Yield=63%)

¹H NMR (400 MHz, chloroform-d) δ 7.90-7.86 (m, 2H), 7.57-7.51 (m, 1H), 7.42 (m, 2H), 5.72 (d, J=5.6 Hz, 1H), 5.44 (d, J=3.3 Hz, 1H), 5.27 (dd, J=11.1, 5.6 Hz, 1H), 5.20 (m, 1H), 5.14 (dd, J=11.0, 3.3 Hz, 1H), 4.56 (t, J=6.4 Hz, 1H), 4.17 (dd, J=11.4, 5.2 Hz, 1H), 4.03 (dd, J=11.4, 7.4 Hz, 1H), 3.80 (s, 3H), 3.34 (dd, J=14.5, 4.9 Hz, 1H), 3.13 (dd, J=14.4, 3.8 Hz, 1H), 2.15 (s, 3H), 2.07 (s, 3H), 1.99 (s, 3H), 1.91 (s, 3H).

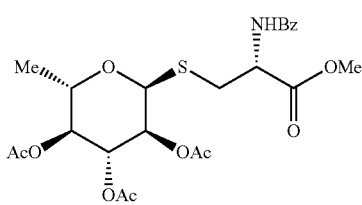

S-12

Methyl N-benzoyl-S-(2,3,4-triacetoxy-α-L-fucosyl)-L-cysteine (with a purity of >90%, Yield=71%)

¹H NMR (400 MHz, chloroform-d) δ 7.90-7.86 (m, 2H), 7.57-7.51 (m, 1H), 7.42 (m, 2H), 5.82 (d, J=5.1 Hz, 1H), 5.26 (m, 1H), 5.22-5.16 (m, 2H), 5.08 (m, 1H), 4.40 (q, J=6.5 Hz, 1H), 3.81 (s, 3H), 3.28 (dd, J=14.0, 4.6 Hz, 1H), 3.05 (dd, J=14.0, 5.2 Hz, 1H), 2.15 (s, 3H), 2.04 (s, 3H), 1.98 (s, 3H), 1.15 (d, J=6.5 Hz, 3H).

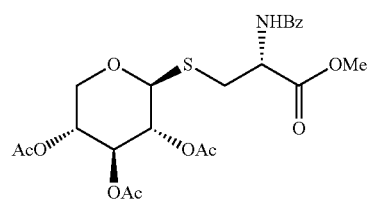

S-13

Methyl N-benzoyl-S-(2,3,4-triacetoxy-α-L-xylosyl)-L-cysteine (with a purity of >90%, Yield=73%)

¹H NMR (400 MHz, chloroform-d) δ 5.50 (d, J=5.3 Hz, 1H), 5.23 (t, J=9.2 Hz, 1H), 5.17 (m, 1H), 5.05 (m, 1H), 4.99-4.87 (m, 4H), 4.54 (d, J=9.2 Hz, 1H), 4.10 (dd, J=11.6, 5.3 Hz, 1H), 3.98-3.89 (m, 1H), 3.80 (s, 3H), 3.38 (s, 3H), 3.38-3.30 (m, 2H), 3.20 (dd, J=14.4, 5.3 Hz, 1H), 3.11 (dd, J=14.5, 3.8 Hz, 1H), 2.07 (s, 3H), 2.04 (s, 3H), 2.03 (s, 6H), 1.99 (s, 6H).

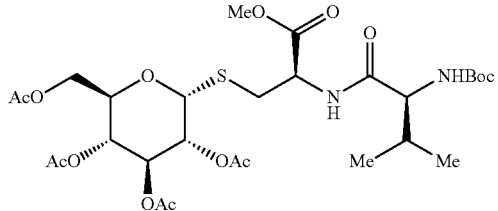

S-14

Methyl N—(N-t-butoxy-L-valinyl)-S-(2,3,4,6-tetraacetoxy-D-glucosyl)-L-cysteine (with a purity of >90%, Yield=70%)

¹H NMR (400 MHz, chloroform-d) δ 5.60 (d, J=5.8 Hz, 1H), 5.25 (d, J=9.8 Hz, 1H), 5.17-5.07 (m, 1H), 5.02-4.96 (m, 1H), 4.91 (m, 1H), 4.35-4.28 (m, 2H), 4.26-4.20 (m, 1H), 4.01 (m, 1H), 3.78 (s, 3H), 3.16-3.03 (m, 2H), 2.22-2.15 (m, 1H), 2.11 (s, 3H), 2.06 (s, 2H), 2.04 (s, 3H), 2.01 (s, 3H), 1.46 (s, 9H), 1.00-0.97 (d, J=6.9 Hz, 3H), 0.93 (d, J=6.9 Hz, 3H).

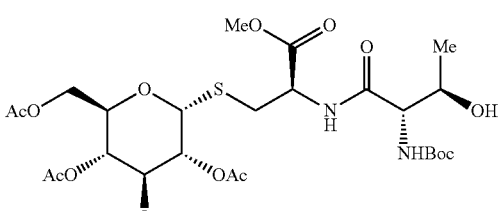

S-15

Methyl N—(N-t-butoxy-L-threoninyl)-S-(2,3,4,6-tetraacetoxy-D-glucosyl)-L-cysteine (with a purity of >90%, Yield=90%)

¹H NMR (400 MHz, chloroform-d) δ 7.90-7.86 (m, 2H), 7.65 (t, J=7.4 Hz, 1H), 7.59-7.52 (m, 2H), 7.48 (d, J=7.9 Hz, 1H), 5.67 (d, J=5.7 Hz, 1H), 5.54 (d, J=7.7 Hz, 1H), 5.27 (t, J=9.8 Hz, 1H), 5.08-5.01 (m, 1H), 4.96 (dd, J=10.4, 5.8 Hz, 1H), 4.94-4.88 (m, 1H), 4.40 (dd, J=6.6, 2.4 Hz, 1H), 4.33 (dt, J=10.1, 3.6 Hz, 1H), 4.25 (d, J=2.6 Hz, 2H), 4.19-4.14 (m, 1H), 3.76 (s, 3H), 3.08 (d, J=4.8 Hz, 2H), 2.12 (s, 3H), 2.06 (s, 3H), 2.04 (s, 3H), 2.01 (s, 3H), 1.48 (s, 9H), 1.21 (d, J=6.3 Hz, 3H).

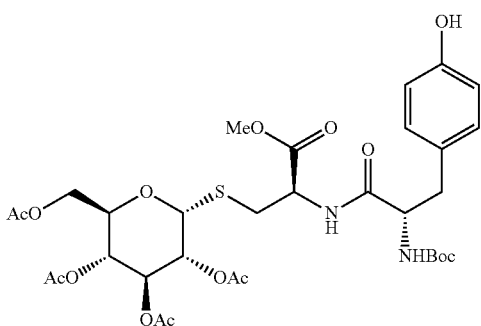

Methyl N—(N-t-butoxy-L-tyrosinyl)-S-(2,3,4,6-tetraacetoxy-D-glucosyl)-L-cysteine (with a purity of >90%, Yield=70%)

$^1$H NMR (400 MHz, chloroform-d) δ 7.90-7.86 (m, 2H), 7.65 (t, J=7.4 Hz, 1H), 7.59-7.52 (m, 2H), 5.42 (d, J=5.7 Hz, 1H), 5.27 (d, J=10.0 Hz, 1H), 5.14-5.03 (m, 1H), 4.96 (dd, J=10.4, 5.7 Hz, 1H), 4.87-4.72 (m, 2H), 4.38 (m, 1H), 4.34-4.25 (m, 2H), 4.19 (d, J=10.5 Hz, 1H), 3.77 (s, 3H), 3.11 (dd, J=14.0, 6.0 Hz, 1H), 3.04 m, 2H), 2.94 (dd, J=14.0, 6.4 Hz, 1H), 2.10 (s, 3H), 2.05 (s, 3H), 2.05 (s, 3H), 2.03 (s, 3H), 1.44 (s, 9H).

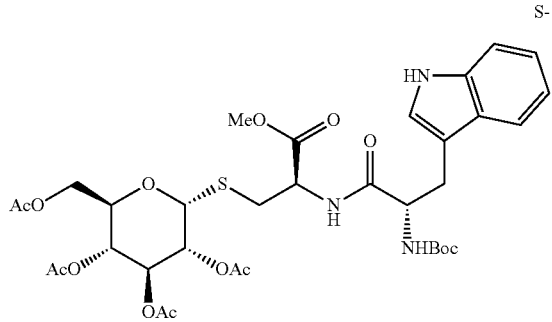

Methyl N—(N-t-butoxy-L-tryptophanyl)-S-(2,3,4,6-tetraacetoxy-D-glucosyl)-L-cysteine (with a purity of >90%, Yield=81%)

$^1$H NMR (400 MHz, chloroform-d) δ 8.81 (s, 1H), 7.63 (d, J=7.9 Hz, 1H), 7.38 (d, J=8.0 Hz, 1H), 7.22-7.15 (m, 1H), 7.15-7.08 (m, 2H), 6.93 (d, J=7.9 Hz, 1H), 5.23-5.14 (t, J=9.8 Hz, 1H), 5.09 (m, 2H), 4.89 (dd, J=10.3, 5.8 Hz, 2H), 4.85-4.79 (m, 1H), 4.58 (s, 1H), 4.24 (dt, J=10.2, 3.7 Hz, 1H), 4.17 (s, 1H), 3.68 (s, 3H), 3.47 (dd, J=14.6, 4.7 Hz, 1H), 3.15 (dd, J=14.6, 6.1 Hz, 1H), 2.95 (dd, J=14.3, 5.6 Hz, 2H), 2.78 (m, 1H), 2.07 (s, 3H), 2.04 (s, 3H), 2.04 (s, 3H), 2.02 (s, 3H), 1.46 (s, 9H).

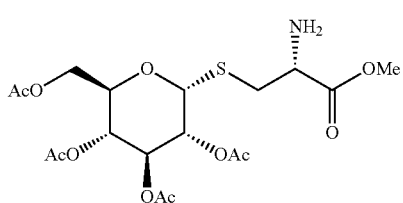

(2,3,4,6-Tetraacetyl-1-α-D-glucopyranosyl)-L-cysteine methyl ester (with a purity of >90%, Yield=28%).

$^1$H NMR (400 MHz, chloroform-d) δ 5.71 (d, J=5.8 Hz, 1H), 5.34 (t, J=9.8 Hz, 1H), 5.07-4.98 (m, 2H), 4.41 (ddd, 1=10.1, 4.8, 2.2 Hz, 1H), 4.29 (dd, J=12.4, 5.1 Hz, 1H), 4.14-4.10 (m, 1H), 3.74 (s, 3H), 3.71 (m, 1H), 2.92 (d, J=5.9 Hz, 2H), 2.10 (s, 3H), 2.07 (s, 3H), 2.04 (s, 3H), 2.01 (s, 3H).

Example 18 Synthesis of S-Glycoside Compound S-18 According to the Present Invention S-glycosyl compound S18 of the present invention was prepared by the same method as the above route 1, and the route was as follows:

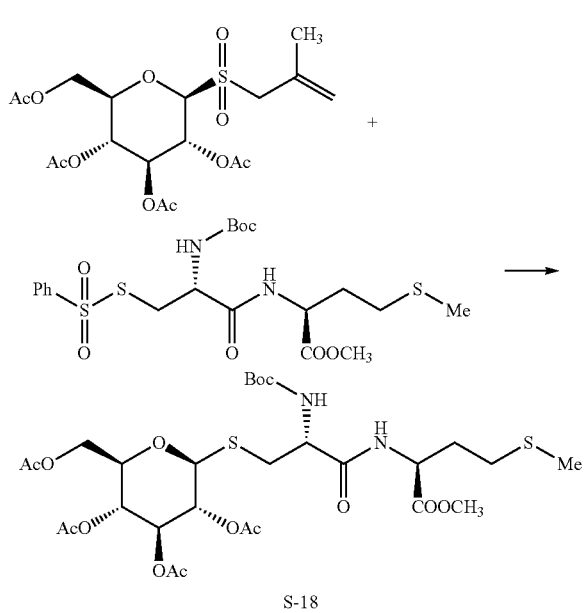

Methyl N—(N-t-butoxy-L-methioninyl)-S-(2,3,4,6-tetraacetoxy-D-glucosyl)-L-cysteine (with a purity of >90%, Yield=80%)

$^1$H NMR (400 MHz, chloroform-d) δ 7.90-7.87 (m, 2H), 7.67-7.62 (m, 1H), 7.55 (m, 2H), 5.68 (d, J=5.8 Hz, 1H), 5.48 (d, J=8.2 Hz, 1H), 5.34-5.28 (m, 1H), 5.08-5.00 (m, 2H), 4.68 (m, 1H), 4.39 (ddd, J=10.0, 4.5, 2.5 Hz, 1H), 4.33 (dd, J=12.3, 4.5 Hz, 1H), 4.16 (dd, J=12.3, 2.5 Hz, 0H), 3.77 (s, 3H), 3.12 (dd, J=14.1, 6.7 Hz, 1H), 2.93 (dd, J=14.0, 5.1 Hz, 1H), 2.52 (t, J=7.4 Hz, 2H), 2.22-2.13 (m, 2H), 2.10 (s, 3H), 2.09 (s, 3H), 2.07 (s, 3H), 2.03 (s, 3H), 2.01 (s, 3H), 1.46 (s, 9H).

Example 19 Synthesis of S-glycoside compounds S-19-S-21 according to the present invention S-glycosyl compounds S-19-S-21 of the present invention were prepared by the same method as the above route 2. The structures and characterization were as follows:

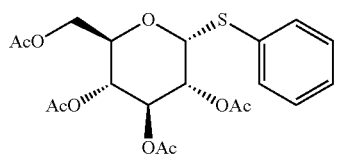

Phenyl-2,3,4,6-tetraacetyl-1-S-α-D-glucopyranose (with a purity of >90%, Yield=84%).

¹H NMR (400 MHz, chloroform-d) δ 7.46-7.42 (m, 2H), 7.33-7.27 (m, 3H), 5.92 (d, J=5.7 Hz, 0H), 5.48-5.40 (t, J=10.0 Hz, 1H), 5.09 (m, 1H), 4.57 (ddd, J=10.3, 5.2, 2.2 Hz, 1H), 4.28 (dd, J=12.4, 5.2 Hz, 1H), 4.04 (dd, J=12.3, 2.3 Hz, 1H), 2.11 (s, 3H), 2.06 (s, 1H), 2.04 (s, 3H), 2.03 (s, 3H).

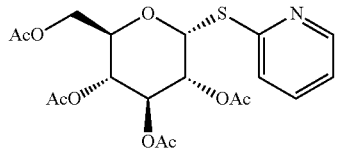

S-20

2-Pyridinyl-2,3,4,6-tetraacetyl-1-S-α-D-glucopyranose (with a purity of >90%, Yield=82%).

¹H NMR (400 MHz, chloroform-d) δ 7.78 (m, 1H), 7.30 (m, 1H), 7.08 (m, 1H), 6.68 (d, J=5.7 Hz, 1H), 5.41 (t, J=9.8 Hz, 1H), 5.26 (dd, J=10.3, 5.7 Hz, 1H), 5.13 (t, J=9.8 Hz, 1H), 4.38 (ddd, J=10.2, 4.5, 2.3 Hz, 1H), 4.27 (dd, J=12.4, 4.6 Hz, 1H), 4.01 (dd, J=12.4, 2.3 Hz, 11H), 2.04 (s, 3H), 2.04 (s, 3H), 2.02 (s, 3H), 1.98 (s, 3H).

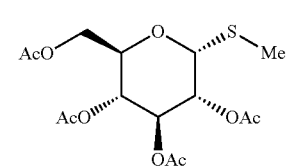

S-21

Methyl-2,3,4,6-tetraacetyl-1-S-α-D-glucopyranose (with a purity of >90%, Yield=75%).

¹H NMR (400 MHz, chloroform-d) δ 5.55 (d, J=5.8 Hz, 1H), 5.42-5.36 (t, J=9.8 Hz, 1H), 5.09-5.01 (m, 2H), 4.39 (ddd, J=10.2, 4.9, 2.3 Hz, 1H), 4.30 (dd, J=12.3, 4.9 Hz, 1H), 4.09 (dd, J=12.3, 2.3 Hz, 1H), 2.09 (s, 3H), 2.06 (s, 3H), 2.06 (s, 3H), 2.03 (s, 3H), 2.01 (s, 3H).

Example 20 Synthesis of S-glycoside compound S-23 according to the present invention S-glycosyl compound S23 of the present invention was prepared by the same method as the above route 4. The structures and characterization were as follows:

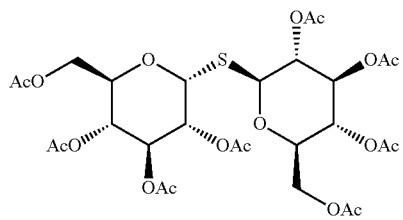

S-23

(2,3,4,6-Tetraacetoxy-α-D-glucosyl)-2,3,4,6-tetraacetoxy-1-S-β-D-glucoside (with a purity of >90%, Yield=74%).

¹H NMR (400 MHz, chloroform-d) δ 5.94 (d, J=5.6 Hz, 1H), 5.30 (t, J=9.9 Hz, 1H), 5.20-4.97 (m, 5H), 4.56 (d, J=9.9 Hz, 1H), 4.41-4.38 (m, 2H), 4.20-4.08 (m, 3H), 3.74-3.72 (m, 1H), 2.11, 2.10, 2.03, 2.02, 2.00 (5×s, 24H, 8×CH₃).

Example 21 Synthesis of S-glycoside compound S-24 according to the present invention S-glycosyl compound S-24 of the present invention was prepared using the following synthetic route. The structure and characterization are as follows:

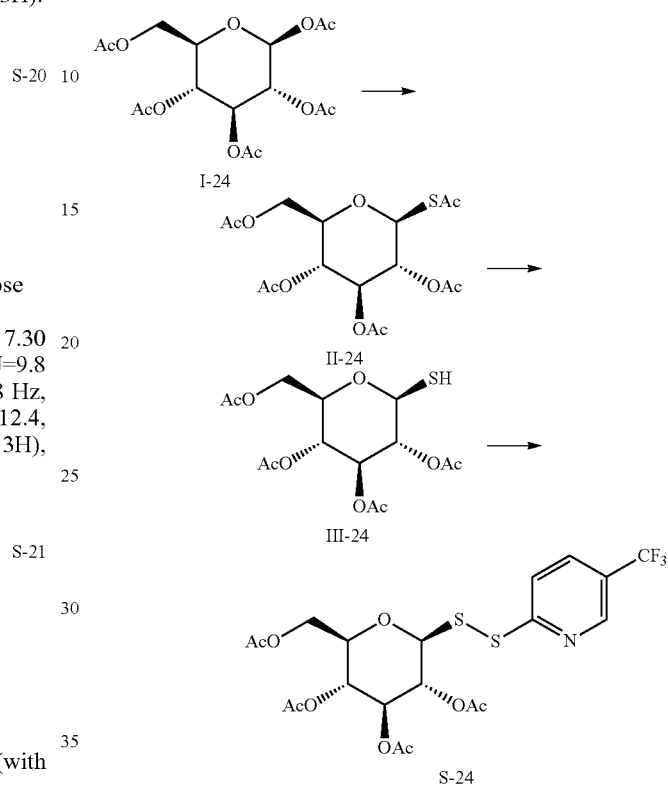

5-Trifluoromethylpyridine-1-S-(2,3,4,6-tetraacetoxy-β-D-glucosyl)disulfide

¹H NMR (400 MHz, chloroform-d) δ 8.74-8.51 (s, 1H), 8.02 (d, J=8.5 Hz, 1H), 7.83 (dd, J=8.6, 2.3 Hz, 1H), 5.31-5.20 (m, 2H), 5.10-5.02 (m, 1H), 4.73-4.64 (m, 1H), 4.10-3.95 (m, 2H), 3.70 (ddd, J=10.1, 4.4, 2.8 Hz, 1H), 2.09 (s, 3H), 2.01 (s, 6H), 1.87 (s, 3H).

The specific preparative method was:

At 0° C., 10 mmol I-24 was dissolved in dichloromethane (30 mL), to which were slowly added thioacetic acid (1.7 mL, 24 mmol) and boron trifluoride diethyl etherate (3.7 mL, 30 mmol) dropwise, and then the mixture was warmed to room temperature and stirred overnight. After the raw materials were completely reacted, the reaction was quenched with ice water, extracted with dichloromethane, and washed sequentially with saturated aqueous NaHCO₃ solution and saturated brine. The organic phase was dried with anhydrous sodium sulfate and filtered. The filtrate was rotatory evaporated to obtain product II-24.

II-24 and cysteine methyl ester hydrochloride (2.05 g, 12 mmol) were dissolved in DMF (10 mL), to which was added triethylamine (1.7 mL, 12 mmol), and the mixture was stirred at room temperature for 8 h. After II-24 was completely reacted by TLC detection, the mixture was extracted with ethyl acetate, and then washed with half-saturated brine. The organic phase was dried with anhydrous sodium sulfate and filtered. The filtrate was rotatory evaporated and purified by column chromatography to obtain product III-24.

III-24 (1.82 g, 5 mmol) and 2,2'-bis(5-trifluoromethylpyridinyl)disulfide (3.6 g, 10 mmol) were dissolved in dichloromethane (20 mL), and the mixture was stirred for 1 h at room temperature. The solvent was rotatory evaporated, and the residue was purified by column chromatography to obtain the product S-24, with a purity of >90% and a three-step yield of 57%.

Synthesis of O-Glycoside Compound

Then, the allylsulfone glycosyl donor prepared above was used as raw material to react with the glycosyl acceptor, to synthesize O-glycosyl compound of the present invention. Specific examples were as follows:

Example 22 Synthesis of O-glycosyl compound O-1 according to the present invention Under nitrogen atmosphere, allylsulfone glycosyl donor (compound 16-1, 1.5 equiv) and glycosyl acceptor (1.0 equiv) were added to the flask for catalytic reaction, to which were added initiator perfluorobutyl iodide (5.0 equiv), diammonium hydrogen phosphate (5.0 equiv), triphenylphosphine oxide (0.3 equiv), and methyl t-butyl ether (0.5 mL), and then the reaction was stirred at room temperature for 24 h under the irradiation of Blue LED, to obtain the O-glycosyl compound 0-1, with a purity of >90%.

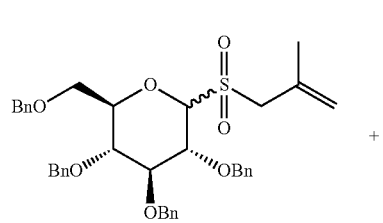

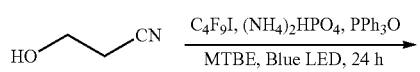

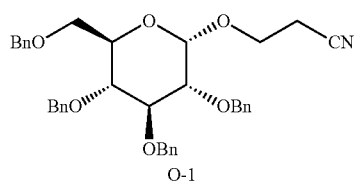

O-1

Characterization of O-glycosyl compound O-1. $^1$H NMR (400 MHz, chloroform-d) δ 7.37-7.24 (m, 18H), 7.13 (dd, J=7.3, 2.2 Hz, 2H), 4.96 (d, J=10.8 Hz, 1H), 4.83 (d, J=3.7 Hz, 1H), 4.82-4.77 (m, 2H), 4.74 (d, J=3.6 Hz, 1H), 4.63 (d, J=12.1 Hz, 1H), 4.57 (d, J=12.1 Hz, 1H), 4.48 (d, J=7.5 Hz, 1H), 4.45 (d, J=8.8 Hz, 1H), 3.96 (t, J=9.3 Hz, 1H), 3.84-3.75 (m, 2H), 3.73-3.59 (m, 4H), 3.57 (dd, J=9.7, 3.7 Hz, 1H), 2.61 (t, J=6.5 Hz, 2H); $^{13}$C NMR (101 MHz, chloroform-d) δ 138.78, 138.20, 137.87, 128.59, 128.47, 128.44, 128.23, 128.09, 128.00, 127.96, 127.93, 127.82, 127.78, 127.70, 117.65, 97.78, 81.87, 79.95, 75.83, 75.12, 73.63, 73.57, 70.89, 68.46, 63.22, 18.79.

Example 23 Synthesis of O-Glycosyl Compound O-4 According to the Present Invention

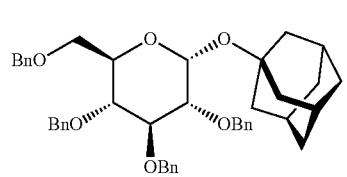

O-4

Using the same method as that of O-glycosyl compound O-1, the difference was just that the glycosyl acceptor

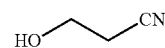

was substituted with

to prepare O-glycosyl compound O-4 of the present invention, with a purity of >90%. The structural characterization was as follows:

$^1$H NMR (400 MHz, chloroform-d) δ 7.26-7.15 (m, 18H), 7.06 (dd, J=7.4, 2.1 Hz, 2H), 5.21 (d, J=3.7 Hz, 1H), 4.91 (d, J=10.8 Hz, 1H), 4.75 (d, J=10.7 Hz, 1H), 4.72 (d, J=10.9 Hz, 1H), 4.60 (s, 2H), 4.55 (d, J=12.1 Hz, 1H), 4.39 (d, J=8.9 Hz, 1H), 4.36 (d, J=10.3 Hz, 1H), 3.98-3.89 (m, 2H), 3.68 (dd, J=10.5, 3.6 Hz, 1H), 3.60-3.50 (m, 2H), 3.46 (dd, J=9.7, 3.7 Hz, 1H), 2.05 (t, J=3.2 Hz, 3H), 1.76 (dt, J=13.9, 11.2 Hz, 6H), 1.53 (q, J=5.5, 4.7 Hz, 6H); $^{13}$C NMR (101 MHz, chloroform-d) δ 139.14, 138.44, 138.39, 138.17, 128.40, 128.37, 128.33, 128.17, 128.00, 127.92, 127.86, 127.77, 127.69, 127.61, 127.49, 89.90, 82.14, 80.17, 78.23, 75.56, 75.12, 74.58, 73.49, 72.89, 69.76, 68.88, 42.52, 36.35, 30.72.

Example 24 Synthesis of O-Glycosyl Compound O-10 According to the Present Invention

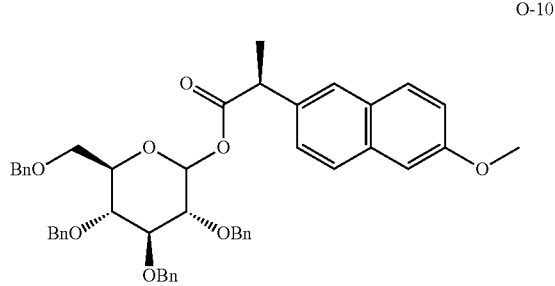 [SMILES: COc1ccc2cc([C@H](C)C(=O)OC3O[C@H](COCc4ccccc4)[C@@H](OCc4ccccc4)[C@H](OCc4ccccc4)[C@H]3OCc3ccccc3)ccc2c1]

O-10

Using the same method as that of O-glycosyl compound O-1, the difference was just that the glycosyl acceptor

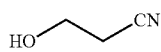

was substituted with

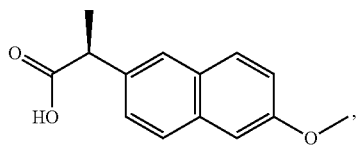 [SMILES: COc1ccc2cc([C@H](C)C(=O)O)ccc2c1]

to prepare O-glycosyl compound 0-10 of the present invention, with a purity of >90%. The structural characterization was as follows: $^1$H NMR (400 MHz, chloroform-d) δ 7.62 (d, J=1.7 Hz, 1H), 7.55 (d, J=8.5 Hz, 1H), 7.45 (d, J=8.8 Hz, 1H), 7.34 (dd, J=8.5, 1.9 Hz, 1H), 7.32-7.22 (m, 13H), 7.20 (d, J=6.4 Hz, 2H), 7.13 (ddd, J=11.5, 6.9, 2.0 Hz, 4H), 7.07 (dd, J=6.7, 2.9 Hz, 2H), 7.06-7.00 (m, 2H), 6.43 (d, J=3.2 Hz, 1H), 4.73 (d, J=10.8 Hz, 1H), 4.57 (t, J=11.9 Hz, 2H), 4.48-4.38 (m, 4H), 4.31 (d, J=11.1 Hz, 1H), 3.91 (q, I=7.1 Hz, 1H), 3.83 (s, 3H), 3.79 (ddd, J=9.9, 3.6, 2.1 Hz, 1H), 3.68-3.61 (m, 1H), 3.60 (d, J=2.2 Hz, 1H), 3.59-3.53 (m, 2H), 3.48 (t, J=9.2 Hz, 1H), 1.59 (d, J=7.1 Hz, 3H); $^{13}$C NMR (100 MHz, chloroform-d) δ 172.81, 157.58, 138.63, 138.12, 137.86, 137.72, 135.36, 133.69, 129.35, 128.90, 128.41, 128.38, 128.28, 128.27, 128.16, 127.95, 127.80, 127.75, 127.49, 126.96, 126.74, 126.26, 118.82, 105.54, 90.45, 81.22, 79.47, 76.70, 75.36, 75.07, 73.52, 73.19, 72.98, 68.22, 55.26, 55.24, 45.51, 18.03.

Synthesis of C-Glycosyl Compound:

Then, the allylsulfone glycosyl donor prepared above was used as raw material to react with the glycosyl acceptor, to synthesize C-glycosyl compound of the present invention. For example, using the above compound 3-1 as a raw material, the synthetic route was as follows:

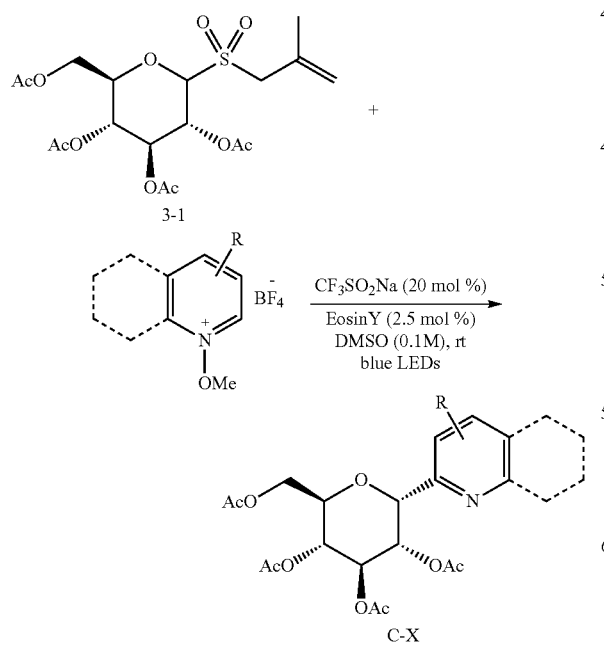

Under nitrogen atmosphere, glycosyl donor 3-1 (1.0 equiv), glycosyl acceptor pyridium tetrafluoroborate (2.0 equiv), photosensitizer EosinY (0.025 equiv), and initiator sodium trifluoromethylsulfinate (0.2 equiv.) were added to the flask for catalytic reaction, to which was added DMSO, and the reaction was stirred at room temperature for 8 h under the irradiation of Blue LED, to obtain the C-glycosyl compound C—X.

The following was specific examples of synthesizing C-glycosyl compounds:

Example 25 Synthesis of C-Glycosyl Compound According to the Present Invention

Using the same method as the above route, C-glycosyl compounds C-1, C-2, C-4, C-6, C-8 of the present invention were prepared, and the structure and characterization were as follows:

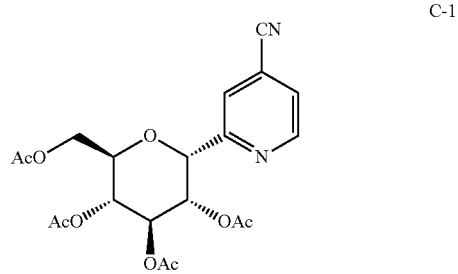

(2R,3R,4R,5S,6R)-2-(acetoxymethyl)-6-(4-cyanopyridin-2-yl)tetrahydro-2H-pyran-3,4,5-triyl triacetate (C-1), with a purity of >90%. $^1$H NMR (400 MHz, chloroform-d) δ 8.84 (d, J=5.0 Hz, 1H), 7.68 (d, J=1.5 Hz, 1H), 7.53 (d, J=5.0 Hz, 1H), 5.78 (t, J=6.6 Hz, 1H), 5.50-5.26 (m, 2H), 5.21-5.00 (m, 1H), 4.58-4.32 (m, 2H), 4.23-4.05 (m, 1H), 2.18-2.00 (m, 9H), 1.85 (d, J=1.2 Hz, 3H).

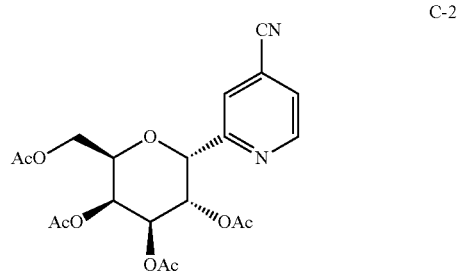 [SMILES: CC(=O)OC[C@H]1O[C@H](c2cc(C#N)ccn2)[C@H](OC(C)=O)[C@@H](OC(C)=O)[C@H]1OC(C)=O]

(2R,3S,4R,5S,6R)-2-(acetoxymethyl)-6-(4-cyanopyridin-2-yl)tetrahydro-2H-pyran-3,4,5-triyl triacetate (C-2), with a purity of >90%. $^1$H NMR (400 MHz, chloroform-d) δ 8.74 (d, J=5.0 Hz, 1H), 7.61 (s, 1H), 7.45 (dd, J=4.9, 1.5 Hz, 1H), 5.69 (dd, J=6.8, 3.3 Hz, 1H), 5.57-5.42 (m, 2H), 5.34 (d, J=4.1 Hz, 1H), 4.64-4.56 (m, 1H), 4.50 (dd, J=12.0, 8.4 Hz, 1H), 4.11 (dd, J=12.0, 4.2 Hz, 1H), 2.09 (d, J=4.5 Hz, 6H), 2.00 (s, 3H), 1.81 (s, 3H).

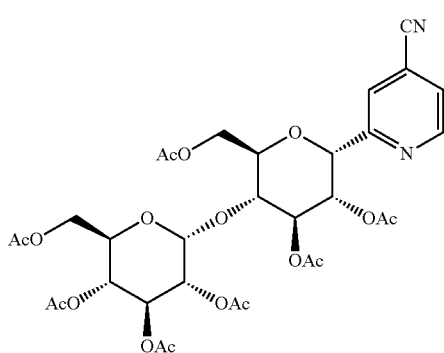

(2R,3R,4S,5R,6R)-2-(acetoxymethyl)-6-(((2R,3R,4S,5S,6R)-4,5-diacetoxy-2-(acetoxymethyl)-6-(4-cyanopyridin-2-yl)tetrahydro-2H-pyran-3-yl)oxy)tetrahydro-2H-pyran-3,4,5-triyl triacetate (C4), with a purity of >90%. $^1$H NMR (400 MHz, chloroform-d) δ 8.83-8.69 (m, 1H), 7.79 (s, 1H), 7.48 (dd, J=5.0, 1.5 Hz, 1H), 5.81-5.61 (m, 1H), 5.44-5.34 (m, 2H), 5.28 (d, J=3.9 Hz, 1H), 5.17 (dd, J=10.4, 7.8 Hz, 1H), 5.03 (dd, J=10.5, 3.4 Hz, 1H), 4.69 (d, J=7.9 Hz, 1H), 4.32 (s, 3H), 4.11 (dd, J=6.7, 3.0 Hz, 2H), 3.99 (t, J=6.7 Hz, 1H), 3.82-3.67 (m, 1H), 2.18-2.11 (m, 9H), 2.09 (s, 3H), 2.05 (s, 3H), 1.98 (s, 3H), 1.85 (s, 3H).

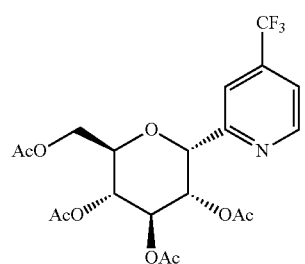

(2R,3R,4R,5S,6R)-2-(acetoxymethyl)-6-(4-(trifluoromethyl)pyridin-2-yl)tetrahydro-2H-pyran-3,4,5-triyl triacetate (C-6), with a purity of >90%. $^1$H NMR (400 MHz, chloroform-d) δ 8.85 (d, J=5.1 Hz, 1H), 7.63 (s, 1H), 7.51 (dd, J=5.1, 1.6 Hz, 1H), 5.86 (t, J=6.4 Hz, 1H), 5.38 (d, J=6.4 Hz, 2H), 5.11 (t, J=7.2 Hz, 1H), 4.48 (ddd, J=7.9, 5.8, 3.1 Hz, 1H), 4.38 (dd, J=12.2, 5.8 Hz, 1H), 4.12 (dd, J=12.2, 3.2 Hz, 1H), 2.19-2.00 (m, 9H), 1.83 (s, 3H).

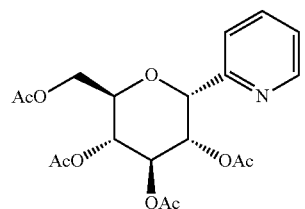

(2R,3R,4R,5S,6R)-2-(acetoxymethyl)-6-(pyridin-2-yl)tetrahydro-2H-pyran-3,4,5-triyl triacetate (C-8). $^1$H NMR (400 MHz, chloroform-d) δ 8.68 (dd, J=4.8, 1.7 Hz, 1H), 7.71 (td, J=7.7, 1.8 Hz, 1H), 7.33 (d, J=7.8 Hz, 1H), 7.28 (q, J=5.0, 4.3 Hz, 1H), 6.17 (t, J=8.1 Hz, 1H), 5.39-5.24 (m, 2H), 5.16 (t, J=8.4 Hz, 1H), 4.62-4.48 (m, 1H), 4.30 (dd, J=12.3, 4.7 Hz, 1H), 4.06 (dd, J=12.3, 2.8 Hz, 1H), 2.07 (d, J=3.7 Hz, 9H), 1.82 (s, 3H).

In summary, the present invention provided a glycosyl donor represented by formula I and a preparative method thereof, as well as the use of the glycosyl donor of formula I in the preparation of S-glycoside represented by formula III, O-glycoside represented by formula IV, and C-glycoside represented by formula V. The glycosyl donor provided by the present invention had a novel structure, that could be prepared by a simple method. In the present invention, the above-mentioned glycosyl donor was further used as a starting material, and by a free radical reaction, O-glycoside, S-glycoside, and C-glycoside compounds were prepared, most of which had a special α configuration. The preparative method was simple, the reaction conditions were mild, and the reaction had a high yield, that all indicated promising application prospects.

The invention claimed is:

1. A glycosyl donor, or a salt thereof, or a stereoisomer thereof, or an optical isomer thereof, wherein the glycosyl donor is of formula I:

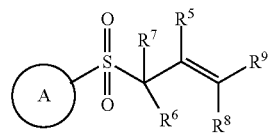

Formula I wherein,
ring A is

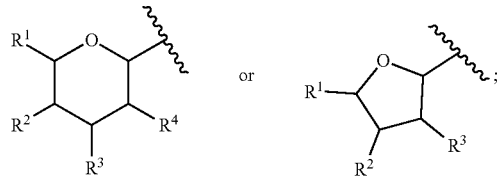

wherein, in ring A,
each of $R^2$, $R^3$, and $R^4$ is independently selected from the group consisting of H, $C_{1-6}$ alkyl, aryl substituted $C_{1-12}$ alkyl, heteroaryl substituted $C_{1-12}$ alkyl, $C_{1-12}$ alkoxyl, $C_{2-8}$ alkynyl, $C_{2-8}$ alkenyl, aryl, heteroaryl, cycloalkyl, $M_1OH$, $M_1NH_2$, $M_1NHAc$, $M_1OAc$, $M_1OBz$, $M_1OBn$, $M_1N_3$, $M_1OTMS$, $M_1OTBS$,

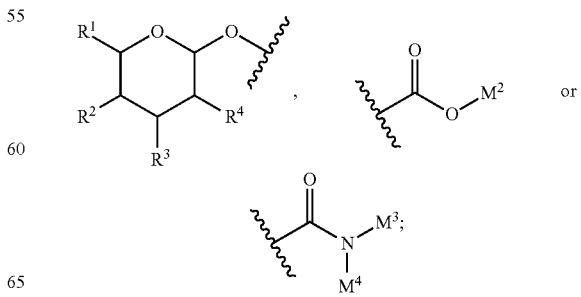

and M₁ is 0-3 methylene, while
R¹ is M₁OAc and M₁ is 1-3 methylene, or R¹ is selected from the group consisting of H, $C_{1-6}$ alkyl, aryl substituted $C_{1-12}$ alkyl, heteroaryl substituted $C_{1-12}$ alkyl, $C_{1-12}$ alkoxyl, $C_{2-8}$ alkynyl, $C_{2-8}$ alkenyl, aryl, heteroaryl, cycloalkyl, M₁OH, M₁NH₂, M₁NHAc, M₁OBz, M₁OBn, M₁N₃, M₁OTMS, M₁OTBS,

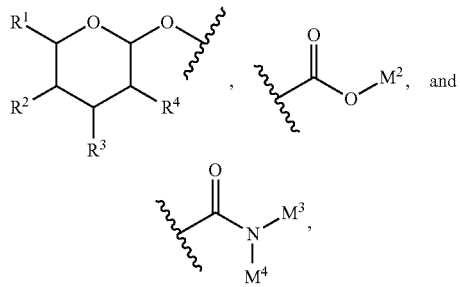

and M₁ is 0-3 methylene;
or
any two of R¹, R², R³, and R⁴ are linked to form a ring;
wherein M₂, M₃, M₄ are selected from the group consisting of H, $C_{1-6}$ alkyl, aryl substituted $C_{1-12}$ alkyl, heteroaryl substituted $C_{1-12}$ alkyl, $C_{2-8}$ alkynyl, $C_{2-8}$ alkenyl, aryl, heteroaryl, or M₃ and M₄ are linked to form a ring;
R⁵ is selected from the group consisting of $C_{1-10}$ alkyl, saturated cycloalkyl, saturated heterocyclyl, aryl, heteroaryl, $C_{1-10}$ alkoxyl, halogen, cyano, carboxyl, and ester group; and
each of R⁶, R⁷, R⁸, and R⁹ is independently selected from the group consisting of H, halogen, $C_{1-6}$ alkyl, $C_{1-6}$ alkoxyl, M₁OH, $C_{2-8}$ alkynyl, $C_{2-8}$ alkenyl, saturated cycloalkyl, saturated heterocyclyl, H, aryl, heteroaryl, cyano, and ester group.

2. The glycosyl donor according to claim 1, or a salt thereof, or a stereoisomer thereof, or an optical isomer thereof, wherein the glycosyl donor has a structure of formula II-1 or II-2:

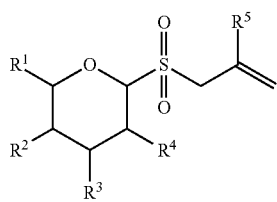

Formula II-1

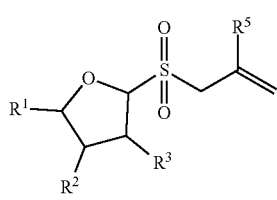

Formula II-2 wherein,
each of R², R³, and R⁴ is selected from the group consisting of H, $C_{1-6}$ alkyl, $C_{1-6}$ alkoxyl, $C_{2-6}$ alkynyl, $C_{2-6}$ alkenyl, aryl, heteroaryl, cycloalkyl, M₁OH, M₁NH₂, M₁NHAc, M₁OAc, M₁OBz, M₁OBn, M₁N₃, M₁OTMS, M₁OTBS,

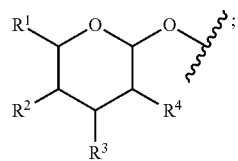

and M₁ is selected from 0-3 methylene;
or
any two of R¹, R², R³, R⁴ are linked to form a substituted or unsubstituted ring, and each of the substituents in the ring is independently one or more selected from the group consisting of H, D, $C_{1-8}$ alkyl, $C_{1-8}$ alkoxyl, $C_{2-8}$ alkynyl, $C_{2-8}$ alkenyl, aryl, heteroaryl, halogen, cyano, carboxy, and ester group;
R⁵ is selected from the group consisting of $C_{1-8}$ alkyl, saturated cycloalkyl, saturated heterocyclyl, H, aryl, heteroaryl, $C_{1-8}$ alkoxyl, halogen, cyano, carboxyl, and ester group.

3. The glycosyl donor according to claim 1, or a salt thereof, or a stereoisomer thereof, or an optical isomer thereof, wherein the structure of said glycosyl donor is selected from:

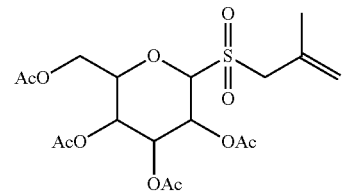

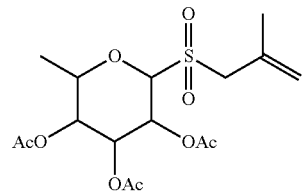

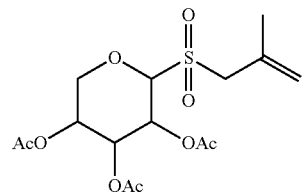

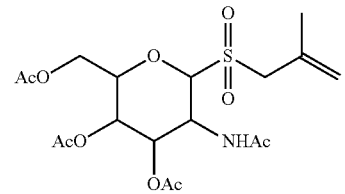

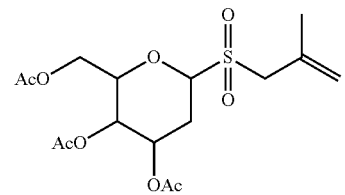

-continued
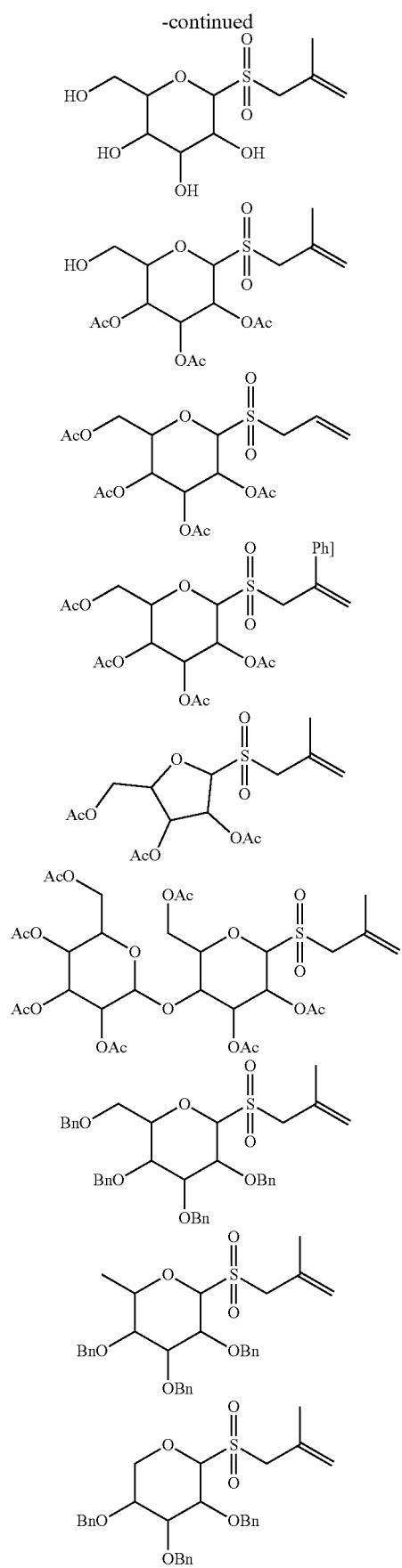
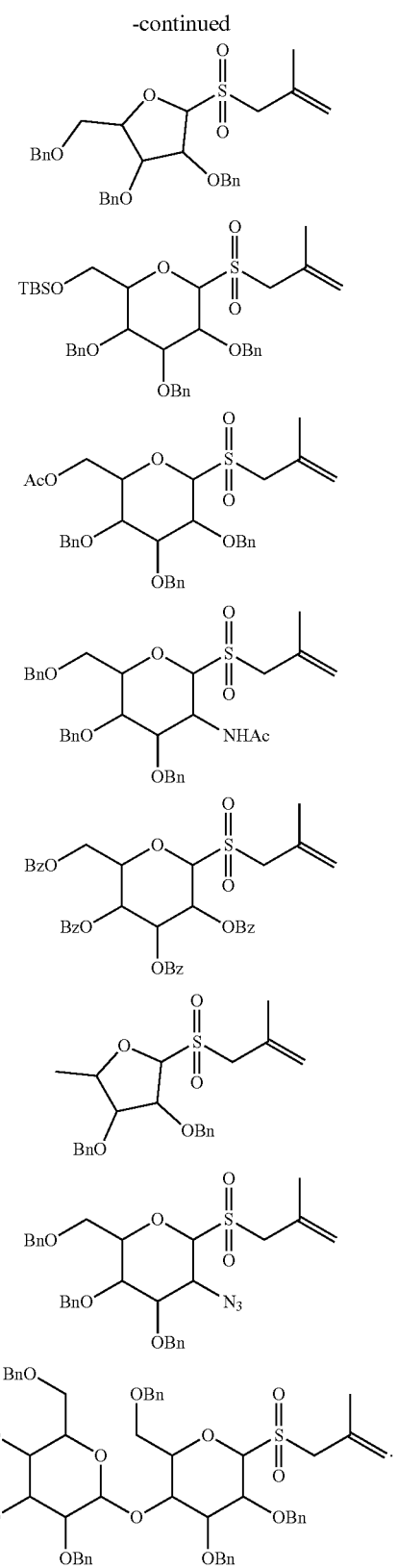
4. The glycosyl donor according to claim 1, or a salt thereof, or a stereoisomer thereof, or an optical isomer thereof, wherein the structure of said glycosyl donor is selected from:

3-1 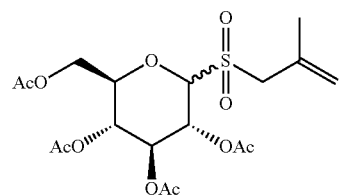
3-2 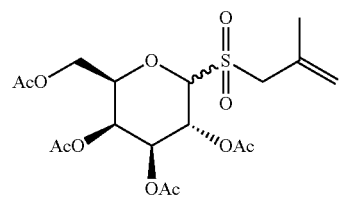
3-3 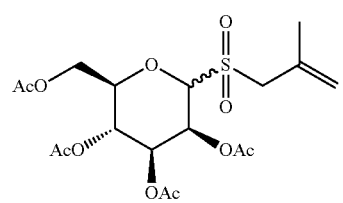
3-4 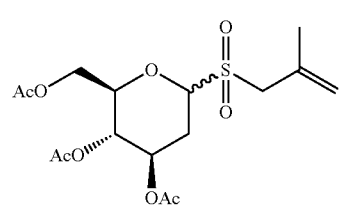
3-5 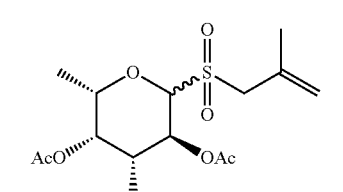
3-6 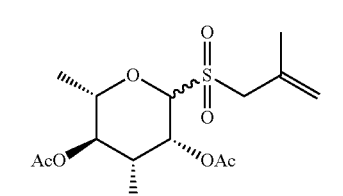
3-7 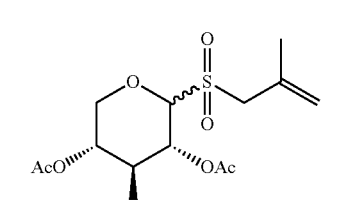
3-8 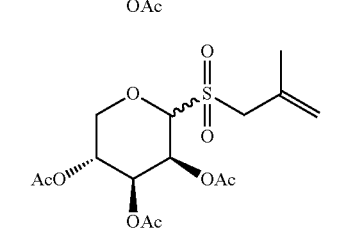
-continued
3-9 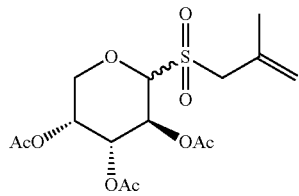
3-10 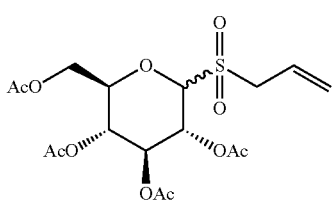
3-11 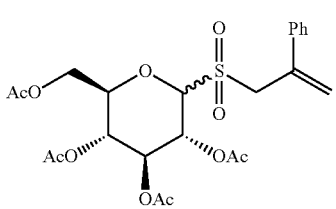
3-12 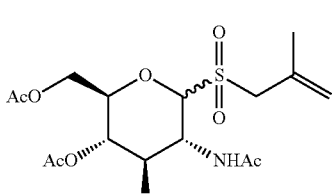
3-13 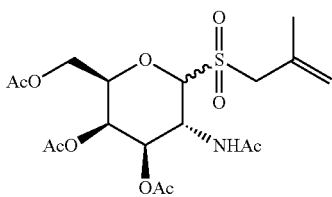
3-14 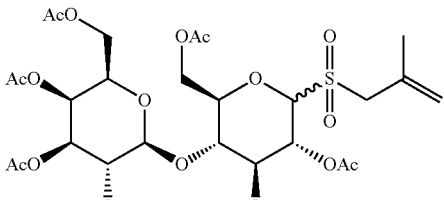
3-15 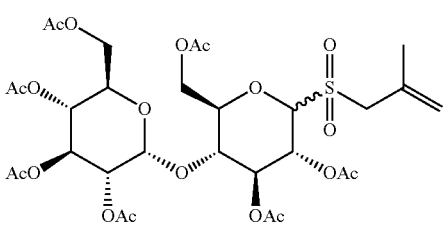

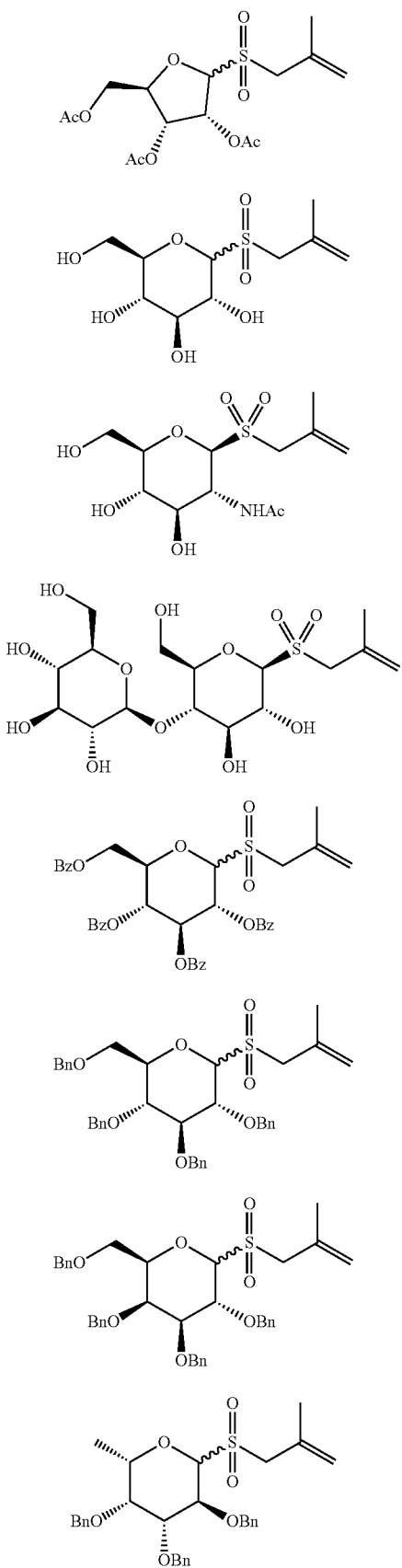

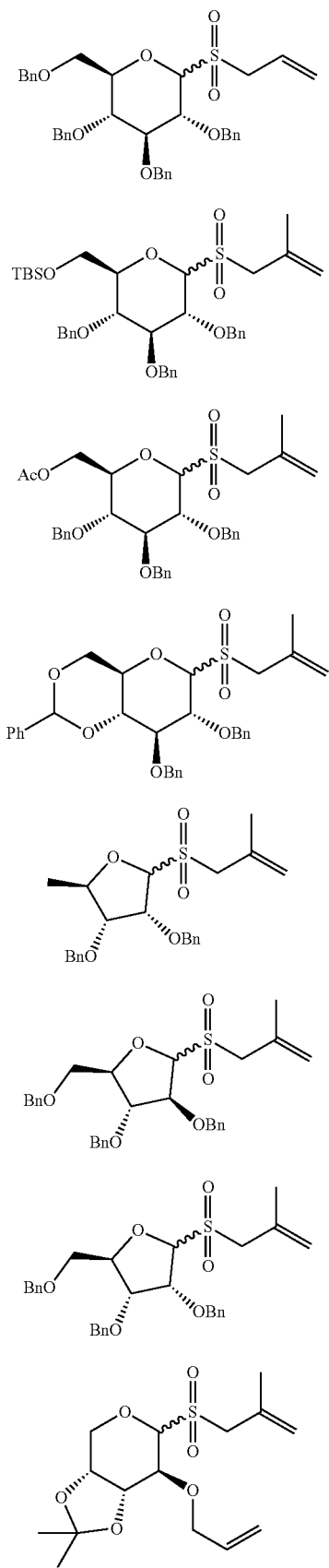

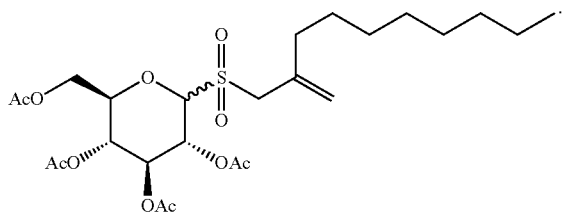

wherein

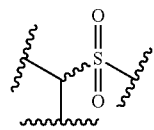 [SMILES: *C(*)S(*)(=O)=O]

represents

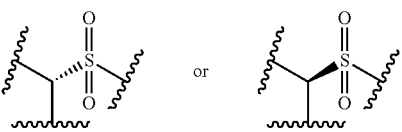

or a mixture of thereof in any ratio.

5. A method for preparation of the glycosyl donor according to claim 1, comprising:
(1) reacting a starting material Y1 with acetic anhydride to obtain compound Y2;
(2) reacting compound Y2 with thiourea to obtain a reaction mixture, and adding compound Y3 to the reaction mixture for further reaction to obtain compound Y4; and
(3) reacting Y4 reacts with mCPBA to obtain the glycosyl donor, wherein Y1 is

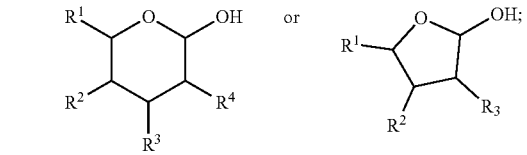

Y2 is

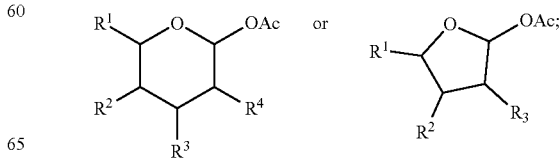

Y3 is

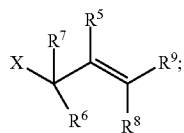

Y4 is

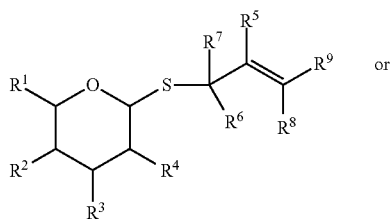 or

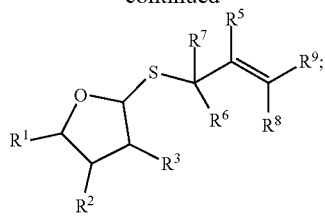

and

X is a halogen.

6. The method according to claim 5, wherein:
in step (1), a molar ratio of acetic anhydride to hydroxyl group Y1 is (0.8-1.5):1; the reaction is carried out in the presence of triethylamine and DMAP at room temperature in the solvent of dichloromethane; or
in step (2), a molar ratio of Y2, thiourea, and Y3 is 1:(1.5-4.5):(1.2-2), wherein Y2 and thiourea are reacted in the presence of boron trifluoride diethyl etherate under reflux for 2-6 hours, and, after adding Y3 into the reaction mixture, the reaction is carried out in the presence of triethyl amine under reflux for 4-8 hours in the solvent of acetonitrile;
or
in step (3), a molar ratio of Y4 to mCPBA is 1:(1.5-4.5), and the reaction is carried out for 1-3 hours in the solvent of dichloromethane.

* * * * *